(12) United States Patent
Lewis et al.

(10) Patent No.: US 10,687,903 B2
(45) Date of Patent: Jun. 23, 2020

(54) ACTIVE DRIVE FOR ROBOTIC CATHETER MANIPULATORS

(71) Applicant: Auris Health, Inc., Redwood City, CA (US)

(72) Inventors: Paul E. Lewis, Lakehead, CA (US); Alan L. Yu, Union City, CA (US)

(73) Assignee: Auris Health, Inc., Redwood City, CA (US)

( * ) Notice: Subject to any disclaimer, the term of this patent is extended or adjusted under 35 U.S.C. 154(b) by 452 days.

(21) Appl. No.: 15/142,930

(22) Filed: Apr. 29, 2016

(65) Prior Publication Data

US 2016/0235946 A1 Aug. 18, 2016

Related U.S. Application Data

(63) Continuation of application No. 13/803,535, filed on Mar. 14, 2013, now Pat. No. 9,326,822.

(51) Int. Cl.
*A61B 34/30* (2016.01)
*A61B 90/10* (2016.01)
(Continued)

(52) U.S. Cl.
CPC ......... *A61B 34/30* (2016.02); *A61M 25/0113* (2013.01); *A61B 17/3403* (2013.01);
(Continued)

(58) Field of Classification Search
CPC ......... A61B 34/30; A61B 34/37; A61B 34/70; A61B 34/71; A61B 34/72; A61B 17/3403;
(Continued)

(56) References Cited

U.S. PATENT DOCUMENTS 2,556,601 A 6/1951 Schofield
2,566,183 A 8/1951 Forss
(Continued)

FOREIGN PATENT DOCUMENTS

CA 2285342 A1 10/1998
CN 101500470 8/2009
(Continued)

OTHER PUBLICATIONS

Amendment & Response to Non-Final Office Action for U.S. Appl. No. 11/678,016, filed Dec. 27, 2010 (21 pages).
(Continued)

*Primary Examiner* — Kathleen S Holwerda
(74) *Attorney, Agent, or Firm* — Knobbe, Martens, Olson and Bear

(57) ABSTRACT

An instrument driver comprises a base and a jaw assembly coupled to the base. The jaw assembly includes a first jaw having a gripping surface and a second jaw having a gripping surface. The instrument driver further comprises a driver assembly operably coupled to the jaw assembly to advance an elongated member relative to the base by translating the first and second jaws toward each other, thereby closing the jaw assembly and gripping the member between the respective gripping surfaces of the first and second jaws, translating the jaw assembly in a first axial direction when the jaw assembly is closed, translating the first and second jaws away from each other, thereby opening the jaw assembly and releasing the member from between the respective gripping surfaces of the first and second jaws, and translating the jaw assembly in a second axial direction when the jaw assembly is opened.

17 Claims, 47 Drawing Sheets

(51) Int. Cl.
*A61B 17/34* (2006.01)
*A61M 25/01* (2006.01)
*A61B 17/29* (2006.01)
*A61F 2/95* (2013.01)
*A61B 17/00* (2006.01)

(52) U.S. Cl.
CPC . *A61B 17/3415* (2013.01); *A61B 2017/00477* (2013.01); *A61B 2017/2924* (2013.01); *A61B 2017/3409* (2013.01); *A61B 2034/301* (2016.02); *A61F 2/95* (2013.01); *A61M 25/01* (2013.01); *A61M 25/0105* (2013.01); *A61M 2025/0175* (2013.01); *Y10S 901/36* (2013.01)

(58) Field of Classification Search
CPC ...... A61B 17/3415; A61B 2017/00477; A61B 2017/2924; A61B 2017/3409; A61M 25/0113; A61M 25/01; A61M 25/0105
See application file for complete search history.

(56) References Cited

U.S. PATENT DOCUMENTS

| | | |
|---|---|---|
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,835,854 A | 9/1974 | Jewett |
| 3,921,536 A | 11/1975 | Savage |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,305 A | 7/1990 | Blood |
| 4,945,790 A | 8/1990 | Golden |
| 5,078,714 A | 1/1992 | Katims |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,339,799 A | 8/1994 | Kami et al. |
| 5,341,807 A | 8/1994 | Nardella |
| 5,346,498 A | 9/1994 | Greelis et al. |
| 5,350,101 A | 9/1994 | Godlewski |
| 5,368,015 A | 11/1994 | Wilk |
| 5,394,875 A | 3/1995 | Lewis et al. |
| 5,397,443 A | 3/1995 | Michaels |
| 5,398,691 A | 3/1995 | Martin et al. |
| 5,408,409 A | 4/1995 | Glassman et al. |
| 5,426,687 A | 6/1995 | Goodall et al. |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,507,725 A | 4/1996 | Savage et al. |
| 5,524,180 A | 6/1996 | Wang et al. |
| 5,559,294 A | 9/1996 | Hoium et al. |
| 5,600,330 A | 2/1997 | Blood |
| 5,631,973 A | 5/1997 | Green |
| 5,662,108 A | 9/1997 | Budd et al. |
| 5,673,704 A | 10/1997 | Marchlinski et al. |
| 5,697,377 A | 12/1997 | Wittkampf |
| 5,709,661 A | 1/1998 | Van Egmond |
| 5,713,946 A | 2/1998 | Ben-Haim |
| 5,722,959 A | 3/1998 | Bierman |
| 5,738,096 A | 4/1998 | Ben-Haim |
| 5,749,362 A | 5/1998 | Funda et al. |
| 5,754,741 A | 5/1998 | Wang et al. |
| 5,762,458 A | 6/1998 | Wang et al. |
| 5,767,840 A | 6/1998 | Selker |
| 5,779,623 A | 7/1998 | Leonard |
| 5,784,542 A | 7/1998 | Ohm et al. |
| 5,792,135 A | 8/1998 | Madhani et al. |
| 5,799,055 A | 8/1998 | Peshkin et al. |
| 5,815,640 A | 9/1998 | Wang et al. |
| 5,825,982 A | 10/1998 | Wright et al. |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,843,076 A | 12/1998 | Webster, Jr. et al. |
| 5,845,646 A | 12/1998 | Lemelson |
| 5,855,583 A | 1/1999 | Wang et al. |
| 5,859,934 A | 1/1999 | Green |
| 5,876,325 A | 3/1999 | Mizuno et al. |
| 5,878,193 A | 3/1999 | Wang et al. |
| 5,891,095 A | 4/1999 | Eggers et al. |
| 5,921,968 A | 7/1999 | Lampropoulos et al. |
| 5,925,078 A | 7/1999 | Anderson |
| 5,935,079 A | 8/1999 | Swanson et al. |
| 5,950,629 A | 9/1999 | Taylor et al. |
| 5,951,475 A | 9/1999 | Gueziec et al. |
| 5,953,683 A | 9/1999 | Hansen et al. |
| 5,967,934 A | 10/1999 | Ishida et al. |
| 5,983,126 A | 11/1999 | Wittkampf |
| 6,004,271 A | 12/1999 | Moore |
| 6,061,587 A | 5/2000 | Kucharczyk et al. |
| 6,063,022 A | 5/2000 | Ben-Haim |
| 6,063,095 A | 5/2000 | Wang et al. |
| 6,080,181 A | 6/2000 | Jensen et al. |
| 6,083,170 A | 7/2000 | Ben-Haim |
| 6,084,371 A | 7/2000 | Kress et al. |
| 6,096,004 A | 8/2000 | Meglan et al. |
| 6,106,511 A | 8/2000 | Jensen |
| 6,129,668 A | 10/2000 | Haynor et al. |
| 6,132,368 A | 10/2000 | Cooper |
| 6,154,000 A | 11/2000 | Rastegar et al. |
| 6,161,032 A | 12/2000 | Acker |
| 6,171,234 B1 | 1/2001 | White et al. |
| 6,172,499 B1 | 1/2001 | Ashe |
| 6,185,478 B1 | 2/2001 | Koakutsu et al. |
| 6,203,493 B1 | 3/2001 | Ben-Haim |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,504 B1 | 5/2001 | Das et al. |
| 6,246,200 B1 | 6/2001 | Blumenkranz et al. |
| 6,259,806 B1 | 7/2001 | Green |
| 6,266,551 B1 | 7/2001 | Osadchy et al. |
| 6,272,371 B1 | 8/2001 | Shlomo |
| 6,289,579 B1 | 9/2001 | Viza et al. |
| 6,301,496 B1 | 10/2001 | Reisfeld |
| 6,309,397 B1 | 10/2001 | Julian et al. |
| 6,310,828 B1 | 10/2001 | Mumm et al. |
| 6,312,435 B1 | 11/2001 | Wallace et al. |
| 6,331,181 B1 | 12/2001 | Tierney et al. |
| 6,363,279 B1 | 3/2002 | Ben-Haim et al. |
| 6,370,411 B1 | 4/2002 | Osadchy et al. |
| 6,371,952 B1 | 4/2002 | Madhani et al. |
| 6,375,471 B1 | 4/2002 | Wendlandt et al. |
| 6,380,732 B1 | 4/2002 | Gilboa |
| 6,381,483 B1 | 4/2002 | Hareyama et al. |
| 6,384,483 B1 | 5/2002 | Igarashi et al. |
| 6,393,340 B2 | 5/2002 | Funda et al. |
| 6,394,998 B1 | 5/2002 | Wallace et al. |
| 6,398,731 B1 | 6/2002 | Mumm et al. |
| 6,400,979 B1 | 6/2002 | Stoianovici et al. |
| 6,401,572 B1 | 6/2002 | Provost |
| 6,415,171 B1 | 7/2002 | Gueziec et al. |

(56) References Cited

U.S. PATENT DOCUMENTS

| | | |
|---|---|---|
| 6,424,885 B1 | 7/2002 | Niemeyer et al. |
| 6,436,107 B1 | 8/2002 | Wang et al. |
| 6,487,940 B2 | 12/2002 | Hart et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,530,913 B1 | 3/2003 | Giba et al. |
| 6,544,230 B1 | 4/2003 | Flaherty et al. |
| 6,550,128 B1 | 4/2003 | Lorenz |
| 6,551,273 B1 | 4/2003 | Olson et al. |
| 6,565,554 B1 | 5/2003 | Niemeyer |
| 6,574,355 B2 | 6/2003 | Green |
| 6,580,938 B1 | 6/2003 | Acker |
| 6,587,750 B2 | 7/2003 | Gerbi et al. |
| 6,594,552 B1 | 7/2003 | Nowlin |
| 6,610,007 B2 | 8/2003 | Belson et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,629,534 B1 | 10/2003 | St. Goar et al. |
| 6,659,939 B2 | 12/2003 | Moll et al. |
| 6,669,709 B1 | 12/2003 | Cohn et al. |
| 6,685,698 B2 | 2/2004 | Morley et al. |
| 6,695,818 B2 | 2/2004 | Wollschlager |
| 6,699,235 B2 | 3/2004 | Wallace et al. |
| 6,716,166 B2 | 4/2004 | Govari |
| 6,726,675 B1 * | 4/2004 | Beyar ............... A61M 25/0105 600/106 |
| 6,741,883 B2 | 5/2004 | Gildenberg |
| 6,774,624 B2 | 8/2004 | Anderson et al. |
| 6,783,524 B2 | 8/2004 | Anderson et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,963,792 B1 | 11/2005 | Green |
| 7,021,173 B2 | 4/2006 | Stoianovici et al. |
| 7,044,936 B2 | 5/2006 | Harding |
| 7,074,179 B2 | 7/2006 | Wang et al. |
| 7,087,049 B2 | 8/2006 | Nowlin et al. |
| 7,155,315 B2 | 12/2006 | Niemeyer et al. |
| 7,169,141 B2 | 1/2007 | Brock et al. |
| 7,172,580 B2 | 2/2007 | Hruska et al. |
| 7,225,012 B1 | 5/2007 | Susil et al. |
| 7,276,044 B2 | 10/2007 | Ferry et al. |
| 7,280,863 B2 | 10/2007 | Shachar |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 7,404,824 B1 | 7/2008 | Webler et al. |
| 7,494,494 B2 | 2/2009 | Stoianovici et al. |
| 7,540,866 B2 | 6/2009 | Viswanathan et al. |
| 7,615,042 B2 | 11/2009 | Beyar et al. |
| 7,766,856 B2 | 8/2010 | Ferry et al. |
| 7,789,874 B2 | 9/2010 | Yu et al. |
| 7,850,642 B2 | 12/2010 | Moll et al. |
| 7,938,809 B2 | 5/2011 | Lampropoulos et al. |
| 7,963,288 B2 | 6/2011 | Rosenberg et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,092,397 B2 | 1/2012 | Wallace et al. |
| 8,126,534 B2 | 2/2012 | Maschke |
| 8,146,874 B2 | 4/2012 | Yu |
| 8,157,308 B2 | 4/2012 | Pedersen |
| 8,182,415 B2 | 5/2012 | Larkin et al. |
| 8,190,238 B2 | 5/2012 | Moll et al. |
| 8,202,244 B2 | 6/2012 | Cohen et al. |
| 8,219,178 B2 | 7/2012 | Smith et al. |
| 8,235,942 B2 | 8/2012 | Frassica et al. |
| 8,244,327 B2 | 8/2012 | Fichtinger et al. |
| 8,277,417 B2 | 10/2012 | Fedinec et al. |
| 8,291,791 B2 | 10/2012 | Light et al. |
| 8,343,040 B2 | 1/2013 | Frassica et al. |
| 8,425,465 B2 * | 4/2013 | Nagano ............ A61B 17/12113 604/156 |
| 8,498,691 B2 | 7/2013 | Moll et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,023,068 B2 | 5/2015 | Viola |
| 9,168,356 B2 | 10/2015 | Wenderow et al. |
| 9,173,713 B2 | 11/2015 | Hart et al. |
| 9,204,933 B2 | 12/2015 | Reis et al. |
| 9,314,306 B2 | 4/2016 | Yu |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,566,201 B2 | 2/2017 | Yu |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,750,576 B2 | 9/2017 | Murphy et al. |
| 9,763,741 B2 | 9/2017 | Alvarez et al. |
| 9,788,910 B2 | 10/2017 | Schuh |
| 9,789,285 B1 | 10/2017 | Blacker |
| 9,818,681 B2 | 11/2017 | Machida |
| 9,833,293 B2 | 12/2017 | Wenderow et al. |
| 9,844,412 B2 | 12/2017 | Bogusky et al. |
| 9,855,101 B2 | 1/2018 | Wenderow et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,143,360 B2 | 12/2018 | Roelle et al. |
| 10,145,747 B1 | 12/2018 | Lin et al. |
| 10,159,532 B1 | 12/2018 | Ummalaneni et al. |
| 2001/0009976 A1 | 7/2001 | Panescu et al. |
| 2001/0029366 A1 | 10/2001 | Swanson et al. |
| 2001/0042643 A1 | 11/2001 | Krueger et al. |
| 2002/0045905 A1 | 4/2002 | Gerbi et al. |
| 2002/0087169 A1 | 7/2002 | Brock et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0138009 A1 | 9/2002 | Brockway et al. |
| 2002/0156369 A1 | 10/2002 | Chakeres |
| 2002/0161355 A1 | 10/2002 | Wollschlager |
| 2002/0161426 A1 | 10/2002 | Lancea |
| 2002/0177789 A1 * | 11/2002 | Ferry ................ A61B 1/00147 600/585 |
| 2003/0050649 A1 | 3/2003 | Brock et al. |
| 2003/0056561 A1 | 3/2003 | Butscher et al. |

(56) References Cited

U.S. PATENT DOCUMENTS

| | | |
|---|---|---|
| 2003/0073908 A1 | 4/2003 | Desai |
| 2003/0074011 A1 | 4/2003 | Gilboa et al. |
| 2003/0109780 A1 | 6/2003 | Goste-Maniere et al. |
| 2003/0135204 A1 | 7/2003 | Lee et al. |
| 2004/0015053 A1 | 1/2004 | Bieger |
| 2004/0034282 A1 | 2/2004 | Quaid, III |
| 2004/0034365 A1 | 2/2004 | Lentz et al. |
| 2004/0152972 A1 | 8/2004 | Hunter |
| 2004/0167559 A1 | 9/2004 | Taylor et al. |
| 2004/0171929 A1 | 9/2004 | Leitner et al. |
| 2004/0176751 A1 | 9/2004 | Weitzner et al. |
| 2004/0193146 A1 | 9/2004 | Lee et al. |
| 2004/0220588 A1 | 11/2004 | Kermode et al. |
| 2004/0243147 A1 | 12/2004 | Lipow |
| 2005/0004579 A1 | 1/2005 | Schneider et al. |
| 2005/0027397 A1 | 2/2005 | Niemeyer |
| 2005/0059960 A1 | 3/2005 | Simaan et al. |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0182295 A1 | 8/2005 | Soper et al. |
| 2005/0182330 A1 | 8/2005 | Brockway et al. |
| 2005/0183532 A1 | 8/2005 | Najaf et al. |
| 2005/0200324 A1 | 9/2005 | Guthart et al. |
| 2005/0203382 A1 | 9/2005 | Govari et al. |
| 2005/0222554 A1 | 10/2005 | Wallace et al. |
| 2006/0013523 A1 | 1/2006 | Childers et al. |
| 2006/0025676 A1 | 2/2006 | Viswanathan et al. |
| 2006/0025679 A1 | 2/2006 | Viswanathan et al. |
| 2006/0041245 A1 | 2/2006 | Ferry |
| 2006/0058647 A1 | 3/2006 | Strommer et al. |
| 2006/0111692 A1 | 5/2006 | Hlavka et al. |
| 2006/0146010 A1 | 7/2006 | Schneider |
| 2006/0178556 A1 | 8/2006 | Hasser et al. |
| 2006/0200049 A1 | 9/2006 | Leo et al. |
| 2006/0201688 A1 | 9/2006 | Jenner et al. |
| 2006/0229587 A1 | 10/2006 | Beyar et al. |
| 2006/0229641 A1 | 10/2006 | Gupta et al. |
| 2006/0237205 A1 | 10/2006 | Sia et al. |
| 2006/0271036 A1 | 11/2006 | Garabedian et al. |
| 2007/0000498 A1 | 1/2007 | Glynn et al. |
| 2007/0013336 A1 | 1/2007 | Nowlin et al. |
| 2007/0038181 A1 | 2/2007 | Melamud et al. |
| 2007/0043338 A1* | 2/2007 | Moll .............. A61B 17/062 606/1 |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0123851 A1 | 5/2007 | Alejandro et al. |
| 2007/0149946 A1* | 6/2007 | Viswanathan ..... A61M 25/0113 604/500 |
| 2007/0156123 A1 | 7/2007 | Moll et al. |
| 2007/0185486 A1 | 8/2007 | Hauck et al. |
| 2007/0191177 A1 | 8/2007 | Nagai et al. |
| 2007/0197939 A1 | 8/2007 | Wallace et al. |
| 2007/0239028 A1 | 10/2007 | Houser |
| 2007/0245175 A1 | 10/2007 | Zheng et al. |
| 2007/0249901 A1 | 10/2007 | Ohline et al. |
| 2007/0287999 A1 | 12/2007 | Malecki et al. |
| 2007/0293724 A1 | 12/2007 | Saadat et al. |
| 2007/0299427 A1 | 12/2007 | Yeung et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0039255 A1 | 2/2008 | Jinno et al. |
| 2008/0046122 A1 | 2/2008 | Manzo et al. |
| 2008/0064920 A1 | 3/2008 | Bakos et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0183071 A1 | 7/2008 | Strommer et al. |
| 2008/0214925 A1 | 9/2008 | Wilson et al. |
| 2008/0243064 A1 | 10/2008 | Stahler et al. |
| 2008/0245946 A1 | 10/2008 | Yu |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0300592 A1 | 12/2008 | Weitzner et al. |
| 2008/0302200 A1 | 12/2008 | Tobey |
| 2008/0319311 A1 | 12/2008 | Hamadeh |
| 2009/0054884 A1 | 2/2009 | Farley et al. |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0131872 A1 | 5/2009 | Popov |
| 2009/0137952 A1 | 5/2009 | Ramamurthy et al. |
| 2009/0171371 A1 | 7/2009 | Nixon |
| 2009/0221908 A1 | 9/2009 | Glossop |
| 2009/0247944 A1 | 10/2009 | Kirschenman et al. |
| 2009/0318797 A1 | 12/2009 | Hadani |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081920 A1 | 4/2010 | Whitmore, III et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0187740 A1 | 7/2010 | Orgeron |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0016346 A1 | 1/2012 | Steinmetz et al. |
| 2012/0046652 A1 | 2/2012 | Sokel |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0078080 A1 | 3/2012 | Foley et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0241576 A1 | 9/2012 | Yu |
| 2012/0245595 A1 | 9/2012 | Kesavadas et al. |
| 2012/0277730 A1 | 11/2012 | Salahieh |
| 2012/0283747 A1 | 11/2012 | Popovic |
| 2012/0310112 A1 | 12/2012 | Fichtinger et al. |
| 2012/0316393 A1 | 12/2012 | Frassica et al. |
| 2013/0012779 A1 | 1/2013 | Frassica et al. |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0269109 A1 | 10/2013 | Yu |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0171919 A1 | 6/2014 | Blacker |
| 2014/0222019 A1 | 8/2014 | Brudnick |
| 2014/0276233 A1 | 9/2014 | Murphy |
| 2014/0276389 A1 | 9/2014 | Walker |
| 2014/0276391 A1 | 9/2014 | Yu |
| 2014/0276394 A1 | 9/2014 | Wong et al. |
| 2014/0276594 A1 | 9/2014 | Tanner et al. |
| 2014/0276647 A1 | 9/2014 | Yu |

(56) References Cited

U.S. PATENT DOCUMENTS

| | | |
|---|---|---|
| 2014/0276935 A1 | 9/2014 | Yu |
| 2014/0276936 A1 | 9/2014 | Kokish et al. |
| 2014/0276939 A1 | 9/2014 | Kokish et al. |
| 2014/0277333 A1 | 9/2014 | Lewis et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0001968 A1 | 1/2015 | Zirps |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133858 A1 | 5/2015 | Julian et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0100896 A1 | 4/2016 | Yu |
| 2016/0157945 A1 | 6/2016 | Madhani |
| 2016/0166234 A1 | 6/2016 | Zhang |
| 2016/0193445 A1 | 7/2016 | Zirps et al. |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0348060 A1 | 12/2017 | Blacker |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |

FOREIGN PATENT DOCUMENTS

| | | |
|---|---|---|
| CN | 102665590 | 9/2012 |
| DE | 19649082 | 1/1998 |
| DE | 102004020465 | 9/2005 |
| EP | 1 442 720 | 8/2004 |
| EP | 2567670 | 3/2013 |
| EP | 3 025 630 | 6/2016 |
| JP | 2009-139187 | 6/2009 |
| JP | 2010-046384 | 3/2010 |
| WO | 9744089 A1 | 11/1997 |
| WO | 0011495 A1 | 3/2000 |
| WO | 0045193 A1 | 8/2000 |
| WO | WO 02/074178 | 9/2002 |
| WO | 03077769 A1 | 9/2003 |
| WO | 03086190 A1 | 10/2003 |
| WO | 03091839 A2 | 11/2003 |
| WO | 2005087128 A1 | 9/2005 |
| WO | WO 07/146987 | 12/2007 |
| WO | WO 09/092059 | 7/2009 |
| WO | WO 11/005335 | 1/2011 |
| WO | 2012037506 A2 | 3/2012 |
| WO | WO 12/037213 | 3/2012 |
| WO | WO 13/043804 | 3/2013 |
| WO | WO 13/179600 | 12/2013 |
| WO | 2014028702 A1 | 2/2014 |
| WO | 2014028699 A1 | 2/2014 |
| WO | WO 15/127231 | 8/2015 |
| WO | WO 17/059412 | 4/2017 |
| WO | WO 17/0151993 | 9/2017 |
| WO | WO 18/165162 | 9/2018 |

OTHER PUBLICATIONS

European Search Report for European Patent Application No. 14160068.4, dated Feb. 6, 2015 (6 pages).

(56) References Cited

OTHER PUBLICATIONS

European Search Report for European Patent Application No. 14160078.3, dated Feb. 11, 2015 (6 pages).
Non-Final Office Action for U.S. Appl. No. 11/678,016, dated Aug. 31, 2010 (30 pages).
European Office Action for European Patent Application No. 07757358.2, dated Dec. 9, 2008 (3 pages).
Chinese Office Action for Chinese Patent Application No. 200780006359.8, dated Aug. 9, 2010 (6 pages).
PCT International Preliminary Report on Patentability for International Patent Application No. PCT/US2007/062617, dated Aug. 26, 2008 (7 pages).
PCT International Search Report for International Patent Application No. PCT/US2006/026218, dated Dec. 12, 2006 (2 pages).
PCT International Search Report for International Patent Application No. PCT/US2005/007108, dated Jun. 27, 2005 (4 pages).
PCT Written Opinion for International Patent Application No. PCT/US2006/026218, dated Dec. 12, 2006 (7 pages).
PCT Written Opinion for International Patent Application No. PCT/US2005/007108, dated Jun. 27, 2005 (6 pages).
Mayo Clinic, Robotic Surgery, https://www.mayoclinic.org/tests-procedures/robotic-surgery/about/pac-20394974?p=1, downloaded from the internet on Jul. 12, 2018, 2 pp.

\* cited by examiner

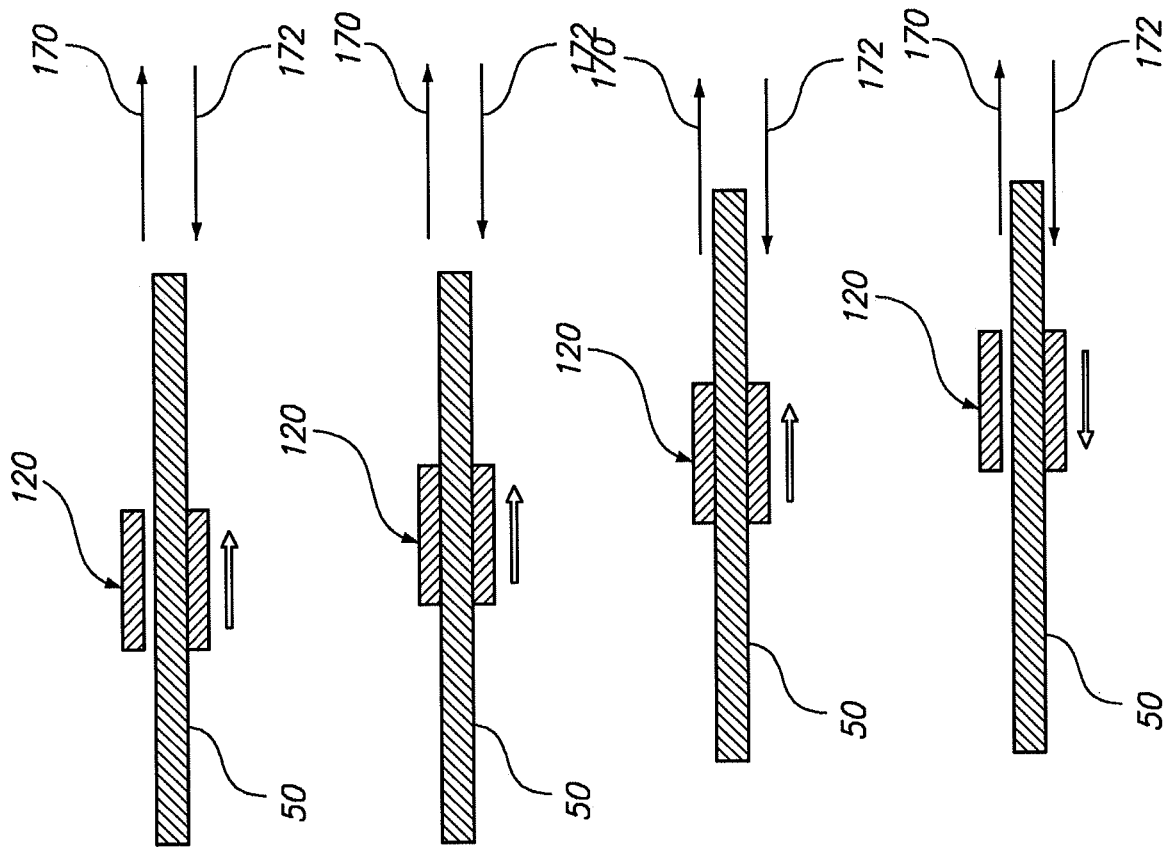

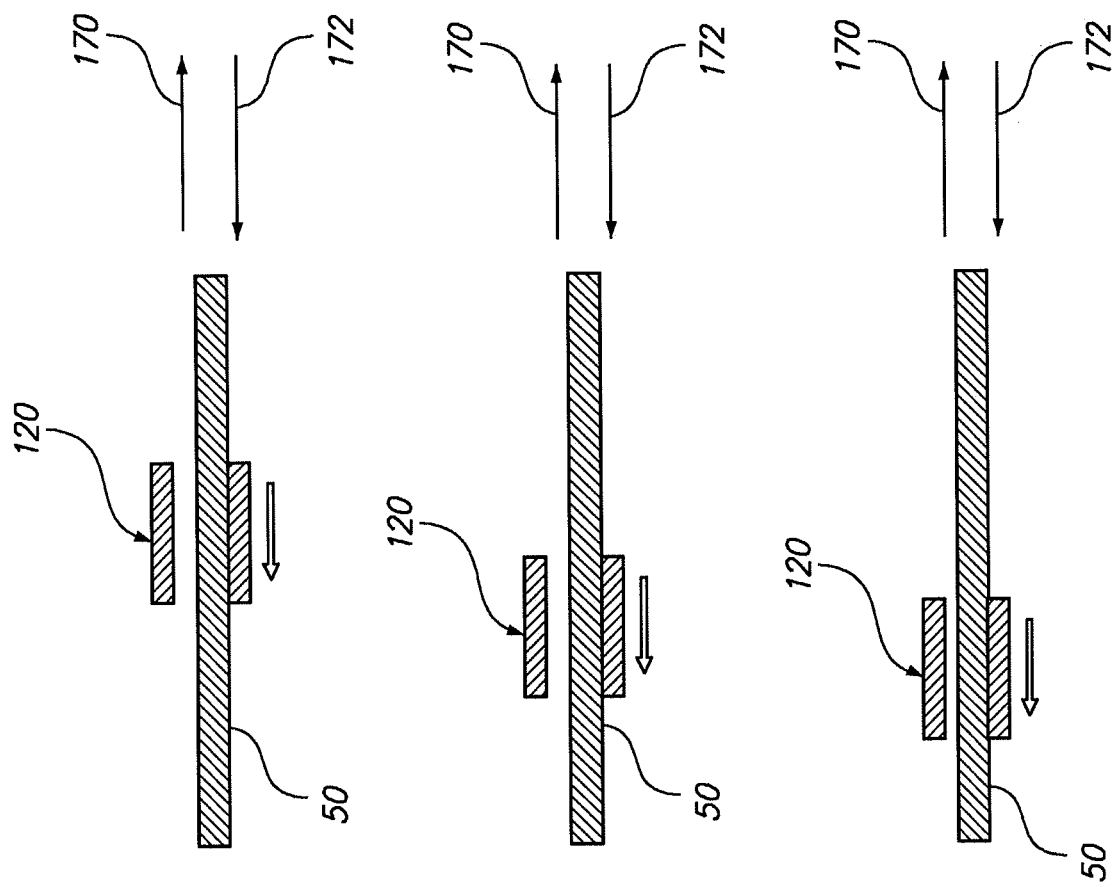

ACTIVE DRIVE FOR ROBOTIC CATHETER MANIPULATORS

CROSS-REFERENCE TO RELATED APPLICATIONS

This application is a continuation of U.S. patent application Ser. No. 13/803,535, entitled "ACTIVE DRIVES FOR ROBOTIC CATHETER MANIPULATORS," filed Mar. 14, 2013. The entirety of the above-reference application is hereby incorporated by reference.

FIELD OF INVENTION

The invention relates robotic catheter manipulators, and more particularly to drive mechanisms for inserting/retracting catheters in such robotic catheter manipulators.

BACKGROUND

Minimally invasive procedures are preferred over conventional techniques wherein the patient's body cavity is open to permit the surgeon's hands access to internal organs. Thus, there is a need for a highly controllable yet minimally sized system to facilitate imaging, diagnosis, and treatment of tissues which may lie deep within a patient, and which may be accessed via naturally-occurring pathways, such as blood vessels, other lumens, via surgically-created wounds of minimized size, or combinations thereof.

Currently known minimally invasive procedures for the treatment of cardiac, vascular, and other disease conditions use manually or robotically actuated instruments, which may be inserted transcutaneously into body spaces such as the thorax or peritoneum, transcutaneously or percutaneously into lumens such as the blood vessels, through natural orifices and/or lumens such as the mouth and/or upper gastrointestinal tract, etc. Manually and robotically-navigated interventional systems and devices, such as steerable catheters, are well suited for performing a variety of minimally invasive procedures. Manually-navigated catheters generally have one or more handles extending from their proximal end with which the operator may steer the pertinent instrument. Robotically-navigated catheters may have a proximal interface configured to interface with a catheter driver comprising, for example, one or more motors configured to induce navigation of the catheter in response to computer-based automation commands input by the operator at a master input device in the form of a work station.

In the field of electrophysiology, robotic catheter navigation systems, such as the Sensei® Robotic Catheter System (manufactured by Hansen Medical, Inc.), have helped clinicians gain more catheter control that accurately translates the clinician's hand motions at the workstation to the catheter inside the patient's heart, reduce overall procedures (which can last up to four hours), and reduce radiation exposure due to fluoroscopic imaging necessary to observe the catheter relative to the patient anatomy, and in the case of electrophysiology, within the relevant chamber in the heart. The Sensei® Robotic Catheter System employs a steerable outer catheter and a steerable inner electrophysiology (EP) catheter, which can be manually introduced into the patient's heart in a conventional manner. The outer and inner catheters are arranged in an "over the wire" telescoping arrangement that work together to advance through the tortuous anatomy of the patient. The outer catheter, often referred to as a guiding sheath, provides a steerable pathway for the inner catheter. Proximal adapters on the outer guide sheath and inner EP catheter can then be connected to the catheter driver, after which the distal ends of the outer sheath and inner EP catheter can be robotically manipulated in the heart chamber within six degrees of freedom (axial, roll, and pitch for each) via operation of the Sensei® Robotic Catheter System.

While the Sensei® Robotic Catheter System is quite useful in performing robotic manipulations at the operational site of the patient, it is desirable to employ robotic catheter systems capable of allowing a physician to access various target sites within the human vascular system. In contrast to the Sensei® Robotic Catheter System, which is designed to perform robotic manipulations within open space (i.e., within a chamber of the heart) after the outer guide sheath and inner catheter are manually delivered into the heart via a relatively non-tortuous anatomical route (e.g., via the vena cava), and therefore may be used in conjunction with sheaths and catheters that are both axially and laterally rigid, robotic catheter systems designed to facilitate access to the desired target sites in the human vascular system require simultaneous articulation of the distal tip with continued insertion or retraction of an outer guide sheath and an inner catheter. As such, the outer guide sheath and inner catheter should be laterally flexible, but axially rigid to resist the high axial loads being applied to articulate the outer guide sheath or inner catheter, in order to track through the tortuous anatomy of the patient. In this scenario, the inner catheter, sometimes called the leader catheter extends beyond the outer sheath and is used to control and bend a guidewire that runs all the way through the leader catheter in an over-the-wire configuration. The inner catheter also works in conjunction with the outer guide sheath and guidewire in a telescoping motion to inchworm the catheter system through the tortuous anatomy. Once the guidewire has been positioned beyond the target anatomical location, the leader catheter is usually removed so that a therapeutic device can be passed through the steerable sheath and manually operated.

Robotically navigating a guide sheath, an inner catheter, and a guidewire through the anatomy of a patient, in contrast to robotically manipulating a guide sheath and inner catheter at a work site in which these devices have previously been manually delivered, increases the complexity of the robotic catheter system. For example, as shown in FIG. 1, robotic catheter systems typically employ a robotic instrument driver 1 to provide robotic insertion and retraction actuation, as well as robotic steering actuation, to a telescoping assembly of elongated flexible instruments. The instrument driver 1 comprises a housing 2 that contains motors (not shown) for providing the robotic actuators to the telescoping assembly, which may include an outer steerable guide sheath 3, an inner steerable leader catheter 4 disposed within the sheath catheter, and a conventional guidewire 5 disposed within the leader catheter 2.

The robotic instrument driver 1 may robotically insert/retract the leader catheter 2 relative to the sheath catheter 1. To this end, the proximal ends of the guide sheath 3 and leader catheter 4 are mechanically interfaced to the housing 2 of the instrument driver 1 in such a manner that they may be axially translated relative to each other via operation of the motors, thereby effecting insertion or retraction movements of the respective guide sheath 3 and leader catheter 4. In the illustrated embodiment, the guide sheath 3 and leader catheter 4 respectively include proximal steering adapters 6, 7 ("splayers") mounted to associated mounting plates 8, 9 on a top portion of the instrument driver 1. The mounting plate 8 is affixed to the distal end of the instrument driver 1, whereas the mounting plate 9 is affixed to a carriage (not shown) within the housing 2 of the instrument driver 1 that can be translated relative to the mounting plate 8 via one or more motors (not shown) within the housing 2 of the instrument driver 1, thereby allowing the proximal steering adapter 7 to be translated relative to the proximal steering adapter 6, and thus, the associated leader catheter 4 to be inserted/retracted within the guide sheath 3. In the illustrated embodiment, each of the proximal adapters 6, 7 can be actuated via motors (not shown) within the housing 2 of the instrument driver 1 to deflect or articulate the distal ends of the respective in any direction.

Unlike the steerable guide sheath 3 and leader catheter 4, the distal ends of which can be robotically articulated via the instrument driver 1, the guidewire 5 is conventional, and thus, its distal end is not capable of being robotically articulated. Instead, as with most conventional guidewires, the guidewire 5 may be manipulated by simultaneously rolling while axially displacing the guidewire. In a non-robotic environment, such manipulations can be accomplished by pinching the proximal end of the guidewire between the forefinger and thumb of the physician and moving the forefinger relative to the thumb while axially displacing the guidewire.

In order to navigate the guide sheath 3 and leader catheter 4 through the tortuous anatomy of a patient, it is desirable that these components be laterally flexible. However, the flexibility of the leader catheter 4 may create issues when performing the robotic insertion actuation. In particular, due to the flexibility of the leader catheter 4 and the relatively long distance between the mounting plate 9 and the point at which the leader catheter 4 is contained within the guide sheath 3, translation of the mounting plate 9 towards the mounting plate 8 with the intention of inserting the leader catheter 4 within the guide sheath 3 may actually cause the leader catheter 4 to buckle, thereby preventing it, or at least hindering it, from axially translating within the guide sheath 3. Although "passive" anti-buckling devices may be used to add lateral support to the leader catheter 4, thereby preventing the leader catheter 4 from buckling, these anti-buckling devices may be too cumbersome and time-consuming for medical personnel to install.

Furthermore, emulating a manual guidewire manipulation in a robotic catheter system is not a straightforward procedure. For example, although the instrument driver 1 illustrated in FIG. 1 can be designed to robotically insert/retract the guidewire 5 relative to the leader catheter 4 in the same manner in which the instrument 1 uses to robotically insert/retract the leader catheter 4 relative to the guide sheath 3, such an arrangement may be impractical. In particular, the incorporation of an additional carriage within the housing 2 will disadvantageously increase the length of the instrument driver 1, which must accommodate the telescoping assembly when assuming a maximum retraction between the leader catheter 4 and guide sheath 3 and between the guidewire 5 and leader catheter 4. The increased size of the instrument driver 1 may be impractical and too big and heavy to be mounted on a table in a catheter lab environment. Thus, it is preferable that any drive device that inserts/retracts the guidewire 5 relative to the leader catheter 4 be immobile relative to the proximal end of the leader catheter 4, e.g., by locating it on the same carriage that is associated with the leader catheter 4. This drive device must also be capable of rolling the guidewire 5.

Furthermore, the use of an additional carriage for the guidewire 5 would also require the installation of an additional "passive" anti-buckling device. Because medical personnel often exchange out guidewires that are as long as 300 cm in length, the use of a "passive" anti-buckling device not only may be tedious for medical personnel to install, the extended length of the anti-buckling device due to the length of the guidewire may render the anti-buckling device functionally impractical.

There, thus, remains a need to provide an improved an instrument driver for a robotic catheter system that prevents a leader catheter from buckling when inserted within a guide sheath and/or prevents a guidewire from buckling when inserted within a leader catheter without overly increasing the length of the instrument driver.

SUMMARY OF THE INVENTION

In accordance with a first aspect of the present inventions, a medical system comprises a telescoping catheter assembly comprising an outer guide sheath and an inner catheter. The outer guide sheath includes an elongated sheath body and a proximal sheath adapter affixed to the sheath body, and the inner catheter includes an elongated catheter body and a proximal catheter adapter affixed to the catheter body.

The medical system further comprises an instrument driver comprising a sheath interface to which the proximal sheath adapter is configured for being mated, and a slidable carriage to which the proximal catheter adapter is configured for being mated. In one embodiment, the proximal sheath adapter and proximal catheter adapter are respectively configured for being releasably mated to the sheath interface and slidable carriage.

The instrument driver further includes a feeder mechanism affixed between the sheath interface and slidable carriage for engaging the catheter body. In one embodiment, the feeder mechanism is affixed relative to the sheath interface. In another embodiment, the feeder mechanism comprises at least one pair of opposing gripping elements configured for engaging the catheter body. Each pair of opposing gripping element(s) may comprise a pair of opposing gripping pads configured for being linearly translated to actively advance the catheter body within the sheath body. Or, each pair of opposing gripping element(s) may comprise a pair of opposing rotatable gripping pads configured for being rotated opposite to each other to actively advance the catheter body within the sheath body. In either case, the feeder mechanism may be configured for actively advancing the catheter body within the sheath body at an infinite linear range.

The instrument driver further includes at least one motor configured for translating the slidable carriage distally towards the sheath interface to translate the proximal catheter adapter towards the proximal sheath adapter while operating the feeder mechanism to actively advance the catheter body within the sheath body. In one embodiment, the motor(s) is configured for translating the slidable carriage distally away from sheath interface to translate the proximal catheter adapter away from the proximal sheath adapter while operating the feeder mechanism to actively retract the catheter body within the sheath body. The motor(s) may optionally be configured for operating each of the proximal sheath adapter and the proximal catheter adapter to respectively articulate distal ends of the sheath body and the catheter body. The instrument driver may further comprise a housing containing the motor(s).

In an optional embodiment, the telescoping catheter assembly further comprises a guidewire, and the instrument driver further comprises a drive mechanism configured for engaging the guidewire. In this case, the motor(s) is configured for operating the drive mechanism to advance the guidewire within the catheter body. The motor(s) may further be configured for operating the drive mechanism to simultaneously advance the guidewire within the catheter body and roll the guidewire about a longitudinal axis. In one embodiment, the instrument driver is a robotic instrument driver, in which case, medical system may further comprise a master input device configured for receiving commands from a user, and a computer configured for controlling the robotic instrument driver in accordance with the user commands.

In accordance with a second aspect of the present inventions, an instrument driver for a telescoping catheter assembly is provided. The telescoping catheter assembly comprises an outer guide sheath and an inner catheter. The outer guide sheath includes an elongated sheath body and a proximal sheath adapter affixed to the sheath body, and the inner catheter includes an elongated catheter body and a proximal catheter adapter affixed to the catheter body.

The instrument driver comprises a sheath interface to which the proximal sheath adapter is configured for being mated, and a slidable carriage to which the proximal catheter adapter is configured for being mated. In one embodiment, the proximal sheath adapter and proximal catheter adapter are respectively configured for being releasably mated to the sheath interface and slidable carriage.

The instrument driver further comprises a feeder mechanism affixed between the sheath interface and slidable carriage and being configured for engaging the catheter body. In one embodiment, the feeder mechanism is affixed relative to the sheath interface. In another embodiment, the feeder mechanism comprises at least one pair of opposing gripping elements configured for engaging the catheter body. Each pair of opposing gripping element(s) may comprise a pair of opposing gripping pads configured for being linearly translated to actively advance the catheter body within the sheath body. Or, each pair of opposing gripping element(s) may comprise a pair of opposing rotatable gripping pads configured for being rotated opposite to each other to actively advance the catheter body within the sheath body. In either case, the feeder mechanism may be configured for actively advancing the catheter body within the sheath body at an infinite linear range.

The instrument driver further comprises at least one motor configured for translating the slidable carriage distally towards the sheath interface to translate the proximal catheter adapter towards the proximal sheath adapter while operating the feeder mechanism to actively advance the catheter body within the sheath body. In one embodiment, the motor(s) is configured for translating the slidable carriage distally away from sheath interface to translate the proximal catheter adapter away from the proximal sheath adapter while operating the feeder mechanism to actively retract the catheter body within the sheath body. The motor(s) may optionally be configured for operating each of the proximal sheath adapter and the proximal catheter adapter to respectively articulate distal ends of the sheath body and the catheter body. The instrument driver may further comprise a housing containing the motor(s).

In accordance with a third aspect of the present invention, an instrument driver for use with an elongated member (e.g., an elongated medical device, such as a steerable catheter and/or a balloon or stent delivery catheter) is provided. The instrument driver comprises a base, and a jaw assembly coupled to the base. The jaw assembly includes a first jaw having a gripping surface, and a second jaw having a gripping surface. Each of the first and second jaws may have a gripping pad having the gripping surface disposed thereon.

In one embodiment, the instrument driver may further comprise a housing containing the jaw assembly and the driver assembly.

The instrument driver further comprises a driver assembly operably coupled to the jaw assembly to advance the elongated member relative to the base by translating the first and second jaws toward each other, thereby closing the jaw assembly and gripping the elongated member between the respective gripping surfaces of the first and second jaws, translating the jaw assembly in a first axial direction when the jaw assembly is closed, translating the first and second jaws away from each other, thereby opening the jaw assembly and releasing the elongated member from between the respective gripping surfaces of the first and second jaws, and translating the jaw assembly in a second axial direction opposite to the first axial direction when the jaw assembly is opened.

In one embodiment, the driver assembly is configured for translating the jaw assembly in the first axial direction from a reference position when the jaw assembly is closed, and for translating the jaw assembly in the second axial direction back to the reference position when the jaw assembly is opened. The drive assembly may be configured for cyclically repeating the translation steps to repeatedly axially translate the elongate member relative to the base. In another embodiment, the driver assembly is operably coupled to the jaw assembly to retract the elongated member relative to the base by translating the first and second jaws toward each other, thereby closing the jaw assembly and gripping the elongated member between the respective gripping surfaces of the first and second jaws, translating the jaw assembly in the second axial direction when the jaw assembly is closed, translating the first and second jaws away from each other, thereby opening the jaw assembly and releasing the elongated member from between the respective gripping surfaces of the first and second jaws, and translating the jaw assembly in the first axial direction opposite to the first axial direction when the jaw assembly is opened.

In still another embodiment, the driver assembly may include a cam follower element including a first groove, a second groove, a first bearing surface, and a second bearing surface. The drive assembly may further include a cam shaft rotatably mounted to the base and operably coupled to the cam follower element. In this case, the cam shaft has a linear cam and first and second oppositely pitched helical cams, and is configured for being rotated relative to the base in a first rotational direction in a manner that engages the linear cam against the first bearing surface, thereby translating the gripping surface of the first jaw towards the gripping surface of the second jaw to close the jaw assembly, that engages the first helical cam within the first groove, thereby translating the jaw assembly in the first axial direction when the jaw assembly is closed, that engages the linear cam against the second bearing surface, thereby translating the gripping surface of the first jaw away from the gripping surface of the second jaw to open the jaw assembly, and that engages the second helical cam within the second groove, thereby translating the first jaw in the second axial direction opposite to the first axial direction when the jaw assembly is opened. The cross-sections of the first and second grooves may be V-shaped, and the first bearing surface and the second bearing surface may be circumferentially located on opposite sides of the cam shaft, and may have the same circumferential orientation on the cam shaft. The driver assembly may further include a motor configured for rotating the cam shaft relative to the base.

In an optional embodiment, the instrument driver comprises a plurality of jaw assemblies (e.g., three) coupled to the base, with each jaw assembly including a first jaw having a gripping surface, and a second jaw having a gripping surface. In this case, the driver assembly is operably coupled to each of the plurality of jaw assemblies to advance the elongated member relative to the base by translating the first and second jaws of the each jaw assembly toward each other, thereby closing the each jaw assembly and gripping the elongated member between the respective gripping surfaces of the first and second jaws of the each jaw assembly, translating the each jaw assembly in a first axial direction when the each jaw assembly is closed, translating the first and second jaws of the each jaw assembly away from each other, thereby opening the each jaw assembly and releasing the elongated member from between the respective gripping surfaces of the first and second jaws of the each jaw assembly, and translating the each jaw assembly in a second axial direction opposite to the first axial direction when the each jaw assembly is opened. Preferably, at least one the jaw assemblies is always closed during operation of the driver assembly, such that the elongated member is continuously translated in the first axial direction.

The instrument driver may be for use with a telescoping assembly comprising an outer elongated medical instrument and an inner elongated medical instrument. The outer medical instrument includes an outer elongated body and a proximal adapter affixed to the outer elongated body, and the inner medical instrument includes the aforementioned elongated member. In this case, the instrument driver comprises a housing on which the base is mounted; and an interface mounted to the housing and configured for being mated with the proximal adapter of the outer medical instrument. The inner elongated body is configured for being advanced within the outer elongated body when the jaw assembly is translated in the first axial direction. The inner medical instrument may further have a proximal adapter affixed to the elongated member, in which case, the instrument driver further comprises a slidable carriage to which the proximal adapter of the inner medical instrument is configured for being mated, and at least one motor configured for translating the slidable carriage distally towards the sheath interface to translate the proximal catheter adapter towards the proximal sheath adapter while operating the cam shaft to translate the jaw assembly in the first axial direction. The instrument driver may be a robotic instrument driver incorporated into a medical system comprising a master input device configured for receiving commands from a user, and a computer configured for controlling the robotic instrument driver in accordance with the user commands.

In accordance with a fourth aspect of the present inventions, another instrument driver for use with an elongated member (e.g., an elongated medical device, such as a steerable catheter and/or a balloon or stent delivery catheter) is provided. The instrument driver comprises a base and three jaw assemblies coupled to the base in an aligned manner. Each of the jaw assemblies includes a first jaw having a gripping surface, and a second jaw having a gripping surface. Each of the first and second jaws may have a gripping pad having the gripping surface disposed thereon. Each jaw assembly is configured for being alternately closed to grip the elongated member between the respective gripping surfaces of the first and second jaws, and opened to release the elongated member from between the respective gripping surfaces of the first and second jaws.

The instrument driver further comprises three cam follower elements operably coupled to the respective jaw assemblies. Each of the cam follower elements includes a first groove, a second groove, and a first bearing surface.

The instrument driver further comprises a cam shaft rotatably mounted to the base. The cam shaft has three sets of cams respectively associated with the three cam follower elements. Each set of cams includes a linear cam and first and second oppositely pitched helical cams. The cam shaft is configured for being rotated relative to the base in a first rotational direction in a manner that causes the three sets of cams to respectively actuate the three cam follower elements by, for each set of cams and associated cam follower element, engaging the linear cam against the first bearing surface, thereby translating the gripping surface of the first jaw towards the gripping surface of the second jaw to close the respective jaw assembly, engaging the first helical cam within the first groove, thereby translating the respective jaw assembly in a first axial direction when the respective jaw assembly is closed, and engaging the second helical cam within the second groove, thereby translating the first jaw in a second axial direction opposite to the first axial direction when the respective jaw assembly is opened. Each cam follower element may further have a second bearing surface, in which case, the cam shaft may be configured for being rotated in the first rotational direction in a manner that, for each set of cams and associated cam follower element, engages the linear cam against the second bearing surface, thereby translating the gripping surface of the first jaw away from the gripping surface of the second jaw to open the respective jaw assembly. The instrument driver may further comprise a motor configured for rotating the cam shaft relative to the base. The instrument driver may further comprise a housing containing the jaw assemblies, the cam follower elements, and the cam shaft.

In one embodiment, at least one the jaw assemblies is always closed when the cam shaft is rotated, such that the elongated member is continuously translated in the first axial direction during rotation of the cam shaft. In another embodiment, the set of cams are clocked one hundred twenty degrees from each other about the cam shaft. The cross-sections of the first and second grooves may be V-shaped, and the first bearing surface and the second bearing surface may be circumferentially located on opposite sides of the cam shaft, and may have the same circumferential orientation on the cam shaft.

The instrument driver may be for use with a telescoping assembly comprising an outer elongated medical instrument and an inner elongated medical instrument. The outer medical instrument includes an outer elongated body and a proximal adapter affixed to the outer elongated body, and the inner medical instrument includes the aforementioned elongated member. In this case, the instrument driver comprises a housing on which the base is mounted; and an interface mounted to the housing and configured for being mated with the proximal adapter of the outer medical instrument. The inner elongated body is configured for being advanced within the outer elongated body when the jaw assembly is translated in the first axial direction. The inner medical instrument may further have a proximal adapter affixed to the elongated member, in which case, the instrument driver further comprises a slidable carriage to which the proximal adapter of the inner medical instrument is configured for being mated, and at least one motor configured for translating the slidable carriage distally towards the sheath interface to translate the proximal catheter adapter towards the proximal sheath adapter while operating the cam shaft to translate the jaw assembly in the first axial direction. The instrument driver may be a robotic instrument driver incorporated into a medical system comprising a master input device configured for receiving commands from a user, and a computer configured for controlling the robotic instrument driver in accordance with the user commands.

In accordance with a fifth aspect of the present inventions, still another instrument driver for use with an elongated member (e.g., an elongated medical device, such as a steerable catheter and/or a balloon or stent delivery catheter). The instrument driver comprises a pair of opposing rotatable gripping pads. Each of the rotatable gripping pads includes an outer circular rim, a center hub, and a framework between the outer circular rim and the hub. The opposing rotatable gripping pads are configured for applying a gripping force to the elongated member, and the frameworks of the respective rotatable gripping pads are configured for partially collapsing in response to the gripping force, such that portions of the rims of the respective rotatable gripping pads flatten to contact each other.

In one embodiment, each of the frameworks includes a plurality of spokes extending between the center hub and the outer circular rim of the respective rotatable gripping pad. The spokes may be curved, such that they collapse onto each other in response to the gripping force, thereby flattening the portions of the rims of the respective rotatable gripping pads. The spokes may have a thickness in the range of 0.010-0.050 inches. The rim of each of the rotatable gripping pads may be composed of material having at least a 50 A durometer. Each of the rotatable gripping may have a diameter of two inches or less.

In one embodiment, the rim of each of the rotatable gripping pad has a concave gripping surface in order to facilitate vertical centering of the elongated member between the rotatable gripping pads. In another embodiment, each of the rotatable gripping pads includes a pair of opposing flat upper and lower surfaces, and a pair of upper and lower sprockets respectively disposed on the flat upper and lower surfaces. In this case, the upper and lower sprockets of one of the rotatable gripping pads are respectively configured for interlacing with the upper and lower sprockets of the other of the rotatable gripping pads to prevent the elongated member from slipping out between the rotatable gripping pad pads. One of the rotatable gripping pads may be configured for driving the other of the rotatable gripping pads via the interlacing of the upper and lower sprockets of the one rotatable gripping pad respectively with the upper and lower sprockets of the other rotatable gripping pad.

The instrument driver further comprises a pair of shafts affixed to the center hubs of the respective rotatable gripping pads, and a driver assembly configured for rotating at least one of the shafts, thereby causing the rotatable gripping pads to rotate in opposite directions to linearly translate the gripped elongated member between the rotatable gripping pads. The driver assembly may further comprise a drive train configured for being actuated to rotate at least one of the shafts, and a motor configured for actuating the drive train. In one optional embodiment, the pair of opposable arms comprises a pair of lower opposable arms, the driver assembly includes a lower pair of opposable arms, and the shafts are configured for mating with corresponding apertures in the respective lower arms, such that the lower arms respectively pivot with the upper arms in unison. The instrument driver may further comprise a housing containing the driver assembly.

In one optional embodiment, the instrument further comprises a pair of opposable arms on which the shafts are respectively rotatably disposed. One of the opposable arms may be configured for being pivoted in one direction to grip the elongated member between the rotatable gripping pads, and pivoted in a second opposite direction to release the elongated member from between the rotatable gripping pads. The driver assembly may further include a gripping force adjustment mechanism configured for being actuated to alternately pivot the one arm in the first direction and in the second opposite direction. The gripping force adjustment mechanism may include a compression spring configured for being varied to adjust the gripping force of the arms when gripping the elongated member. In this case, the gripping force adjustment mechanism may further include a rod associated with the compression spring and mechanically coupled to one of the arms. The rod may be configured for being alternately actuated to pivot the one arm in the first direction and in the second opposite direction.

The instrument driver may be for use with a telescoping assembly comprising an outer elongated medical instrument and an inner elongated medical instrument. The outer medical instrument includes an outer elongated body and a proximal adapter affixed to the outer elongated body, and the inner medical instrument includes the aforementioned elongated member. In this case, the instrument driver comprises a housing on which the base is mounted; and an interface mounted to the housing and configured for being mated with the proximal adapter of the outer medical instrument. The inner elongated body is configured for being advanced within the outer elongated body when the jaw assembly is translated in the first axial direction. The inner medical instrument may further have a proximal adapter affixed to the elongated member, in which case, the instrument driver further comprises a slidable carriage to which the proximal adapter of the inner medical instrument is configured for being mated, and at least one motor configured for translating the slidable carriage distally towards the sheath interface to translate the proximal catheter adapter towards the proximal sheath adapter while operating the cam shaft to translate the jaw assembly in the first axial direction. The instrument driver may be a robotic instrument driver incorporated into a medical system comprising a master input device configured for receiving commands from a user, and a computer configured for controlling the robotic instrument driver in accordance with the user commands.

In accordance with a sixth aspect of the present inventions, yet another instrument driver for use with an elongated member (e.g., an elongated medical device, such as a steerable catheter and/or a balloon or stent delivery catheter). The instrument driver comprises a pair of rotatable gripping pads configured for being rotated in opposite directions when the elongated member is gripped therebetween, and a pair of opposable arms on which the rotatable gripping pads are respectively rotatably disposed. The instrument driver may further comprise a gear assembly configured for being actuated to rotate the rotatable gripping pads in the opposite directions.

The instrument driver further comprises a first rod configured for being translated in opposite directions along its longitudinal axis to pivot one of the arms in a first rotational direction, such that the elongated member can be gripped between the rotatable gripping pads, and to pivot the one arm in a second rotational direction opposite to the first rotational direction, such that the elongated member can be released from between the rotatable gripping pads. The instrument driver may further comprise a motor configured for translating the first rod in the opposite directions along its longitudinal axis, and a housing containing the first rod, the spring, and the motor.

The instrument driver further comprises a compression spring associated with the first rod, wherein the compression of the spring is configured for being varied to adjust the translation of the first rod along the longitudinal axis, thereby adjusting the gripping force of the arms when gripping the elongated member. The compression of the spring may be proportional to the gripping force of the arms when gripping the elongated member. In one embodiment, the instrument driver further comprises a second rod mounted to the one arm, and a lever arm mounted between the first rod and the second rod, such that translation of the first rod in the opposite directions along its longitudinal axis rotates the lever arm, thereby rotating the second rod about its longitudinal axis to alternately pivot the one arm in the first and second rotational directions. Optionally, the instrument driver may further comprise a pair of section gears respectively coupled to the arms. The section gears engage each other, such that the other one of the arms pivots in a direction opposite to the direction in which the one arm pivots.

In one embodiment, the instrument driver further comprises a lead screw configured for being rotated about its longitudinal axis to linearly displace the first rod in the opposite directions along its longitudinal axis. In this case, the instrument driver may further comprise a lead nut having a first bore in which the lead screw is in threaded engagement, and a second bore in which the first rod is in bearing engagement, such that rotation of the lead screw about its longitudinal axis in opposite rotational directions respectively displaces the lead nut in opposite longitudinal directions to linearly displace the first rod respectively in the opposite directions along its longitudinal axis. The first rod may include a pair of annular flanges, in which case, the spring is disposed about the first rod between the annular flanges, and the lead nut is disposed between the spring and one of the annular flanges.

In another embodiment, the pair of opposable arms comprises a pair of lower opposable arms, and the instrument driver further comprises a base mounted to the housing, an upper pair of opposable arms pivotably mounted to the base, and a pair of shafts on which the rotatable gripping pads are respectively mounted. The shafts are rotatably mounted to the respective upper arms, and configured for mating with corresponding apertures in the respective lower arms, such that the lower arms respectively pivot with the upper arms pivot in unison. Optionally, one of the upper arms includes a bifurcated claw configured for vertically centered the elongated member between the rotatable gripping pads. The pair of lower arms may respectively include a pair of collars forming the corresponding apertures, and the instrument driver may comprise a sterile drape surrounding the housing. In this case, the sterile drape includes a pair of plugs respectively mated with the pair of collars, and the pair of shafts are respectively mated with the pair of plugs. The sterile drape may be configured for folding or collapsing between the plugs when the one arm pivots the arms in the first direction, and unfolding or expanding between the plugs when the one arm pivots the arms in the second direction. In this case, the sterile drape may include an expansion joint that facilitates the folding or collapsing of the sterile drape between the plugs, and that facilitates the unfolding or expansion of the sterile drape between the plugs.

The instrument driver may be for use with a telescoping assembly comprising an outer elongated medical instrument and an inner elongated medical instrument. The outer medical instrument includes an outer elongated body and a proximal adapter affixed to the outer elongated body, and the inner medical instrument includes the aforementioned elongated member. In this case, the instrument driver comprises a housing on which the base is mounted; and an interface mounted to the housing and configured for being mated with the proximal adapter of the outer medical instrument. The inner elongated body is configured for being advanced within the outer elongated body when the jaw assembly is translated in the first axial direction. The inner medical instrument may further have a proximal adapter affixed to the elongated member, in which case, the instrument driver further comprises a slidable carriage to which the proximal adapter of the inner medical instrument is configured for being mated, and at least one motor configured for translating the slidable carriage distally towards the sheath interface to translate the proximal catheter adapter towards the proximal sheath adapter while operating the cam shaft to translate the jaw assembly in the first axial direction. The instrument driver may be a robotic instrument driver incorporated into a medical system comprising a master input device configured for receiving commands from a user, and a computer configured for controlling the robotic instrument driver in accordance with the user commands.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of various embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 25a-25g are plan views illustrating an exemplary sequence used by the catheter feeder of FIG. 6 to open, close, and translate one jaw assembly of the jaw assembly arrangement FIG. 11 to advance/retract the leader catheter within the guide sheath of the catheter assembly of FIG. 4;

DETAILED DESCRIPTION OF THE ILLUSTRATED EMBODIMENTS

Figure 1:
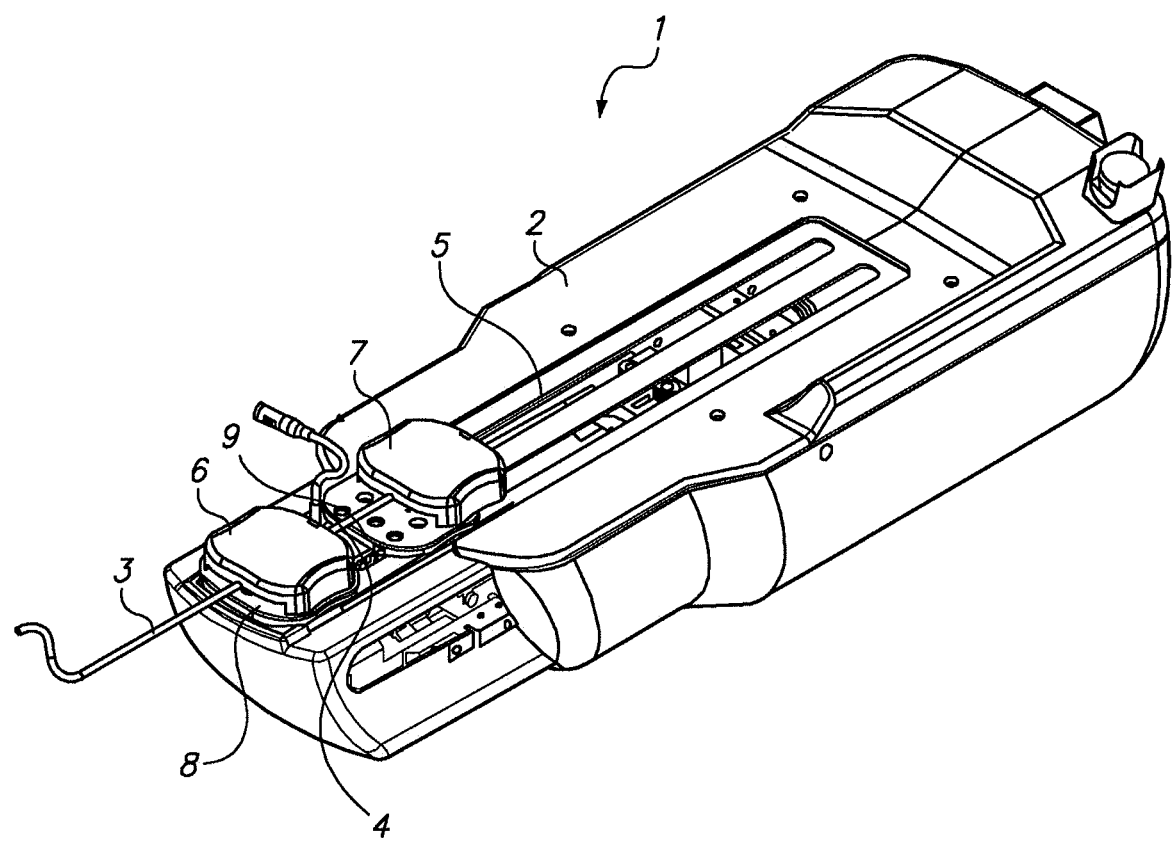
FIG. 1 is a perspective view of a prior art instrument driver for use within medical robotic system.
Figure 2:
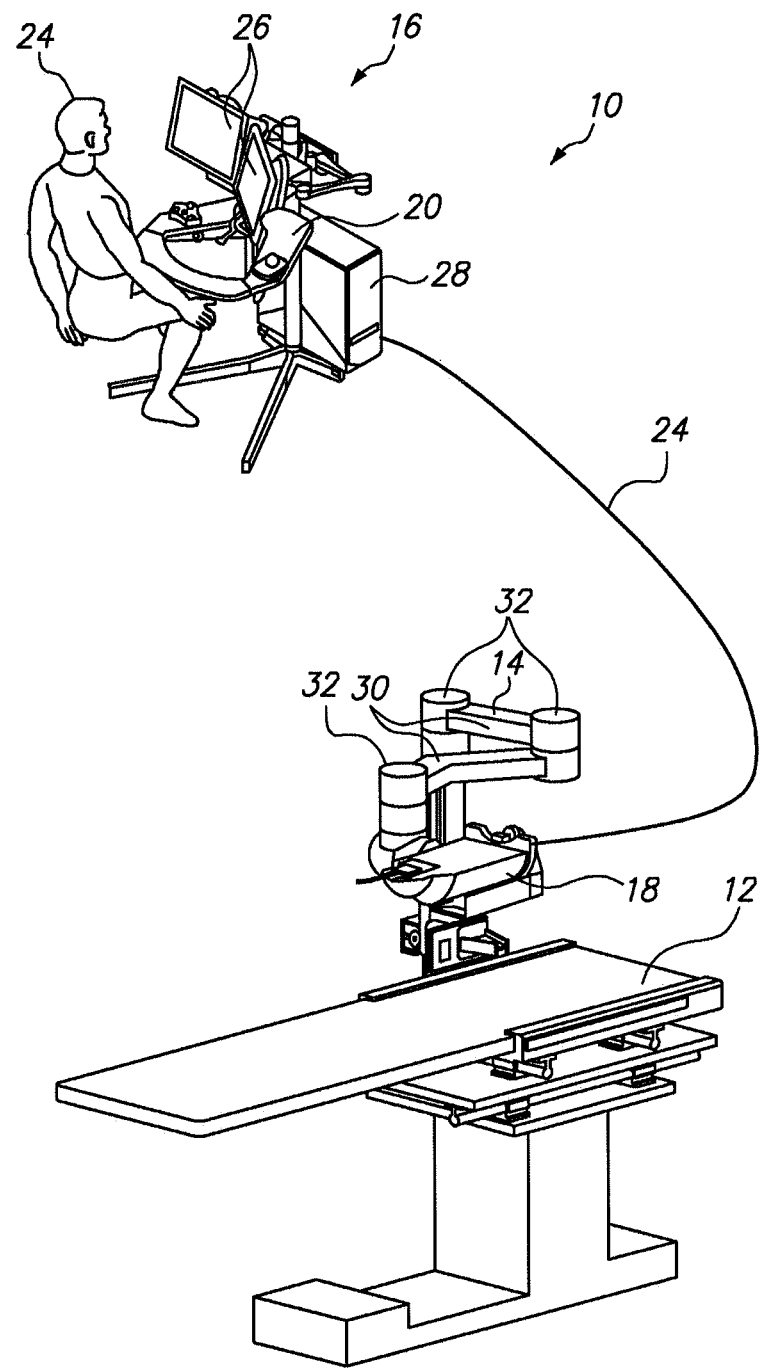
FIG. 2 is a perspective view of a medical robotic system constructed in accordance with one embodiment of the present inventions.

Referring to FIG. 2, one embodiment of a robotic catheter system 10 constructed in accordance with the present invention will now be described. The system 10 generally comprises an operating table 12 having a movable support-arm assembly 14, an operator control station 16 located remotely from the operating table 12, and a robotic catheter assembly 18 mounted to the support-arm assembly 14 above the operating table 12. Exemplary robotic catheter systems that may be modified for constructing and using embodiments of the present invention are disclosed in detail in the following U.S. patent applications, which are all expressly incorporated herein by reference in their entirety: U.S. patent application Ser. No. 11/678,001, filed Feb. 22, 2007; U.S. patent application Ser. No. 11/073,363, filed Mar. 4, 2005; U.S. patent application Ser. No. 11/179,007, filed Jul. 6, 2005; U.S. patent application Ser. No. 11/418,398, filed May 3, 2006; U.S. patent application Ser. No. 11/481,433, filed Jul. 3, 2006; U.S. patent application Ser. No. 11/637,951, filed Dec. 11, 2006; U.S. patent application Ser. No. 11/640,099, filed Dec. 14, 2006; U.S. Patent Application Ser. No. 60/833,624, filed Jul. 26, 2006; and U.S. Patent Application Ser. No. 60/835,592, filed Aug. 3, 2006.

The control station 16 comprises a master input device 20 that is operatively connected to the robotic catheter assembly 18. A physician or other user 22 may interact with the master input device 20 to operate the robotic catheter assembly 18 in a master-slave arrangement. The master input device 20 is connected to the robotic catheter assembly 18 via a cable 24 or the like, thereby providing one or more communication links capable of transferring signals between the control station 16 and the robotic catheter assembly 18. Alternatively, the master input device 20 may be located in a geographically remote location and communication is accomplished, at least in part, over a wide area network such as the Internet. The master input device 20 may also be connected to the robotic catheter assembly 18 via a local area network or even wireless network that is not located at a geographically remote location.

The control station 16 also comprises one or more monitors 26 used to display various aspects of the robotic instrument system 10. For example, an image of the guide sheath, leader catheter, and guidewire (described in further detail below) may be displayed in real time on the monitors 26 to provide the physician 22 with the current orientation of the various devices as they are positioned, for example, within a body lumen or region of interest. The control station 16 further comprises a processor in the form of a computer 28, which may comprise a personal computer or other type of computer work station for accurately coordinating and controlling actuations of various motors within robotic catheter assembly 18.

The support-arm assembly 14 is configured for movably supporting the robotic catheter assembly 18 above the operating table 12 to provide convenient access to the desired portions of the patient (not shown) and provide a means to lock the catheter assembly 18 into position subsequent to the preferred placement. In this embodiment, the support-arm assembly 14 comprises a series of rigid links 30 coupled by electronically braked joints 32, which prevent joint motion when unpowered, and allow joint motion when energized by the control station 16. In an alternative embodiment, the rigid links 30 may be coupled by more conventional mechanically lockable joints, which may be locked and unlocked manually using, for example, locking pins, screws, or clamps. The rigid links 30 preferably comprise a light but strong material, such as high-gage aluminum, shaped to withstand the stresses and strains associated with precisely maintaining three-dimensional position of the weight of the catheter assembly 18.

Figure 3:
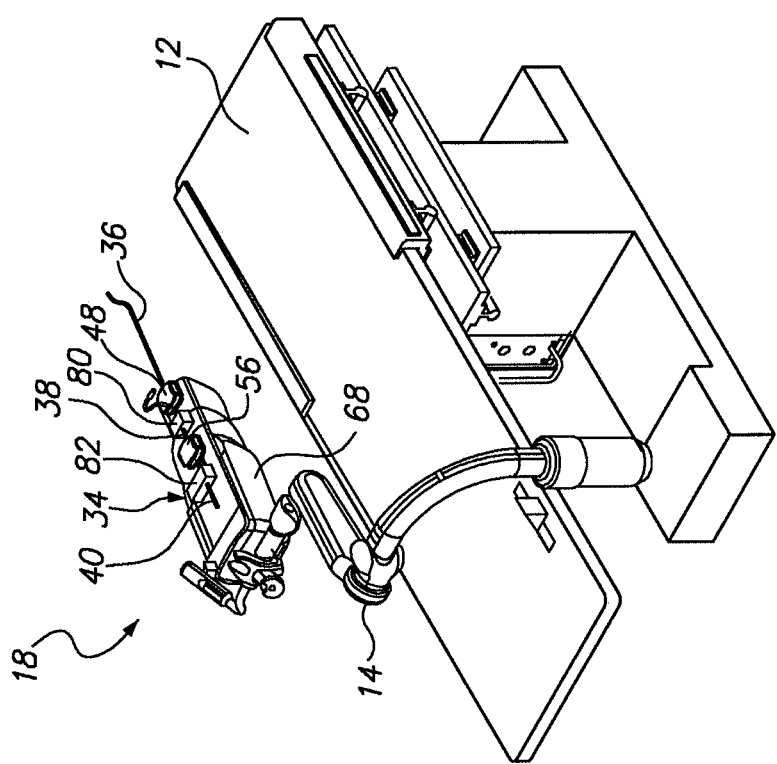
FIG. 3 is a perspective view of a robotic catheter assembly used in the medical robotic system of FIG. 2.
Figure 4:
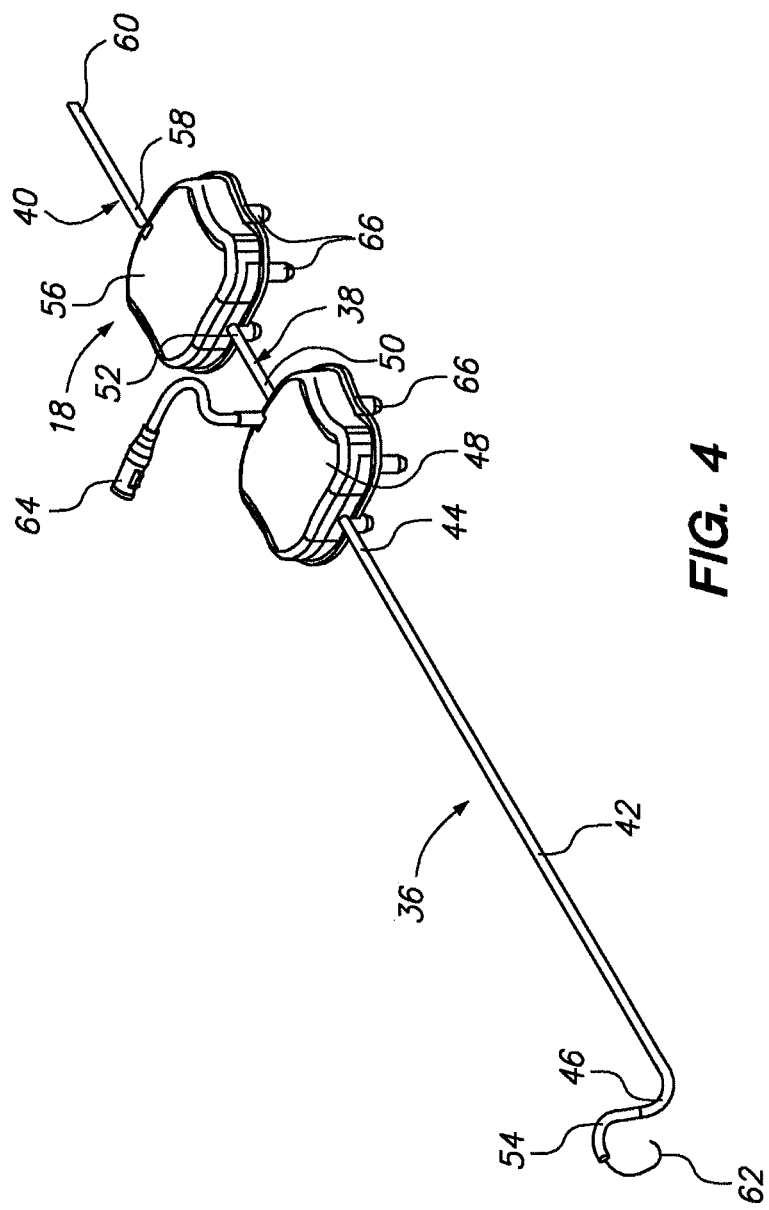
FIG. 4 is a perspective view of the catheter assembly used in the robotic catheter assembly of FIG. 3.
Figure 5:
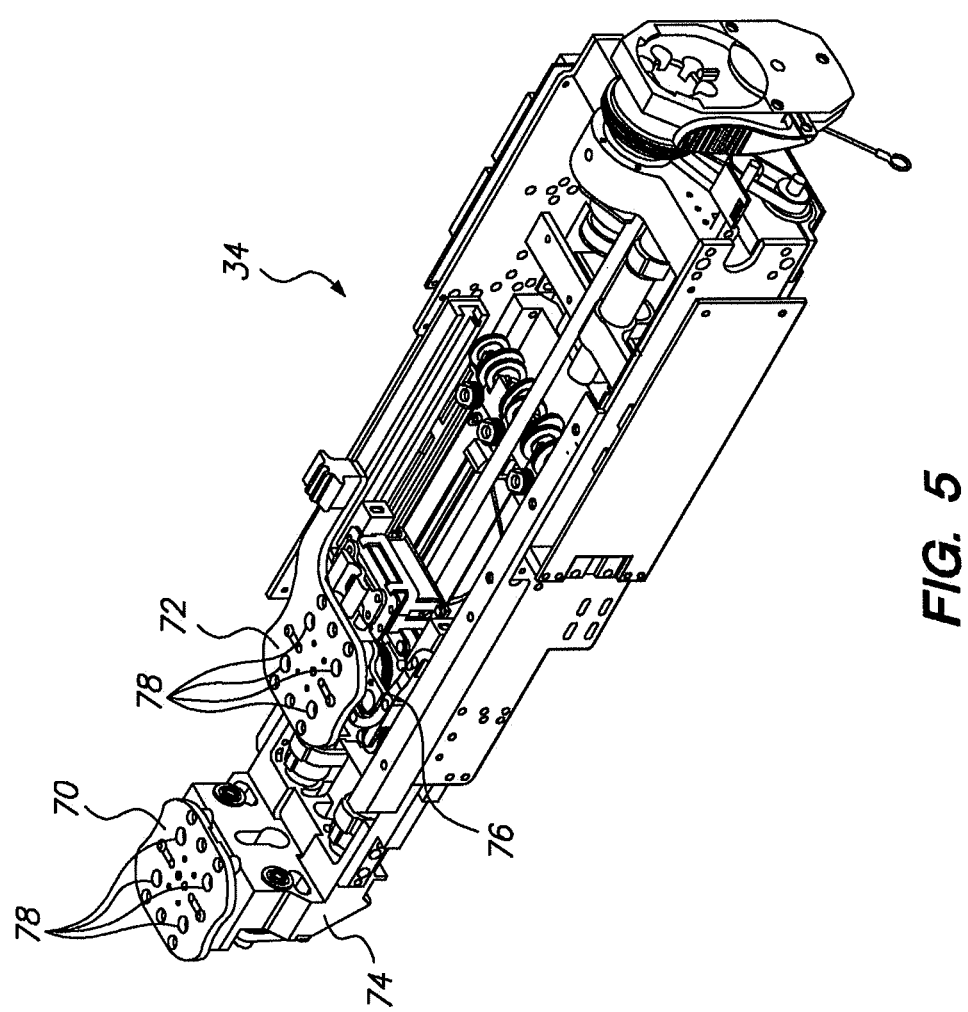
FIG. 5 is a perspective view of an instrument driver used in the robotic catheter assembly of FIG. 4.

Referring further to FIGS. 3 and 4, the robotic catheter assembly 18 will now be described in detail. The robotic catheter assembly 18 comprises a robotic instrument driver 34, a robotic guide sheath 36, a robotic leader catheter 38, and a conventional guidewire 40 mounted to the instrument driver 34 in a coaxial and telescoping relationship. The robotic catheter assembly 18 may also include a drape (not shown) that covers the non-disposable portion of the instrument driver 34. As will be described in further detail below, the instrument driver 34 provides robotic steering and advancement/retraction actuation to the guide sheath 36 and leader catheter 38, and robotic advancement/retraction and roll actuation to the guidewire 40, in accordance with control signals transmitted from the control station 16 (shown in FIG. 2). The guide sheath 36 generally includes a sheath body 42 having a proximal end 44 and a distal end 46, as well as a proximal interface in the form of a guide sheath steering adapter 48 ("splayer") operably coupled to the proximal end 44 of the sheath body 42. The leader catheter 38 generally includes a catheter body 50 having a proximal end 52 and a distal end 54, as well as a proximal interface in the form of a leader catheter steering adapter 56 ("splayer") operably mounted to the proximal end 52 of the catheter body 50. In an alternative embodiment, rather than a leader catheter 38, a microcatheter (not shown) may be used instead. The guidewire 40 generally includes a guidewire body 58 having a proximal end 60 and a distal end 62. The proximal sheath adapter 48 may optionally comprises an active valve 64 for providing a means for purging the working lumen of the guide sheath 36.

Each of the adapters 48, 56 also comprises one or more drive shafts 66 with corresponding spools or drums (not shown) that can selectively tension or release pullwires (not shown) disposed within the respective sheath body 42 and catheter body 50, thereby effecting a single articulation (and optionally, multiple articulations) of the distal ends 46, 54 of the sheath and catheter bodies 42, 50. In the illustrated embodiment, each of the adapters 48, 56 comprises four rotating drive shafts 66 (only one shown for the proximal sheath adapter 48, and only three shown for the proximal adapter 56) for four corresponding pullwires. In this case, the distal ends 46, 54 of the sheath and catheter bodies 42, 50 may be articulated in an infinite amount of directions. In the case where a microcatheter is used in place of the leader catheter 38, it may include a proximal adapter capable of inserting, retracting and rolling its distal end.

The guide sheath 36 comprises a working lumen (not shown) that extends all the way through the sheath body 42. The geometry and size of the working lumen will be selected in accordance with the cross-sectional geometry and size of the lead catheter 38. The sheath body 42 may be composed of a low-friction inner layer (e.g., a coating of silicone or polytetrafluoroethylene) to provide a low-friction surface to accommodate movement of the leader catheter 38 within the working lumen. The leader catheter 38 passes through the lumen of the guide sheath 36, and is thus, moveable relative thereto. As shown in FIGS. 3 and 4, the leader catheter 38 projects distally with respect to the distal end 46 of the sheath body 42. Of course, the leader catheter 38 may be withdrawn proximally such that its distal end 54 is substantially flush with the distal end 46 of the sheath body 42, or withdrawn proximally even further such that its distal end 54 is disposed within the distal end 46 of the sheath body 42. The leader catheter 38 may be movably positioned within the working lumen of the guide sheath 36 to enable relative advancement/retraction of the leader catheter 38 within the guide sheath 36, and relative steering or bending of the two devices relative to each other, particularly when the distal end 54 of the leader catheter 38 is advanced beyond the distal tip of the guide sheath 36.

Similarly, the leader catheter 38 comprises a working lumen (not shown) that extends at least partially through the catheter body 50. The geometry and size of the working lumen will be selected in accordance with the cross-sectional geometry and size of the guidewire 40. The catheter body 50 may be composed of a low-friction inner layer (e.g., a coating of silicone or polytetrafluoroethylene) to provide a low-friction surface to accommodate movement of the guidewire 40 within the working lumen. The guidewire 40 passes through the lumen of the leader catheter 38, and is thus, moveable relative thereto. As shown in FIGS. 3 and 4, the guidewire 40 projects distally with respect to the distal end 54 of the catheter body 50. Of course, the guidewire 40 may be withdrawn proximally such that its distal end 62 is substantially flush with the distal end 54 of the catheter body 50, or withdrawn proximally even further such that its distal end 62 is disposed within the distal end 54 of the catheter body 50. The guidewire 40 may be movably positioned within the working lumen of the leader catheter 38 to enable advancement/retraction and rotation or "roll" of the guidewire 40 within the leader catheter 38. Notably, by movably positioning the guidewire 40 relative to the leader catheter 38, and movably positioning the leader catheter 38 relative to the guide sheath 36, the bending stiffness of the assembly may be varied as needed to optimize the tracking ability of the leader catheter 38.

The instrument driver 34 comprises a housing 68 that contains motors and drive mechanisms (not shown in FIGS. 3 and 4). The respective adapters 48, 56 are mechanically interfaced to the housing 68 in such a manner that they may be axially translated relative to each other via operation of the motors, thereby effecting advancement or retraction movements of the respective guide sheath 36 and leader catheter 38 relative to each other, and thus, relative to the operating table 12 (shown in FIG. 2). In particular, the respective proximal adapters 48, 56 are removably mounted to respective mounting plates 70, 72, which in turn, are respectively affixed to an interface in the form of a sheath drive block 74 and a catheter carriage 76. In the illustrated embodiment, the proximal adapters 48, 56 are disposable units, and thus, can be located on a similarly disposable sterile adapter (not shown) into which the mounting plates 70, 72 are built. The sterile adapter can be disposed over the sterile drape of the housing 68, and once the medical procedure is completed, removed along with the other disposable units from the sterile housing 68. Each of the mounting plates 70, 72 includes four openings 78 for receiving the four corresponding drive shafts 66 of the respective proximal adapters 48, 56. The drive shafts 66 are coupled to drive assemblies (not shown) contained within the housing 68 for selectively rotating the drive shafts 66, and thereby, selectively tensioning the corresponding pull wires to articulate the distal ends 46, 54 of the sheath and catheter bodies 42, 50.

The instrument driver 34 may include a lead screw mechanism (not shown) coupled between one of the motors and the catheter carriage 76 for driving the carriage 76 distally and proximally to perform the insertion/retraction actuations of the leader catheter 38. The entire robotic catheter assembly 18 can be moved relative to the support-arm assembly 14 to provide insertion/retraction actuation for the guide sheath 36. In an alternative embodiment, the proximal sheath adapter 48 of the guide sheath 36 is mounted to a sheath carriage (not shown) via mounting plate 70. In this case, the instrument driver 34 may include two independently-actuated lead screw mechanisms (not shown) respectively coupled between motors contained in the housing 68 and the carriages for independently driving the carriages distally and proximally to perform the insertion/retraction actuations of the guide sheath 36 and leader catheter 38.

Significantly, the instrument driver 34 comprises an active catheter feeder 80 that actively advances the leader catheter 38 within the guide sheath 36 and actively retracts the leader catheter 38 within the guide sheath 36 in coordination with the translation of the catheter carriage 76. That is, during a robotic advancement/retraction action of the leader catheter 38, the active catheter feeder 80 simultaneously advances the leader catheter 38 into the guide sheath 36 at the same speed at which the catheter carriage 76 is translated towards the sheath drive block 74, thereby preventing the axial buckling of the leader catheter 38 between the sheath drive block 74 and catheter carriage 76, and simultaneously retracts the leader catheter 38 within the guide sheath 36 at the same speed at which the catheter carriage 76 is translated away from the sheath drive block 74. Alternatively, if the leader catheter 38 is longer than the guide sheath 36 by a distance that is greater than the maximum distance between the sheath drive block 74 and the catheter carriage 76, the active catheter feeder 80 may advance the leader catheter 38 at a higher speed than the catheter carriage 76 moves, thereby allowing the leader catheter 38 to be inserted further than what is achievable without the active catheter feeder 80.

To maximize its non-buckling effect, the active catheter feeder 80 preferably resides as close as possible to the proximal sheath adapter 48 where the leader catheter 38 enters the guide sheath 36. In the alternative case where the proximal sheath adapter 48 is mounted to a separate carriage, the active catheter feeder 80 is preferably mounted to this carriage, such that it moves with the proximal sheath adapter 48 in order to maintain the close proximity between the active catheter feeder 80 and the proximal sheath adapter 48. Thus, in both cases, the active catheter feeder 80 is affixed relative to the sheath interface (sheath drive block 74 or sheath carriage). The external portion of the active catheter feeder 80, as a disposable unit, can all be conveniently located on the mounting plate 70 on which the proximal adapter 48 is located. The catheter feeder 80 may be self-contained or may be integrated into the housing 68 of the instrument driver 34.

To maximize the range of the translation of the catheter carriage 76 (the "stroke") toward the sheath drive block 74, the length of the active catheter feeder 80 is minimized (e.g., less than 6 inches). It is also preferable that the active catheter feeder 80 apply pressure to the leader catheter 38 in a manner that firmly grips the leader catheter 38 in a manner that prevents slippage of the leader catheter 38 (even if the leader catheter 38 is hydrophilic and wet), without pinching the leader catheter 38 in a manner that might otherwise collapse the lumen of the leader catheter 38 and prevent or hinder movement of the guidewire 40 within the leader catheter 38, or in the case where working catheters, such as stent/balloon catheters, are actively advanced/retracted within the guide sheath 36, minimally affects the injection during deployment of the stent or balloon. The active catheter feeder 80 preferably retains this capability for a range of catheter diameters. For example, the active catheter feeder 80 should be operable with a 6 F leader catheter, but also microcatheter in the range of 2.5-3 F or bigger catheters up to 12 Fr.

The active catheter feeder 80 preferably allows top loading of the leader catheter 38 to provide an efficient and quick means of installing the leader catheter 38 onto the instrument driver 34. The active catheter feeder 80 also preferably provides for infinite advancement/retraction range of actuation; that is, the active catheter feeder 80 is capable of continually advancing/retracting an infinite length of the leader catheter 38. In such cases, the active catheter feeder 80 feeds the leader catheter 38 at a much higher rate of motion than the catheter carriage 76 advancement. The exact relationship between how much the leader catheter 38 is advanced into the guide sheath 74 by the active catheter feeder 80 and how much the catheter carriage 76 moves can be adjusted and controlled for each catheter type and length.

The instrument driver 34 further comprises a guidewire feeder 82 mounted to the catheter carriage 76 and to which the proximal end 60 of the guidewire body 58 is affixed. The distal end 62 of the guidewire body 58 may have a J-shape or may be straight as is conventional for guidewires. Each of the adapters 48, 56 and guidewire driver 68 may optionally be capable of rotating or rolling the sheath body 42, catheter body 50, and guidewire body 58 relative to each other.

Referring to FIG. 6-26, one embodiment of an active catheter feeder 100 will now be described. The catheter feeder 100 is designed to mimic the manual finger feed method that physicians may use to advance/retract the leader catheter 38 within the guide sheath 36, and in particular, the grip, push, release, retracting, and repeating movements performed by the fingers of the physician to incrementally advance the leader catheter 38, and the grip, pull, release, advancing, and repeating movements performed by the fingers of the physician to incrementally retract the leader catheter 38. In the illustrated embodiment, the catheter feeder 100 is mounted to the outside of the housing 68 between the sheath drive block 74 and the catheter carriage 76.

Figure 6:
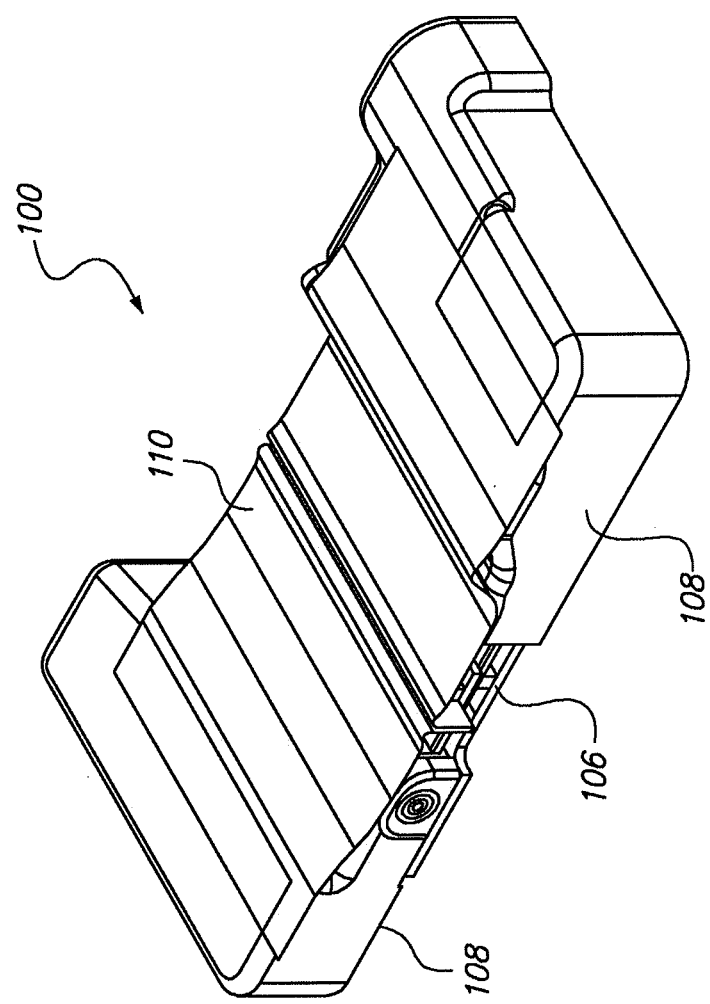
FIG. 6 a perspective view of one embodiment of a catheter feeder that can be used in the instrument driver of FIG. 5.
Figure 7:
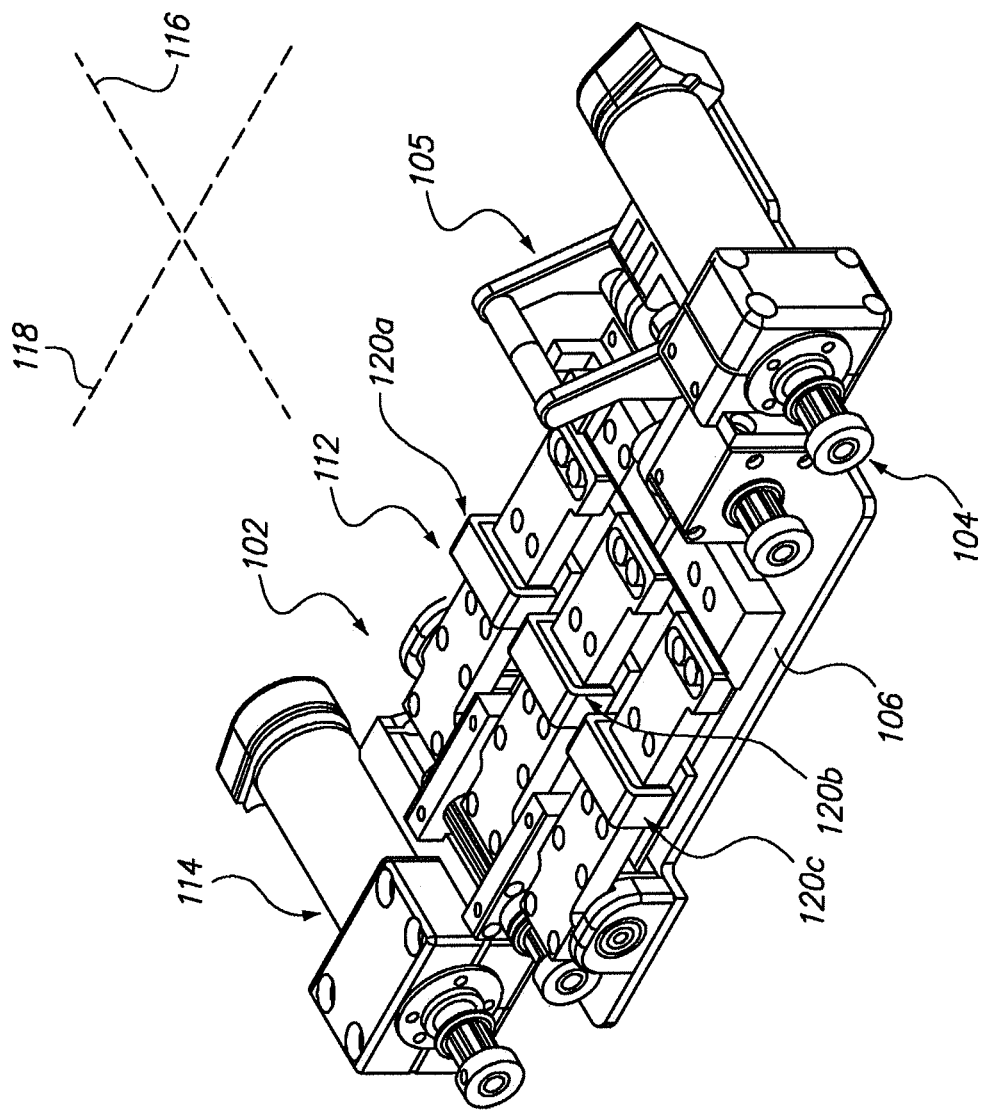
FIG. 7 is a perspective view of the catheter feeder of FIG. 6, wherein the housing has been removed.
Figure 8:
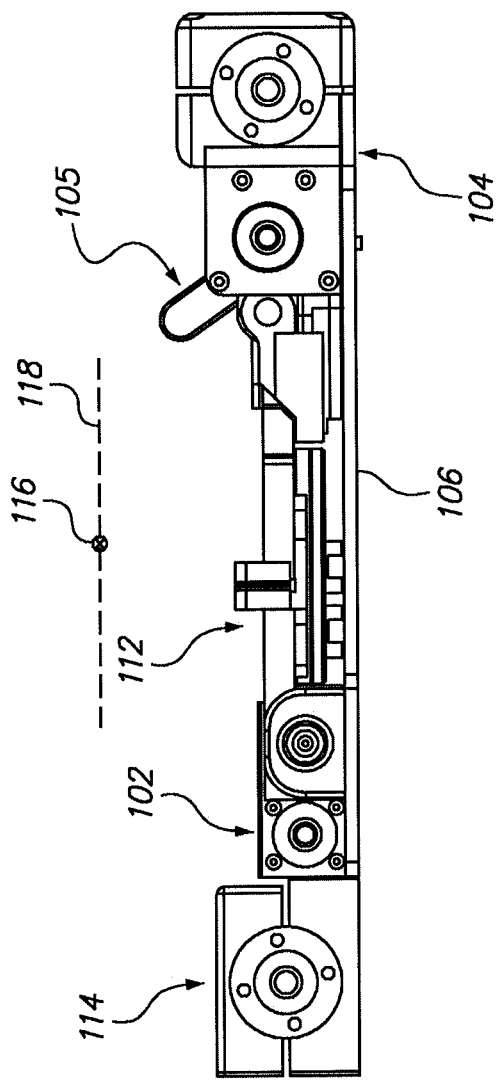
FIG. 8 is a side view of the catheter feeder of FIG. 6, wherein the housing has been removed.

To this end, and with particular reference to FIGS. 6-8, the catheter feeder 100 generally comprises a feeder assembly 102 configured for advancing/retracting the leader catheter 38 within the guide sheath 36, a grip adjustment assembly 104 configured for adjusting the grip of the feeder assembly 102, a loading/unloading assembly 105 configured for allowing the leader catheter 38 to be top-loaded and unloaded from the active catheter feeder 100, a base plate 106 on which the feeder assembly 102 and grip adjustment assembly 104 are mounted, a housing 108 mounted to the base plate 106 over the feeder assembly 102 and grip adjustment assembly 104, and a drape 110 configured for isolating the disposable components of the catheter feeder 100 from the sterile field.

The feeder assembly 102 generally comprises a jaw assembly arrangement 112 configured for performing advancing/retracting movements of the leader catheter 38, and a driver assembly 114 configured for actuating the jaw assembly arrangement 112 to perform these movements.

Figure 9:
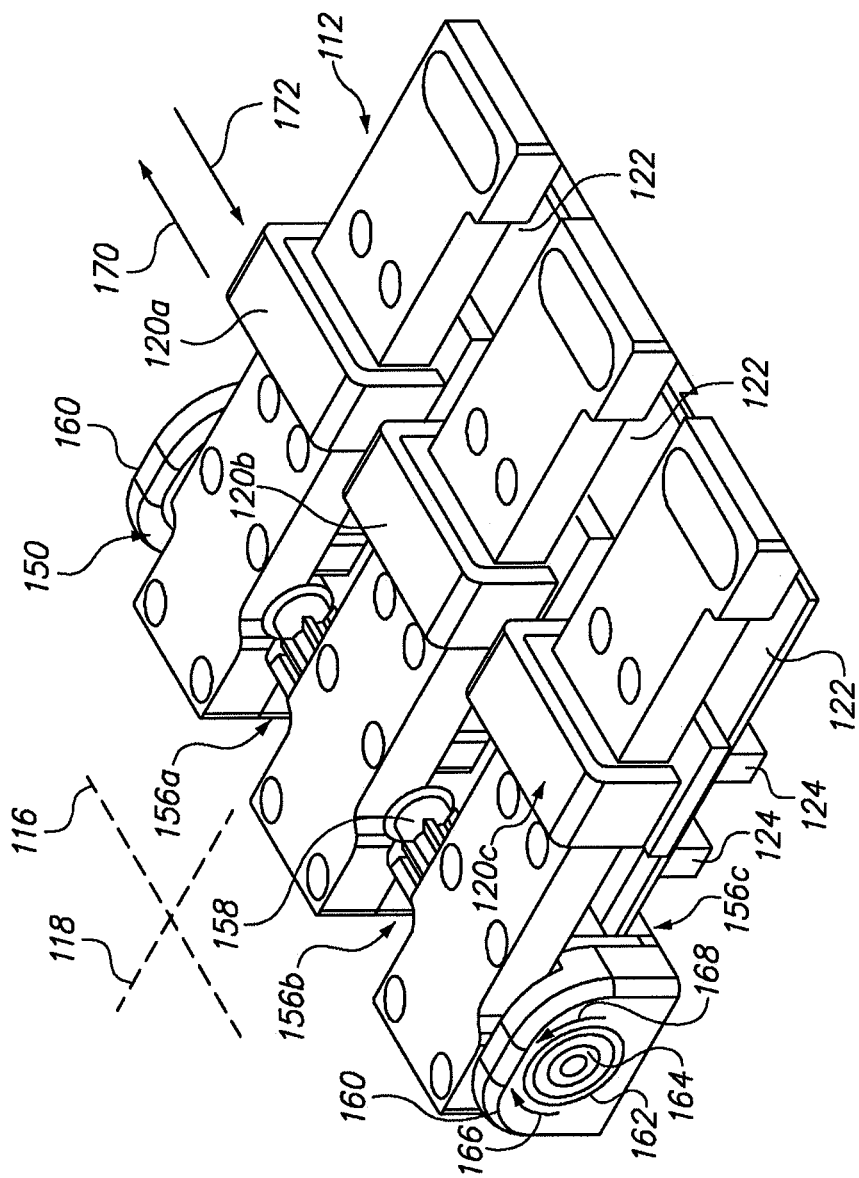
FIG. 9 is a top perspective view of a jaw assembly arrangement and cam assembly used in the catheter feeder of FIG. 6.
Figure 10:
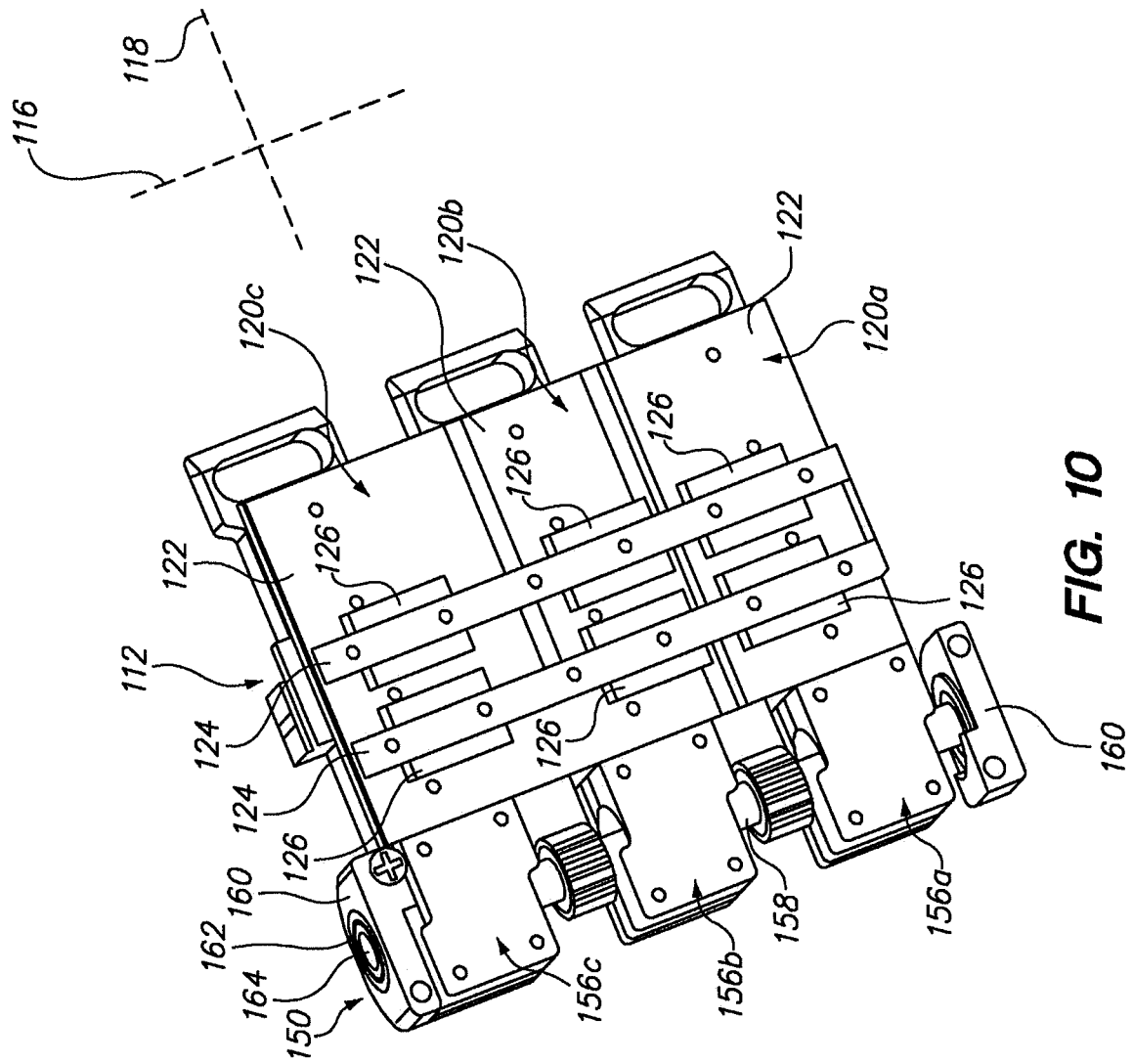
FIG. 10 is a bottom perspective view of the jaw assembly arrangement and cam assembly shown in FIG. 9.
Figure 11:
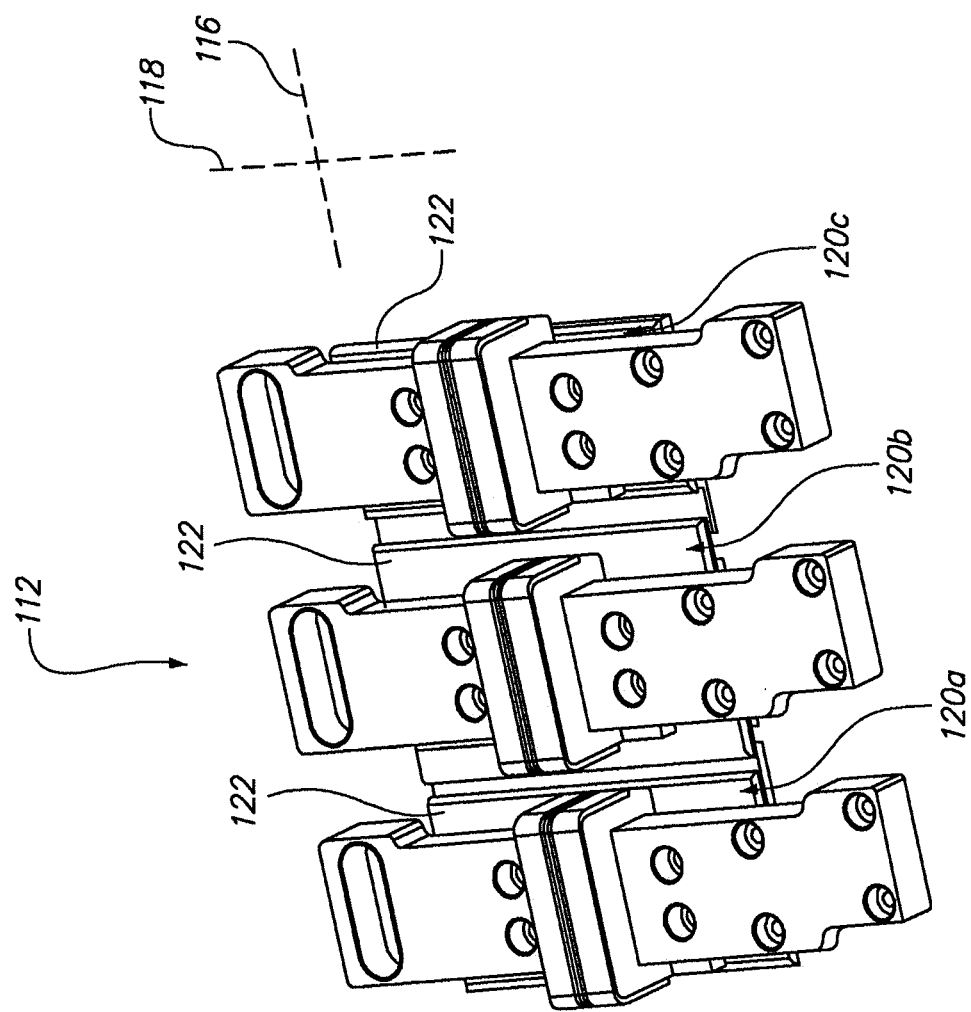
FIG. 11 is a perspective view of the jaw assembly arrangement shown in FIG. 6.

Referring further to FIGS. 9-11, the jaw assembly arrangement 112 includes three jaw assemblies 120a, 120b, 120c configured for being independently translated relative to the base plate 106 parallel to a longitudinal axis 116 in a reciprocal manner. To this end, the jaw assemblies 120 respectively include base plates 122 that are slidably engaged with each other in a nested arrangement. In order to guide independent translation of the jaw assemblies 120 along the longitudinal axis 116, the jaw assembly arrangement 112 further includes a parallel pair of rails 124 mounted to the base plate 106 along the longitudinal axis 116, and each jaw assembly 112 includes a pair of channeled blocks 126 mounted to the respective base plate 122 for slidably receiving the pair of rails 124 therein, as best shown in FIG. 10.

Figure 12:
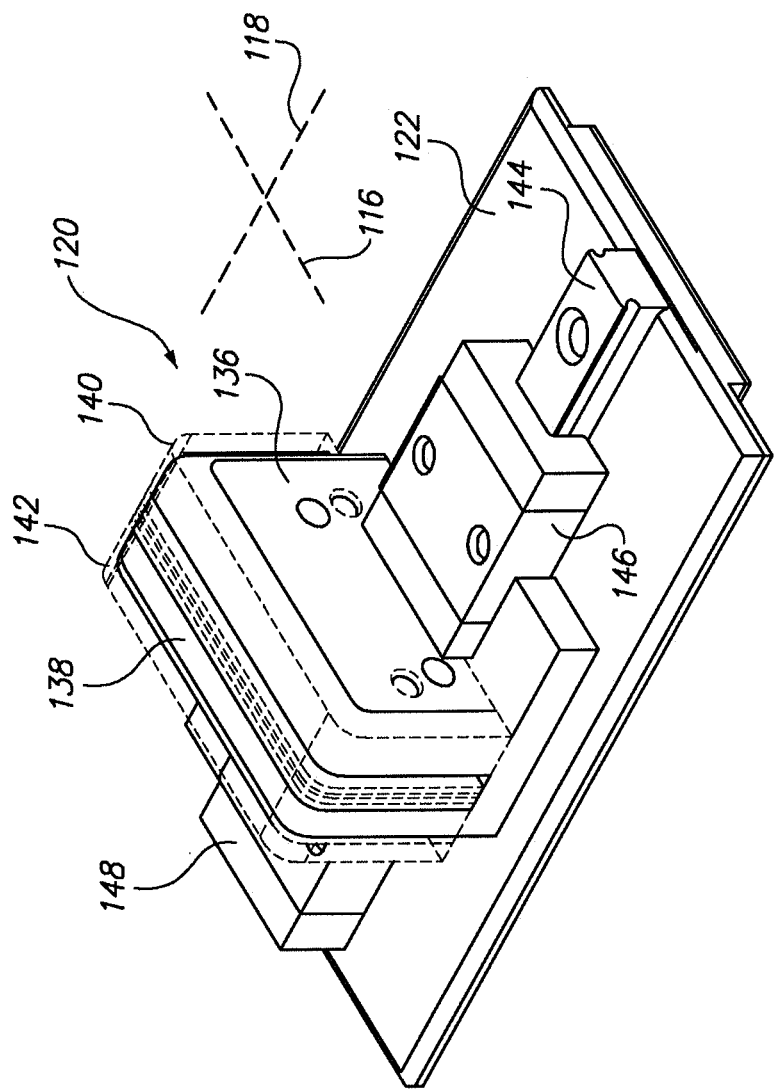
FIG. 12 is a perspective view of a jaw assembly used in the jaw assembly arrangement of FIG. 11.
Figure 13:
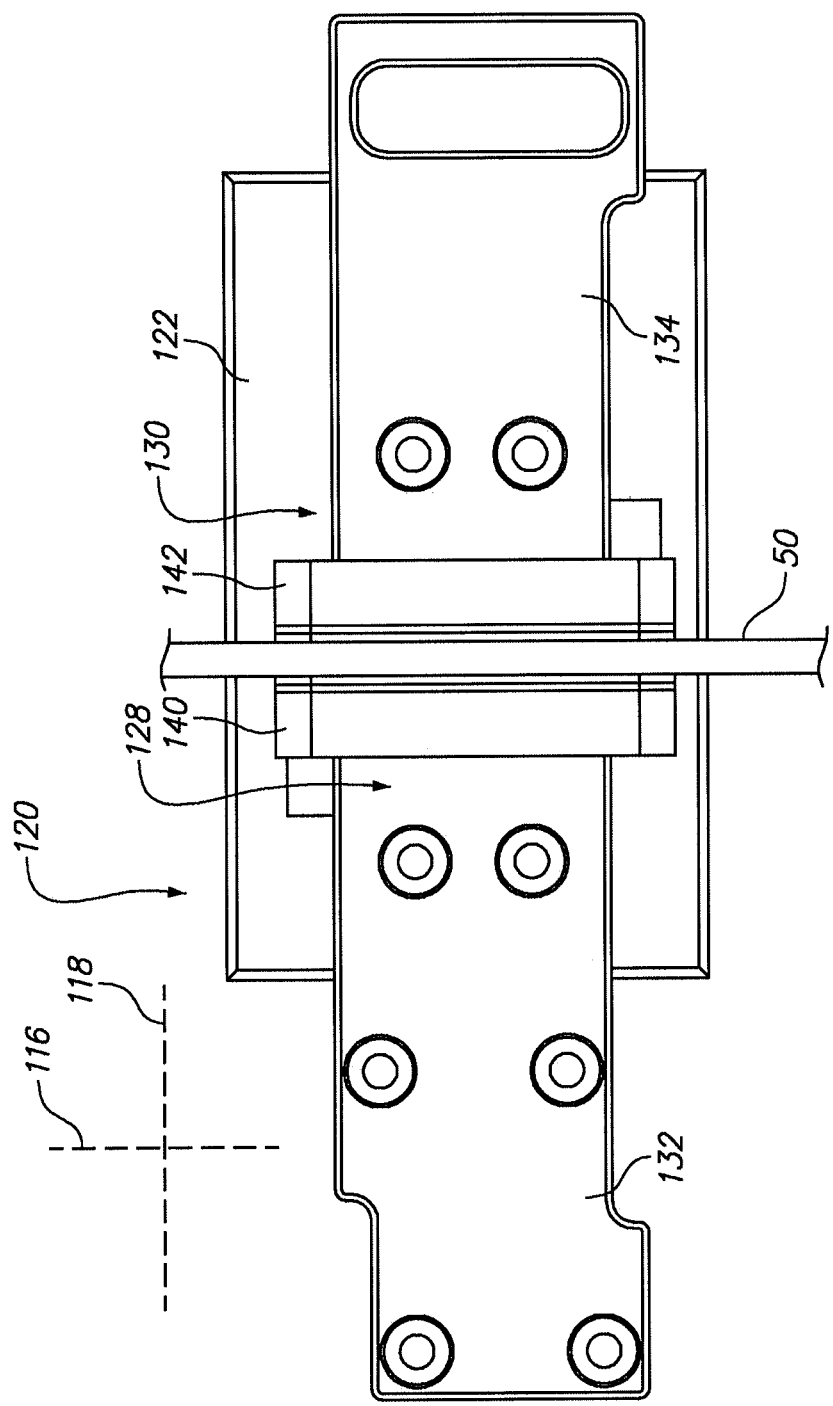
FIG. 13 is top view of a jaw assembly used in the jaw assembly arrangement of FIG. 11, particularly shown in a closed state.
Figure 14:
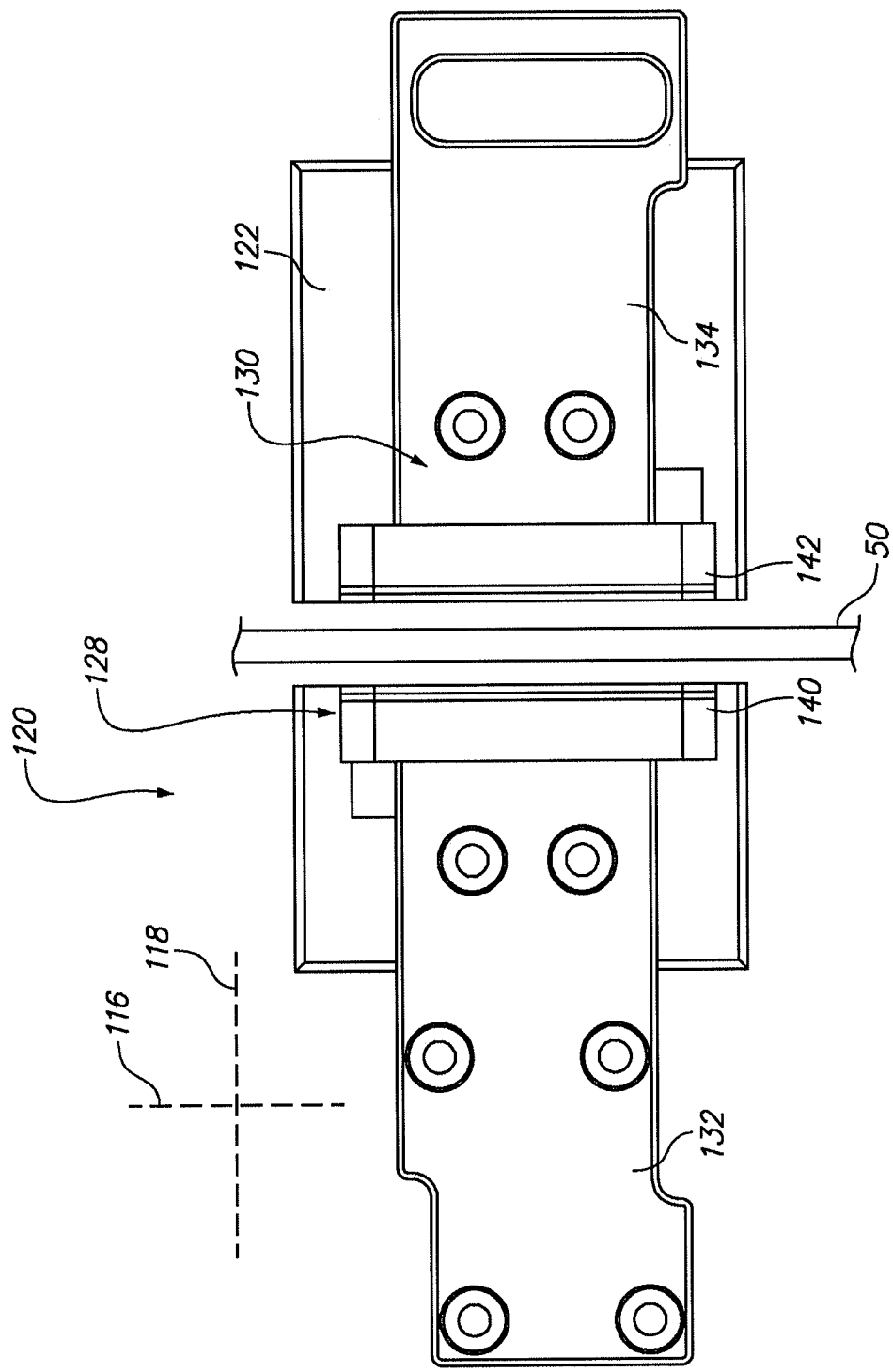
FIG. 14 is top view of the jaw assembly of FIG. 13, particularly shown in an open state.

Referring specifically to FIGS. 12-14, each jaw assembly 120 comprises a first jaw 128 having a jaw actuator 132 (not shown in FIG. 12), a gripping flange 136 affixed to the jaw actuator 132, and a gripping pad 140 (shown in phantom in FIG. 12) mounted to the gripping flange 136, and a second jaw 130 having a jaw actuator 134 (not shown in FIG. 12), a gripping flange 138 affixed to the jaw actuator 134, and a gripping pad 142 (shown in phantom in FIG. 12) mounted to the gripping flange 138. The jaw assembly 120 is configured for being alternately closed (FIG. 13) to grip the catheter body 50 between the respective gripping pads 140, 142 of the first and second jaws 128, 130, and opened (FIG. 14) to release the catheter body 50 from between the respective gripping pads 140, 142 of the first and second jaws 128, 130. For the purposes of this specification, a jaw assembly is closed at the point where the gripping pads 140, 142 are closest to each other, and is open at the point where the gripping pads 140, 142 are furthest from each other (after the second jaws 130 are adjusted to a fixed position by the grip adjustment assembly 104, as will be described in further detail below). The jaw assembly 120 is designed in a manner that the catheter body 50 is only gripped when the jaw assembly 120 is in the closed position, and the catheter body 50 is released when the jaw assembly 120 is in the opened position or transitioning between the closed position and the opened position.

Notably, the gripping pads 140, 142 inherently have gripping surfaces that distribute the gripping force applied to the catheter body 50, thereby preventing pinching. As such, a relatively large gripping force can be applied to the catheter body 50 to prevent slippage, as well as to compensate for varying catheter diameters. Furthermore, as will be discussed in further detail below, the grip adjustment assembly 104 can be operated to adjust the strength that the jaw assembly 104 grips the catheter body 50 between the gripping pads 140, 142.

The major surfaces of the gripping flanges 136, 138 of the first and second jaws 128, 130, and thus the gripping pads 140, 142, are parallel to the longitudinal axis 116, whereas the major surfaces of the jaw actuators 132, 134 slide relative to each other along a transverse axis 118 perpendicular to the longitudinal axis 116 to facilitate placement of the jaw assembly 120 between the closed and opened positions. In the illustrated embodiment, while the second jaw 130 remains fixed, the first jaw 128 translates toward the second jaw 130, thereby translating the gripping pad 140 toward the stationary gripping pad 142 to place the jaw assembly 120 in the closed position, and translates away from the second jaw 130, thereby translating the gripping pad 140 away from the stationary gripping pad 142 to place the jaw assembly 120 in the open position.

In order to guide the translation of the first jaw 128 along the transverse axis 118, the jaw assembly 120 further includes a rail 144 mounted to the base plate 122 of the respective jaw assembly 120 along the transverse axis 118, and the jaw assembly 120 includes a channeled block 146 mounted to the jaw actuator 132 of the first jaw 128 for slidably receiving the rail 144 therein, as best shown in FIG. 12 (jaw actuator 132 not shown). As will be described in further detail below, the second jaws 130 of the three jaw assemblies 120a, 120b, 120c may be translated in unison along the transverse axis 118 via operation of the grip adjustment assembly 104. In order to guide the translation of the second jaw 130 of each jaw assembly 120 along the transverse axis 118, the rail 144 extends the length of the respective base plate 122, and the respective jaw assembly 120 includes another channeled block 148 mounted to the jaw actuator 134 of the second jaw 130 for slidably receiving the rail 144 therein, as best shown in FIG. 12 (jaw actuator 134 not shown).

Figure 15:
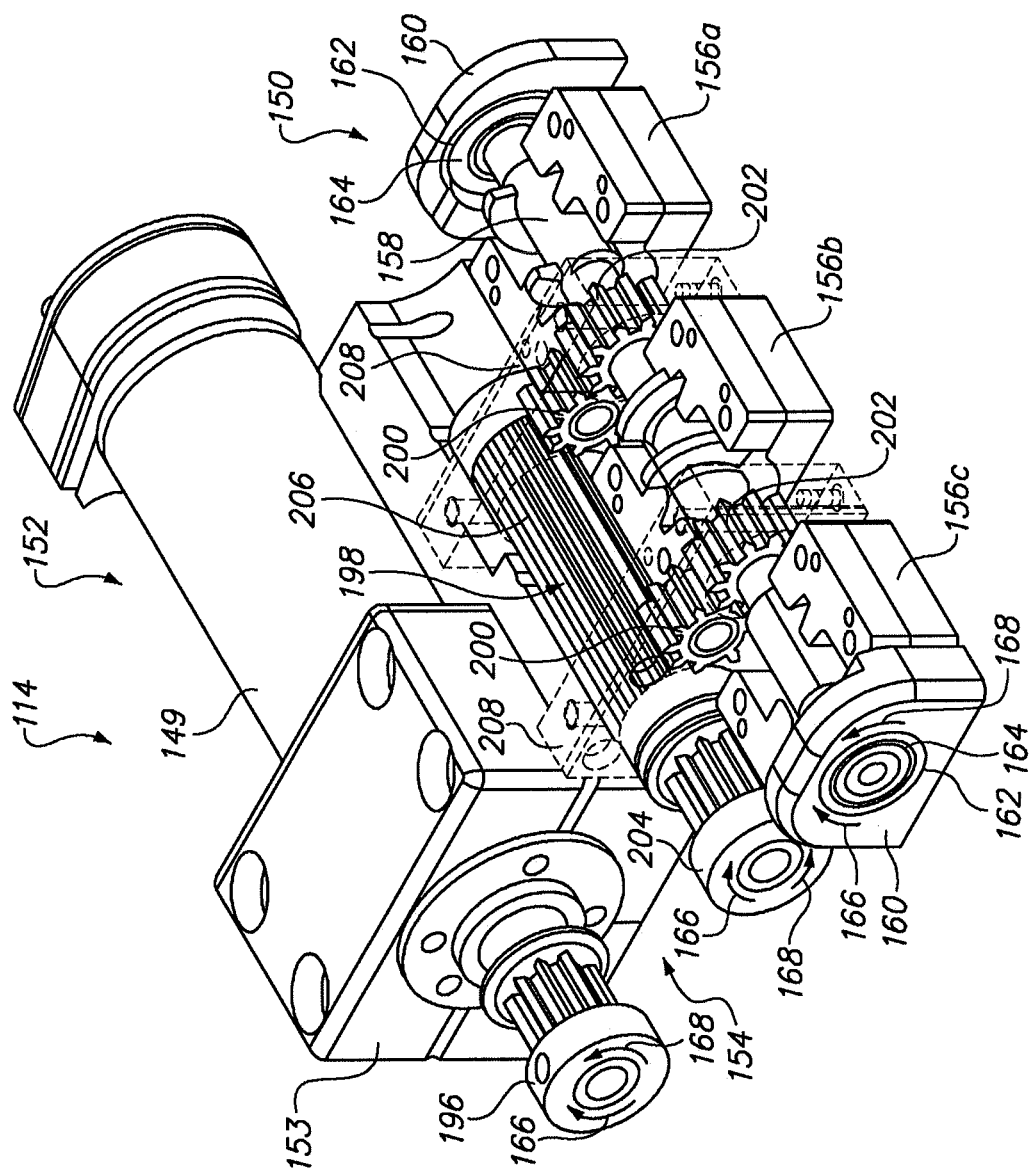
FIG. 15 is a perspective view of a driver assembly used in the catheter feeder of FIG. 6.
Figure 16:
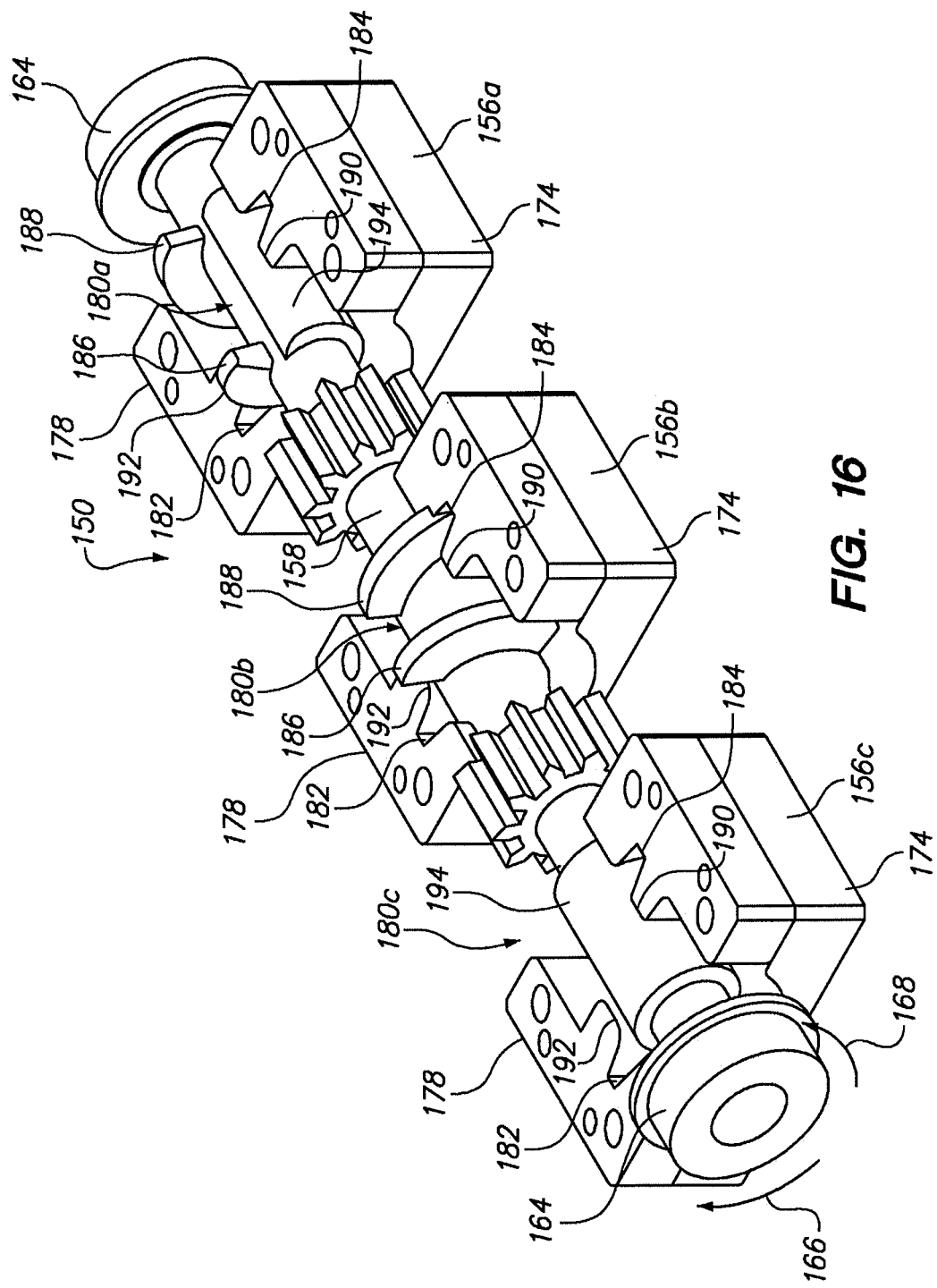
FIG. 16 is a perspective view of a cam assembly used in the driver assembly of FIG. 15.
Figure 17:
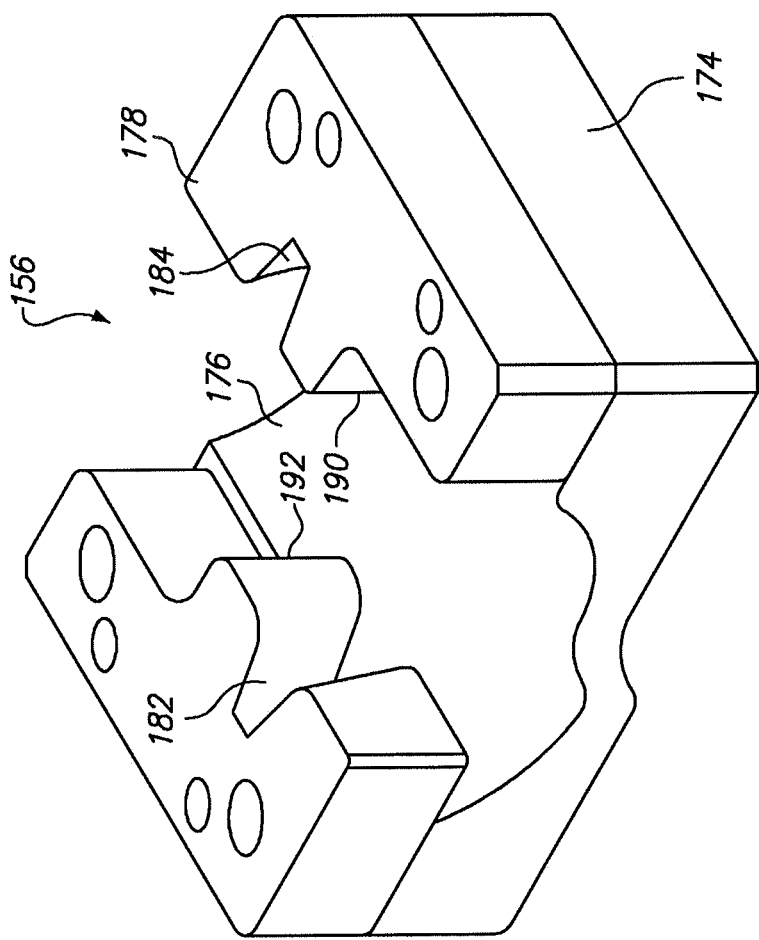
FIG. 17 is a perspective view of a cam follower element used in the cam assembly of FIG. 16.
Figure 18:
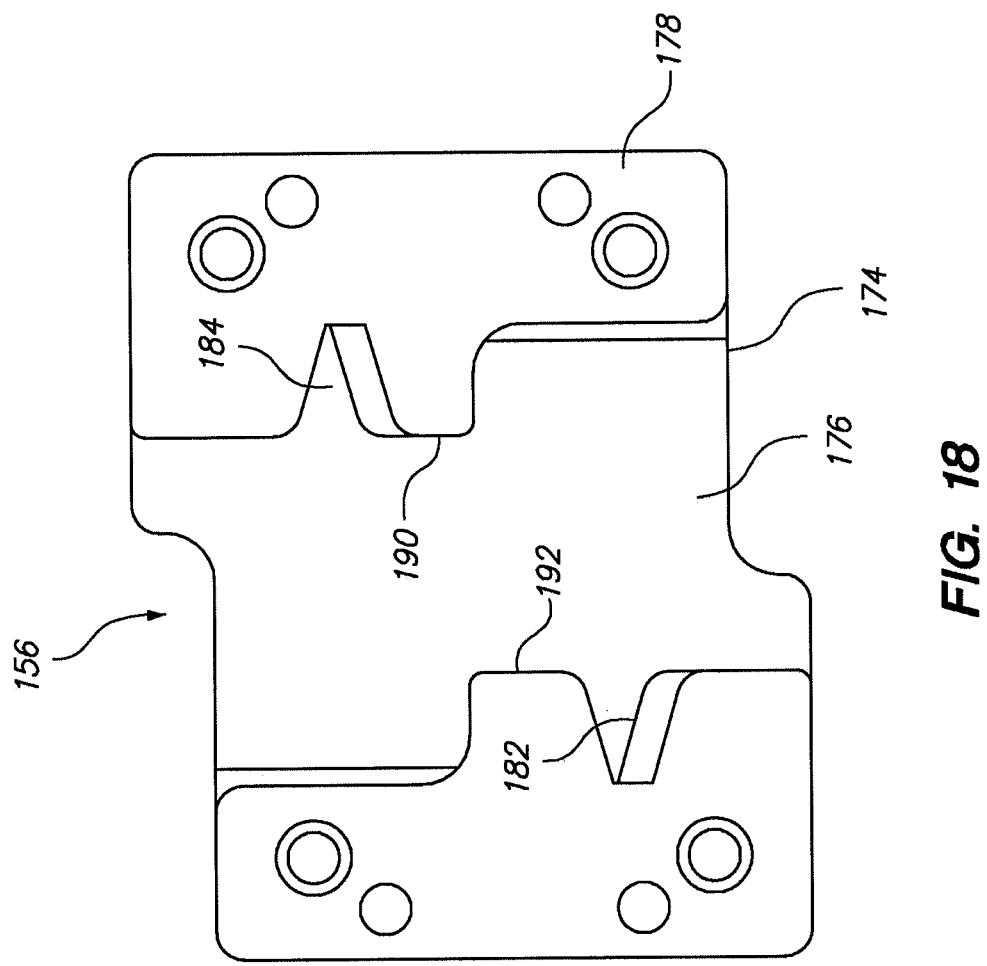
FIG. 18 is a top view of the cam follower element of FIG. 17.
Figure 19:
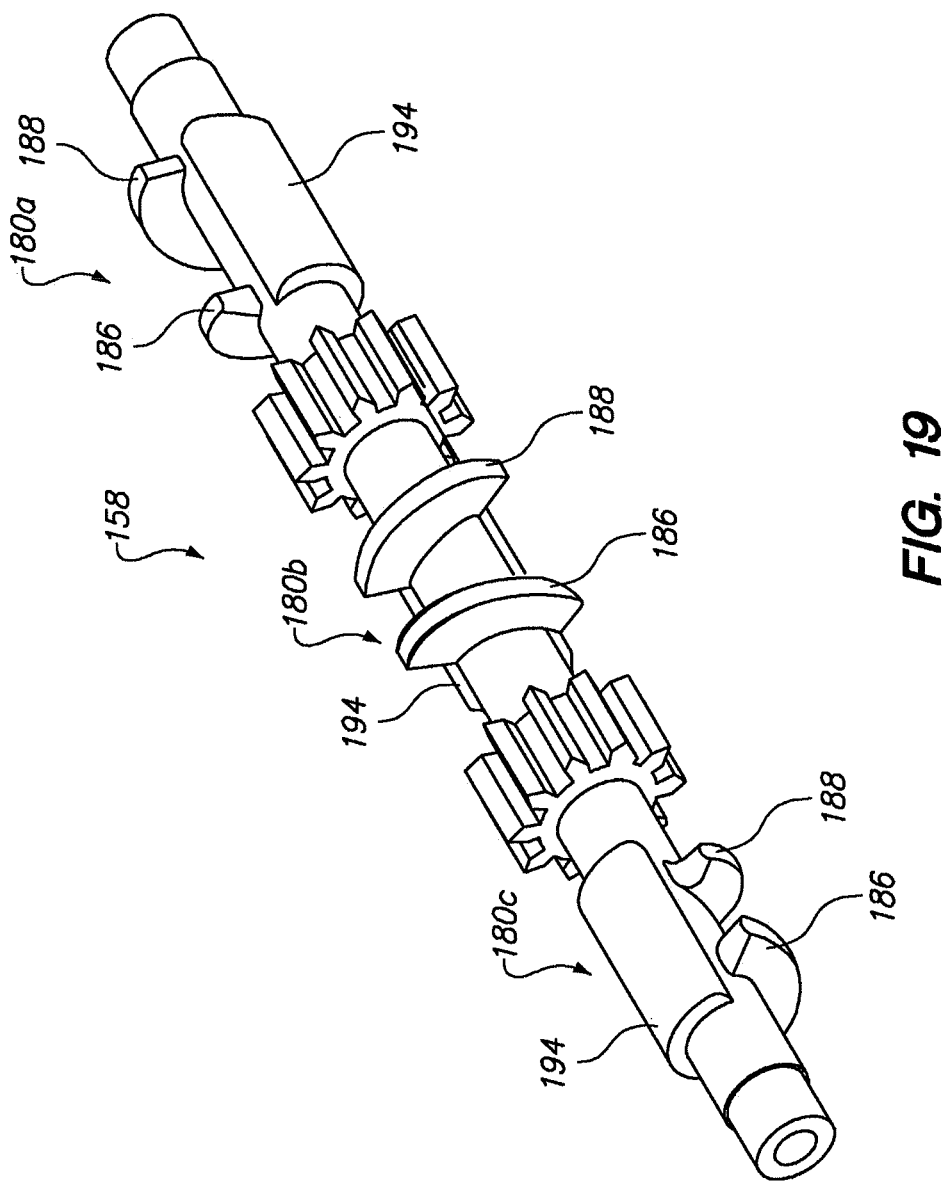
FIG. 19 is a perspective view of a cam shaft used in the cam assembly of FIG. 16.

Referring now to FIGS. 9, 10, and 15, the driver assembly 114 generally comprises a cam assembly 150 configured for actuating the respective jaw assemblies 120, a motor assembly 152, and a drive train 154 operably coupled between the motor assembly 152 and the cam assembly 150.

The cam assembly 150 is configured for translating the jaw assemblies 120 along the longitudinal axis 116, and opening and closing the respective jaw assemblies 120, in a manner that continually advances/retracts the leader catheter 38 within the guide sheath 36. To this end, the cam assembly 150 generally comprises three cam follower elements 156a, 156b, 156c respectively associated with the three jaw assemblies 120a, 120b, 120c, a cam shaft 158 disposed through the cam follower elements 156, and a pair of bearing supports 160 in which the cam shaft 158 is rotatably mounted.

Each of the bearing supports 160 includes a bearing aperture 162 and a bearing ring 164 disposed within the respective bearing aperture 162. The opposing ends of the cam shaft 158 are respectively mounted through the bearing rings 164 of the respective bearing supports 160, such that the cam shaft 158 may rotate about a longitudinal axis extending through the centers of the bearing apertures 162. The bearing supports 160 are mounted to the base plate 106 in a manner that orients the cam shaft 162 along the longitudinal axis 116.

As best shown in FIG. 9, the jaw actuators 132 of the jaw assemblies 120a, 120b, 120c (only jaw assembly 120a shown in FIG. 9) are respectively mounted to the cam follower elements 156a, 156b, 156c, such that reciprocal translation of each of the cam follower elements 156 along the longitudinal axis 116 will reciprocally translate the associated jaw assembly 120 along the longitudinal axis 116, and reciprocal translation of each of the cam follower elements 156a, 156b, 156c along the transverse axis 118 will reciprocally open or close the associated jaw assembly 120 by translating the first jaw 126 toward or away from the second jaw 126.

That is, translation of a cam follower element 156 along the longitudinal axis 116 correspondingly displaces the jaw actuator 132 of the associated jaw assembly 120 along the longitudinal axis 116. As a result, the channeled block 146 mounted to the jaw actuator 132 bears perpendicularly against the rail 144 mounted to the base plate 122 of the associated jaw assembly 120 (shown in FIG. 12), thereby translating the associated jaw assembly 120 along the longitudinal axis 116, which is guided by sliding engagement between the pair of channeled block 126 mounted to the base plate 122 of the associated jaw assembly 120 with the pair of rails 124 mounted to the base plate 106. Translation of the cam follower element 156 along the transverse axis 118 correspondingly displaces the jaw actuator 132 of the associated jaw assembly 120 along the transverse axis 118. As a result, the first jaw 126 to which the jaw actuator 132 is mounted is translated along the longitudinal axis 116 toward or away from the second jaw 126, which is guided by sliding engagement between the channeled block 146 mounted to the jaw actuator 132 with the rail 144 mounted to the base plate 122, to close or open the associated jaw assembly 120 (shown in FIGS. 13 and 14). The cam follower elements 156 are preferably spaced at least a small distance from the base plate 106 to allow the cam follower elements 156 to freely translate without friction.

The cam follower elements 156 and cam shaft 158 include cam features that, when the cam shaft 158 is rotated in a first rotational direction, advances the leader catheter 38 within the guide sheath 36, and when the cam shaft 158 is rotated in a second opposite rotational direction, retracts the leader catheter 38 within the guide sheath 36. In particular, rotation of the cam shaft 158 in either rotational direction axially translates each jaw assembly 120 along the longitudinal axis of the cam shaft 158 (i.e., along the longitudinal axis 116) via the jaw actuator 132 in a reciprocating manner, and further closes and opens each jaw assembly 120 via the jaw actuator 132 in a reciprocating manner. The reciprocating motions of the axial translation and opening/closing of each jaw assembly 120 are timed relative to each other.

In particular, as shown in FIG. 9, rotation of the cam shaft 158 in a first rotational direction 166 closes the jaw assembly 120 when the jaw assembly 120 is linearly translated in a first axial direction 170 (front stroke), and opens the jaw assembly 120 when the jaw assembly 120 is linearly translated in a second opposite axial direction 172 (rear stroke). Rotation of the cam shaft 158 in a second opposite rotational direction 168 opens the jaw assembly 120 when the jaw assembly 120 is linearly translated in the first axial direction 170 (rear stroke), and closes the jaw assembly 120 when the jaw assembly 120 is linearly translated in the second axial direction 172 (front stroke). Significantly, the reciprocating motion of each jaw assembly 120 provides for infinite advancement/retraction range of actuation for the leader catheter 38.

To this end, and with further reference to FIGS. 16-19, the three cam follower elements 156a, 156b, 156c are identical in nature, each of which includes a bottom block portion 174 having a recess 176 for receiving the bottom portion of the cam shaft 158, and a top block portion 178 having a set of cam features that interact with associated cam features on the cam shaft 158, as described below. The cam shaft 158 includes three sets of cam features 180a, 180b, 180c that respectively interact the cam features of the three cam follower elements 156a, 156b, 156c to actuate the three associated jaw assemblies 120a, 120b, 120c.

For purposes of brevity and clarity, the structure and function of the cam features of only one of the cam follower elements 156 and associated jaw assembly 120 with a corresponding set of cam features on cam shaft 158 will now be described.

The reciprocating axial motion of the jaw assembly 120 is controlled by two opposing partial worm thread features. In particular, the cam follower element 156 includes a first groove 182 and a second groove 184, and the cam shaft 158 includes a first helical cam 186 and a second helical cam 188 that are oppositely pitched (or angled) relative to each other. In the illustrated embodiment, the first and second grooves 182, 184 are arranged adjacent opposite sides of the cam shaft 158, and the first and second helical cams 186, 188 have the same circumferential orientation on the cam shaft 158. In this case, the first and second helical cams 154 are essentially mirrors of each other.

The first helical cam 186 and second helical cam 188 respectively drive the cam follower element 156 and associated jaw assembly 120 in opposite axial directions. In particular, the first helical cam 186 is capable of being engaged within the first groove 182 as the cam shaft 158 rotates during a portion of a complete rotation, thereby translating the cam follower element 156, and thus the jaw assembly 120, in one of the axial directions 170, 172 a predetermined maximum distance (the first axial direction 170 if the cam shaft 158 is rotated in the first rotational direction 166, and the second axial direction 172 if the cam shaft 158 is rotated in the second rotational direction 168), and the second helical cam 188 is capable of being engaged within the second groove 184 as the cam shaft 158 rotates during another portion of a complete rotation, thereby translating the cam follower element 156, and thus the jaw assembly 120, in the other of the axial directions 170, 172 a predetermined maximum distance (the second axial direction 172 if the cam shaft 158 is rotated in the first rotational direction 166, and the first axial direction 170 if the cam shaft 158 is rotated in the second rotational direction 168).

The circumferential lengths of the grooves 182, 184 and helical cams 186, 188 are such that at least one of the helical cams 186, 188 is always received within the respective grooves 182, 184 in order to continuously maintain control of the axial translation of the jaw assembly 120 and to ensure that each of the helical cams 186, 188 is properly aligned as it enters the respective groove 182, 184. That is, as long as one of the helical cams 186, 188 is received within its respective groove 182, 184, the other of the helical cams 186, 188 will be aligned as it enters its respective groove 182, 184. The grooves 182, 184 are axially offset from each other in a manner that aligns the helical cams 186, 188 with the respective grooves 182, 184.

The combined length of the first helical cam 186 and first groove 182 is equal to the combined length of the second helical cam 188 and second groove 184, so that the predetermined distance which the jaw assembly 120 translates in the first axial direction 144 equals the predetermined distance which the jaw assembly 120 translates in the second axial direction 170 (i.e., axial reciprocation of the jaw assembly 120 is symmetrical). This predetermined maximum distance can be considered the stroke length of the catheter feeder 100. The axial stroke length of the catheter feeder 100 may be adjusted by changing the pitch of the helical cams 186, 188. In particular, the axial stroke length can be increased by accordingly increasing the pitch of the helical cams 186, 188, whereas the stroke length can be decreased by accordingly decreasing the pitch of the helical cams 186, 188. The axial stroke length selected is dependent on the buckling strength of the leader catheter 76 and the force required to insert it into the guide sheath 74. For example, a larger pitch will provide a greater axial stroke length, but it must be ensured that the flexible leader catheter 76 can resist the insertion load over this distance without buckling. Softer, more flexible leader catheters 76 will require smaller pitches because they will have lower buckling resistance, thereby requiring shorter axial stroke lengths. It should be appreciated that adjusting the pitch of the helical cams 186, 188 does not decrease their strength in contrast to spur gear designs where the gear tooth size/strength is directly related to teeth spacing and gear diameter adjustable to change the stroke length.

Although it is possible for there to be a relatively short time during which both helical cams 186, 188 are received within the respective grooves 182, 184, it is important that both helical cams 186, 188 not actually be engaged within the respective grooves 182, 184 to prevent the conflict between opposite axial translations of the jaw assembly 120. To this end, the grooves 182, 184 have a V-shaped cross-section, and the tips of the helical cams 186, 188 are chamfered. In this manner, the helical cams 186, 188 can be respectively received within the grooves 182, 184 prior to engagement of the helical cams 186, 188 with the respective grooves 182, 184. Thus, as one of the helical cams 186, 188 disengages with its respective corresponding groove 182, 184, the other of the helical cams 186, 188 engages its respective corresponding groove 182, 184.

The reciprocating opening/closing motion of the jaw assembly 120 is controlled by a short lift duration cam feature. In particular, the cam follower element 156 further includes a first bearing surface 190 and a second bearing surface 192, and the cam shaft 158 includes a linear cam 194. The linear cam 194 is capable of engaging the first bearing surface 190 as the cam shaft 158 rotates during a portion of a complete rotation, thereby translating the cam follower element 156, and thus the gripping pad 140 of the first jaw 128, towards the gripping pad 142 of the second jaw 130 to close the jaw assembly 120, and engaging the second bearing surface 192 as the cam shaft 158 rotates during another portion of the complete rotation, thereby translating the cam follower element 156, and thus the gripping pad 140 of the first jaw 128, away from the gripping pad 142 of the second jaw 130 to open the jaw assembly 120.

In the illustrated embodiment, the first and second bearing surfaces 190, 192 are arranged adjacent opposite sides of the cam shaft 158, and the linear cam 194 is circumferentially located adjacent the tips of the first and second helical cams 186, 188. In the illustrated embodiment, the linear cam 194 is also axially centered between the first and second helical cams 186, 188, and preferably does not axially extend outside the first and second helical cams 186, 188, thereby minimizing the length of the catheter feeder 100. Alternatively, although the helical cams 186, 188 and linear cam 194 are preferably located near each other to provide for a more compact package, these cam features may be separated by any distance along the cam shaft 158.

The ends of the linear cam 194 are chamfered in order to transition engagement of the linear cam 194 with the bearing surfaces 190, 192, resulting in a gradual closing and opening of the jaw assembly 120. Because the jaw assembly 120 is only considered to be closed when the gripping pads 140, 142 of the respective jaws 128, 130 are the closest to each other, the jaw assembly 120 is considered to be closed when the unchamfered portion of the linear cam 194 are in engagement with the first bearing surface 190, and considered to be opened when the unchamfered portion of the linear cam 194 are in engagement with the second bearing surface 192. The jaw assembly 120 is considered to be transitioning from the opened position to the close position when the chamfered ends of the linear cam 194 are engaged with the first bearing surface 192, and considered to be transitioning from the closed position to the opened position when the chamfered ends of the linear cam 194 are engaged with the second bearing surface 192.

To maximize stroke efficiency, the dimensions and arrangement of the cam features are such that the jaw assembly 120 is closed at least most of the time in which it is linearly translated in the first axial direction 170 when the cam shaft 158 is rotated in the first rotational direction 166, and closed at least most of the time in which it is linearly translated in the second axial direction 172 when the cam shaft 158 is rotated in the second rotational direction 166. In other words, it is preferred that the jaw assembly 120 grip the catheter body 50 during most of its front stroke (i.e., the linear stroke intended to advance/retract the leader catheter 38). However, to ensure that the catheter body 50 is not gripped during the rear stroke (i.e., the linear stroke intended to not advance/retract the leader catheter 38), the jaw assembly 120 is preferably open for a short time at the beginning and end of the front stroke. To this end, the jaw assembly 120 completes transitions from the opened position to the closed position just after initiation of the front stroke, and begins to transition from the closed position to the opened position just prior to termination of the front stroke. Thus, the catheter body 50 will be gripped just after the front stroke is initiated, and released just before the forward is stroke is terminated.

It should be appreciated that all three jaw assemblies 120a, 120b, 120c can be driven in the axial directions in the same manner that the representative jaw assembly 120 described above is driven in the axial directions, and can be opened and closed in the same manner that the representative jaw assembly 120 described above is opened and closed. Preferably, the jaw assemblies 120 are actuated in a sequential manner that ensures that at least one jaw assembly is always closed when the cam shaft 158 is rotated, such that the leader catheter 38 is axially translated in a continuous manner during rotation of the cam shaft 158. In the illustrated embodiment, to ensure that the catheter body 50 is continuously gripped, there may be a small amount of overlap between the front strokes of two of the jaw assemblies 120, such that there is a brief period in which two of the jaw assemblies 120 are closed and gripping the catheter body 50.

This can be accomplished by clocking the three sets of cam features 180a, 180b, 180c on the cam shaft 158 one hundred twenty degrees from each other about the cam shaft 158, which sequentially actuates the jaw assemblies 120a, 120b, 120c (i.e., after the first jaw assembly 120a closes, the second jaw assembly 120b closes, and then the third jaw assembly 120c closes, and after the first jaw assembly 120a opens, the second jaw assembly 120b opens, and then the third jaw assembly 120c opens).

Referring back to FIG. 15, the motor assembly 152 comprises a motor 149, a motor mount 151 in which the motor 149 is mounted, and an electrical connector 153 configured for coupling the cable 24 to the electronics within the motor 149, thereby allowing the motor 149 to be controlled via the control station 16. The drive train 154 comprises a drive pulley 196 mounted to the drive shaft (not shown) of the motor 149, an intermediary driven shaft 198 engaged with the drive pulley 196, a pair of driven spur gears 200 engaged with the driven shaft 198, and a pair of spur gears 202 affixed to the cam shaft 158 and engaged with the driven spur gears 200.

To this end, the intermediary driven shaft 198 includes a driven pulley 204 mechanically coupled to the drive pulley 196 via a drive belt (not shown). In the illustrated embodiment, each of the drive and driven pulleys 196, 204 takes the form of a spur gear, in which case, the drive belt is cogged. The intermediary driven shaft 198 further includes an elongated spur gear 206 that meshes with the pair of spur gears 200, which in turn mesh with the respective pair of spur gears 202 affixed to the cam shaft 158. Thus, the motor 149 can be operated to rotate the drive pulley 196 in the rotational direction 166, which rotates the intermediary driven shaft 198 in the same rotational direction 166, which in turn, rotates the driven spur gears 200 in the opposite rotational direction 168, which in turn, rotates the cam shaft 158 back to the rotational direction 166. Of course, the motor 149 can also be operated to rotate the drive pulley 196 in the rotational direction 168, which rotates the intermediary driven shaft 198 in the same rotational direction 168, which in turn, rotates the driven spur gears 200 in the opposite rotational direction 166, which in turn, rotates the cam shaft 158 back to the rotational direction 168.

Figure 20:
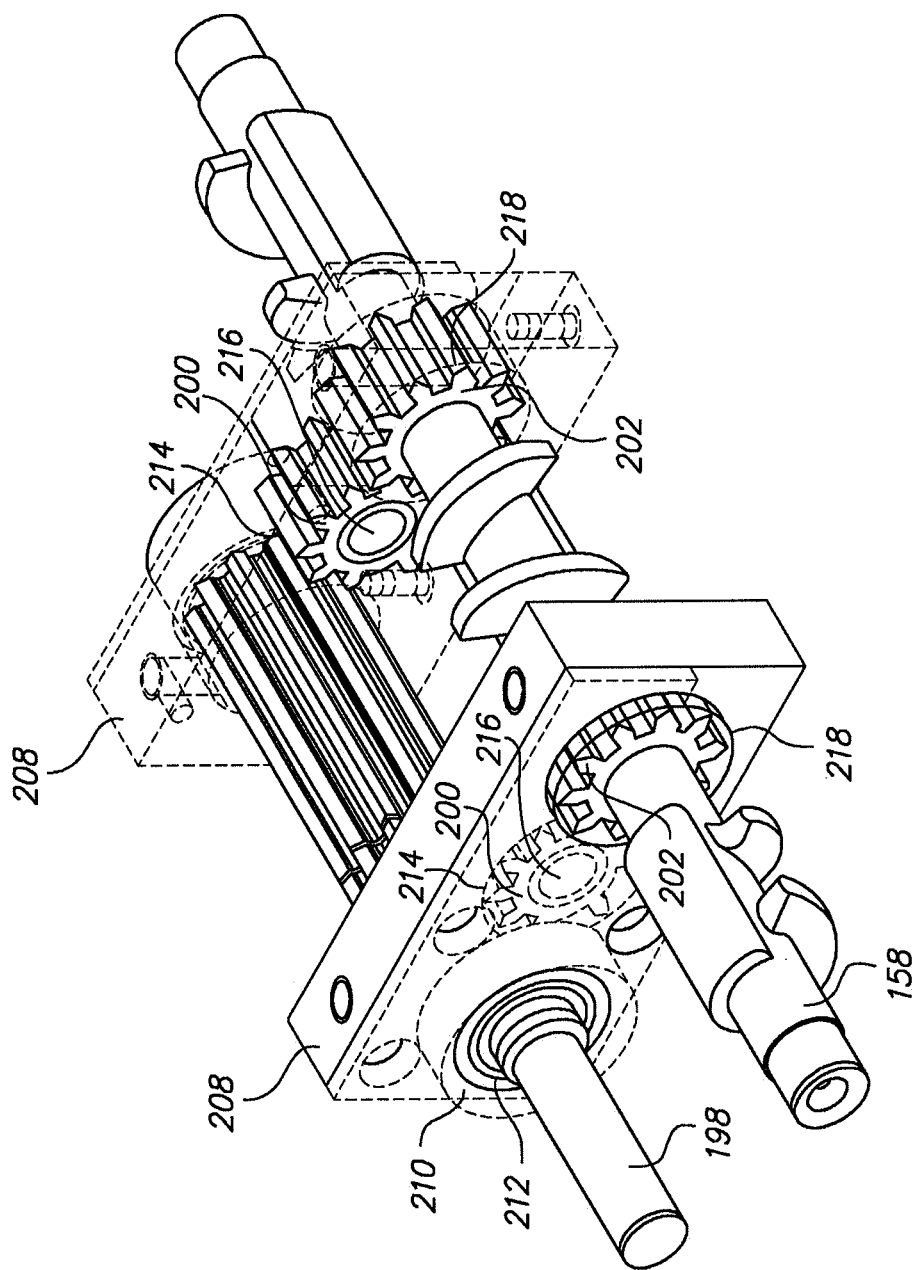
FIG. 20 is a perspective view of a bearing assembly used in the driver assembly of FIG. 15.
Figure 21:
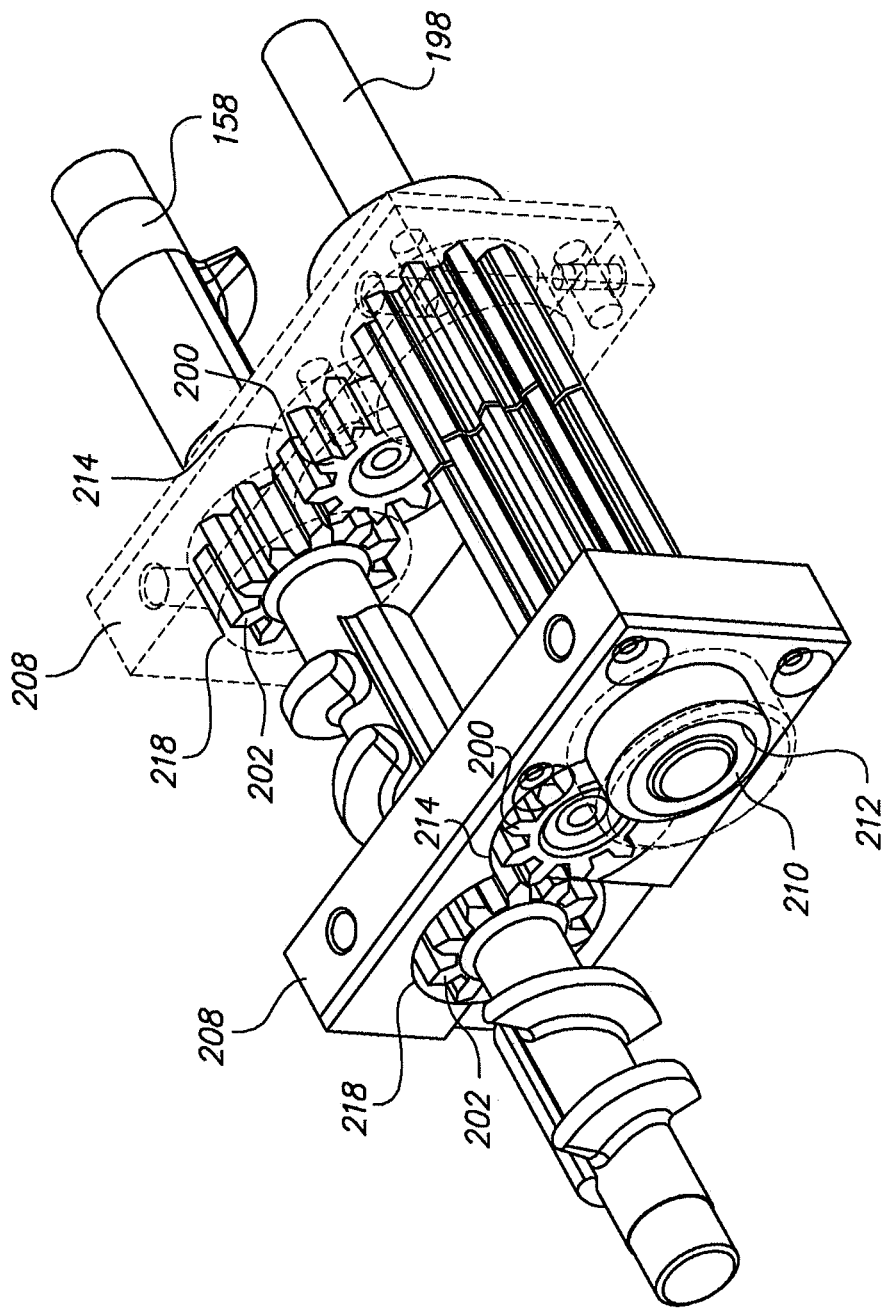
FIG. 21 is another perspective view of a bearing assembly used in the driver assembly of FIG. 15.

The drive train 154 further comprises a pair of bearing supports 208 (shown in phantom in FIG. 15) in which the intermediary driven shaft 198 and spur gears 200 are rotatably mounted. In particular, as shown in FIGS. 20 and 21 (the bearing supports 208 shown partially in phantom), each of the bearing supports 208 includes a bearing aperture 210 and a bearing ring 212 disposed within the respective bearing aperture 210. The driven shaft 198 is mounted through the bearing rings 212 of the respective bearing supports 208, such that the driven shaft 198 may rotate about a longitudinal axis extending through the centers of the bearing apertures 210. The bearing supports 208 are mounted to the base plate 106 in a manner that orients the driven shaft 198 parallel to the longitudinal axis 116. Each of the bearing supports 208 further includes another bearing aperture 214 in which a respective one of the spur gears 200 is disposed, and a bearing boss (not shown) centered within the bearing aperture 214 and received within a center hole 218 in the respective spur gear 200. Each of the bearing supports 208 lastly includes an aperture 218 in which a respective one of the spur gears 202 of the cam shaft 158 freely rotates.

It can be appreciated that the use of worm thread design in the catheter feeder 100 provides robust contact with the reciprocating components, and in this case, the jaws 128, 130. Furthermore, the catheter feeder 100 provides for a constant velocity advancement/retraction of the leader catheter 38 in comparison to other reciprocating devices, which are more sinusoidal, and thus, do not lend themselves as well to mimicking the finger feeding performed by physicians. It should also be appreciated that, although the catheter feeder 100 is described as comprising three jaw assemblies 120a, 120b, 120c, an alternative catheter feeder 100 may include only one jaw assembly 120. In this case, advancement and retraction of the catheter body 50 will not be continuous, but will be intermittent.

Figure 22:
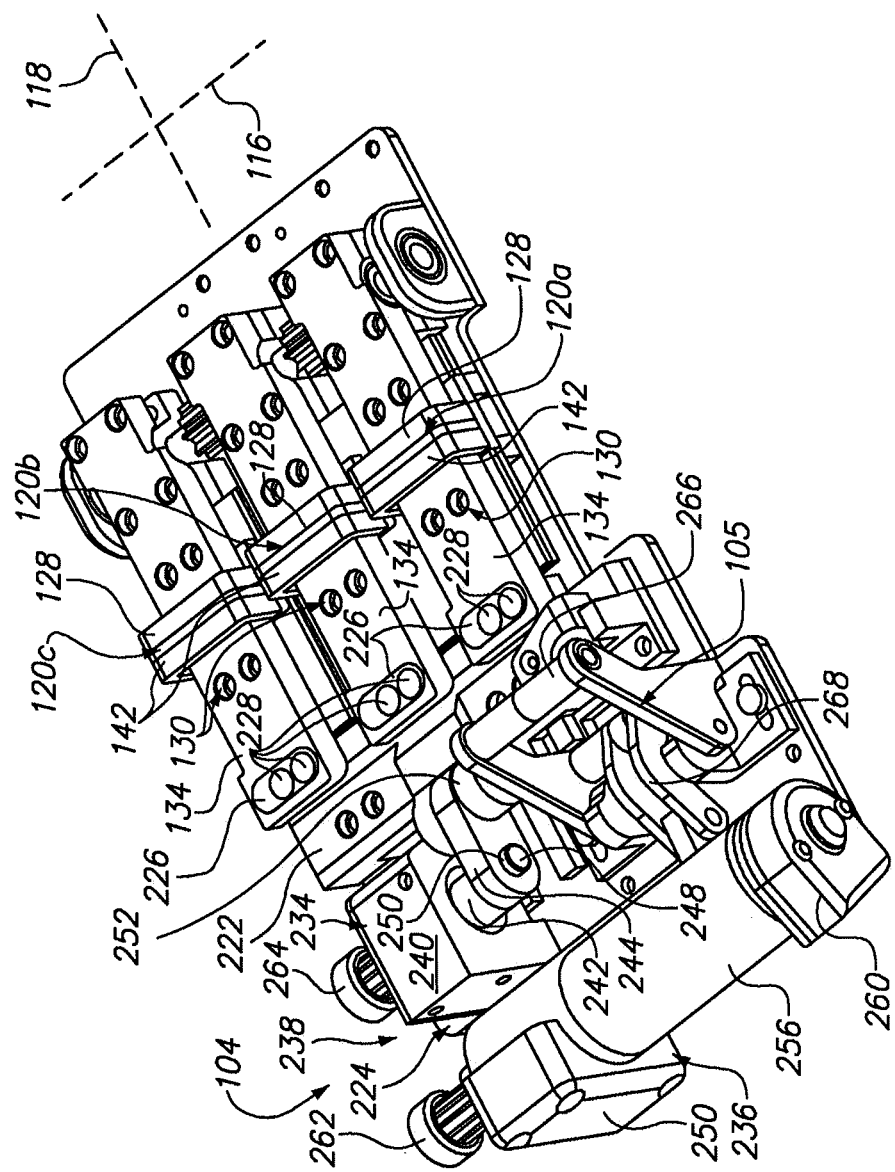
FIG. 22 is a perspective view of a portion of the driver assembly FIG. 15, the jaw assembly arrangement FIG. 13, and a grip adjustment assembly and loading/unloading assembly used in the catheter feeder of FIG. 6.
Figure 23:
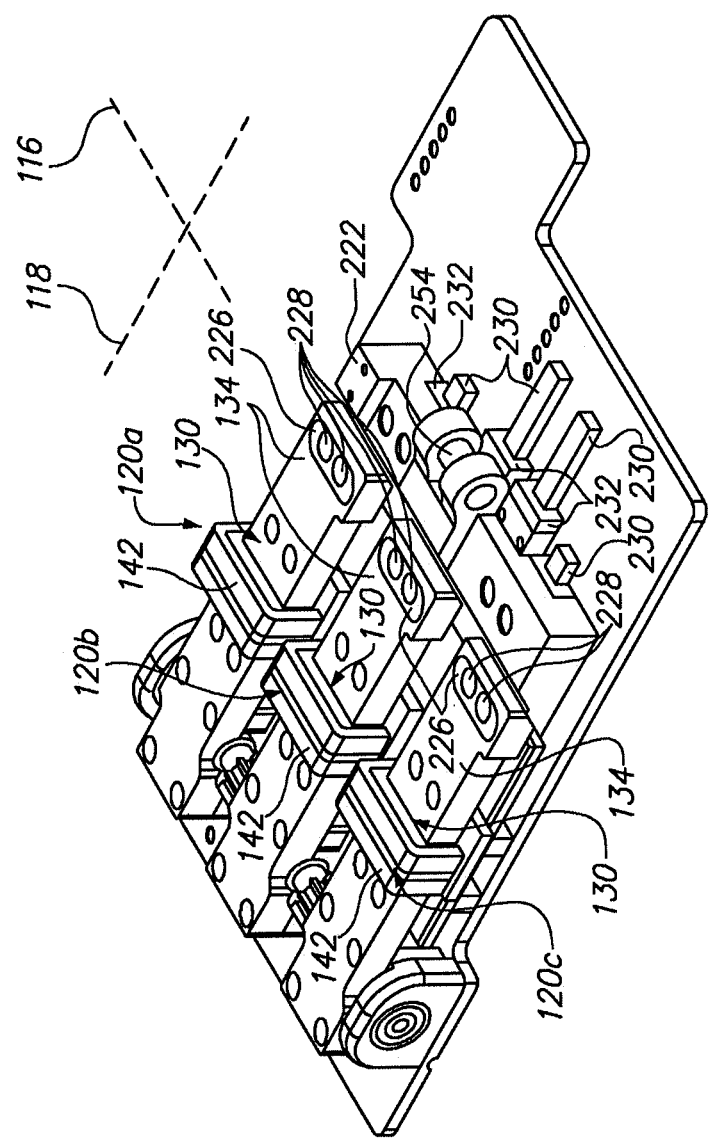
FIG. 23 is a perspective view of a portion of the driver assembly FIG. 15, the jaw assembly arrangement FIG. 13, and a yoke used in the grip adjustment assembly of FIG. 23.

Referring now to FIGS. 22 and 23, the grip adjustment assembly 104 generally comprises a yoke 222 coupled to the second jaws 130 of the three respective jaw assemblies 120a, 120b, 120c, and a driver assembly 224 configured for actuating the yoke 222 to adjust the positions of the stationary gripping pads 142, and thus, the grip between the gripping pads 140, 142.

To this end, the yoke 222 is mechanically coupled to the jaw actuators 134 of the jaw assemblies 120, such that translation of the yoke 222 along the transverse axis 118 correspondingly translates the second jaws 130 of all three jaw assemblies 120 along the transverse axis 118 in unison, while allowing the jaw assemblies 120 to translate relative to each other along the longitudinal axis 116 within a limited range. Each of the jaw actuators 134 includes a channel 226 extending along the longitudinal axis 116, and the yoke 222 includes three pairs of bosses 228, each pair being disposed within the channel 226 of a respective jaw actuator 134.

Thus, translation of the yoke 222 along the transverse axis 118 causes the channels 226 to bear against the bosses 228, thereby translating the jaw actuators 134, and thus, the second jaws 130 of the jaw assemblies 120 along the transverse axis 118. The diameters of the bosses 228 are equal to the width of the respective channel 226 to provide close tolerance between the translations of the yoke 222 and second jaws 130 along the transverse axis 118. The length of each channel 226 is greater than the longitudinal span of the respective pair of bosses 228, such that jaw actuators 134, and thus the jaw assemblies 120, can translate relative to the yoke 222 along the longitudinal axis 116 within a limited range. In order to guide translation of yoke 222 along the transverse axis 118, the grip adjustment assembly 104 further comprises four parallel rails 230 mounted to the base plate 106 along the transverse axis 118, and the yoke 222 includes four channeled blocks 232 for slidably receiving the rails 230 therein, as best shown in FIG. 23. It can be appreciated that the second jaws 130 can be translated away from the first jaws 128 to loosen the grip between, or accommodate a larger diameter catheter body 50, and translated toward the first jaws 128 to tighten the grip between, or accommodate a smaller diameter catheter body 50.

As best shown in FIG. 22, the driver assembly 224 generally comprises a cam assembly 234 configured for actuating the yoke 222, a motor assembly 236, and a drive train 238 operably coupled between the motor assembly 236 and the cam assembly 234.

The cam assembly 234 is configured for translating the yoke 222 along the transverse axis 118, thereby translating the second jaws 130 toward or away from the first jaws 128 of the respective jaw assemblies 120. To this end, the cam assembly 234 generally comprises a bearing support 240, a cam shaft 242 rotatably disposed within the bearing support 240, and a cam follower element 244 coupled between the cam shaft 242 and the yoke 222.

The bearing support 240 includes a bearing aperture 244 and a pair of bearing rings 246 disposed within the bearing aperture 244. The cam shaft 242 is mounted through the bearing rings (not shown) of the bearing support 240, such that the cam shaft 242 may rotate about a longitudinal axis extending through the center of the bearing aperture 244.

The cam shaft 242 comprises a cam element 248 in the form of a rod that is eccentric with the longitudinal axis of the cam shaft 242. The cam follower element 244 includes a first aperture 250 through which the cam element 248 is rotatably disposed, and a second aperture 252 in which a cross bar 254 (shown in FIG. 23) affixed to the yoke 222 is rotatably disposed. Due to the eccentricity of the cam element 248 relative to the longitudinal axis of the cam shaft 248, rotation of the cam shaft 248 will cause the cam element 248 to orbit the longitudinal axis of the cam shaft 242, thereby causing the cam follower element 244, and thus the yoke 222 via the cross bar 254, to alternately translate along the transverse axis 118 in a reciprocating manner. Thus, rotation of the cam shaft 242 in one direction will cause the yoke 222 to translate along the transverse axis 118, and further rotation of the cam shaft 242 in the same direction will cause the yoke 222 to translate in the opposite direction along the transverse axis 118, thereby adjusting the distance between the gripping pads 140, 142 of the respective jaw assemblies 120. A spring (not shown) may be optionally added to the assembly to have better control of the force applied to the leader catheter 76.

The motor assembly 236 comprises a motor 256, a motor mount 258 (only a portion of which is shown in FIG. 22) in which the motor 256 is mounted, and an electrical connector 260 configured for coupling the cable 24 to the electronics within the motor 256, thereby allowing the motor 256 to be controlled via the control station 16. The drive train 238 comprises a drive pulley 262 mounted to the drive shaft (not shown) of the motor 254, and a driven pulley 264 mounted to the cam shaft 242. The drive pulley 262 and driven pulley 264 are mechanically coupled to each other via a drive belt (not shown). In the illustrated embodiment, each of the drive and driven pulleys 262, 264 takes the form of a spur gear, in which case, the drive belt is cogged. Thus, the motor 256 can be operated to rotate the drive pulley 262, which rotates the cam shaft 242.

The loading/unloading assembly 105 generally comprises a switch handle 266 mounted to the base plate 106, and a lever 268 mechanically coupled between the switch handle 266 and the motor mount 258. Significantly, the bearing support 240 and motor mount 258 are not mounted to the base plate 106, but rather are affixed to each other in an integrated unit capable of being translated relative to the base plate 106 along the transverse axis 118. Accordingly, when the switch handle 266 is rotated in a direction away from the jaw assemblies 120, the lever 268 likewise translates the motor mount 258 away from the jaw assemblies 120. As a result, the bearing support 240, and thus the cam shaft 242 and cam follower element 244, will be translated away from the jaw assemblies 120, thereby translating the second jaws 130 away from the first jaws 128 of the jaw assemblies 120 via the yoke 222. In contrast, when the switch handle 266 is rotated in a direction toward the jaw assemblies 120, the lever 268 likewise translates the motor mount 258 toward the jaw assemblies 120. As a result, the bearing support 240, and thus the cam shaft 242 and cam follower element 244, will be translated toward the jaw assemblies 120, thereby translating the second jaws 130 toward the first jaws 128 of jaw assemblies 120 via the yoke 222.

It can be appreciated that the second jaws 130 can be translated away from the first jaws 128 (via rotation of the switch handle 266 away from the jaw assemblies 120) to allow the catheter body 50 to be easily dropped into the respective jaw assemblies 120, and then translated toward the first jaws 128 (via rotation of the switch handle 266 toward the jaw assemblies 120) to affix the catheter body 50 within the respective jaw assemblies 120, in effect allowing top loading of the catheter body 50 into the catheter feeder 100. Then, the second jaws 130 can be translated away from the first jaws 128 (via rotation of the switch handle 266 away from the jaw assemblies 120) to allow the catheter body 50 to be easily removed from the respective jaw assemblies 120, in effect allowing top unloading of the catheter body 50 from the catheter feeder 100.

Figure 24:
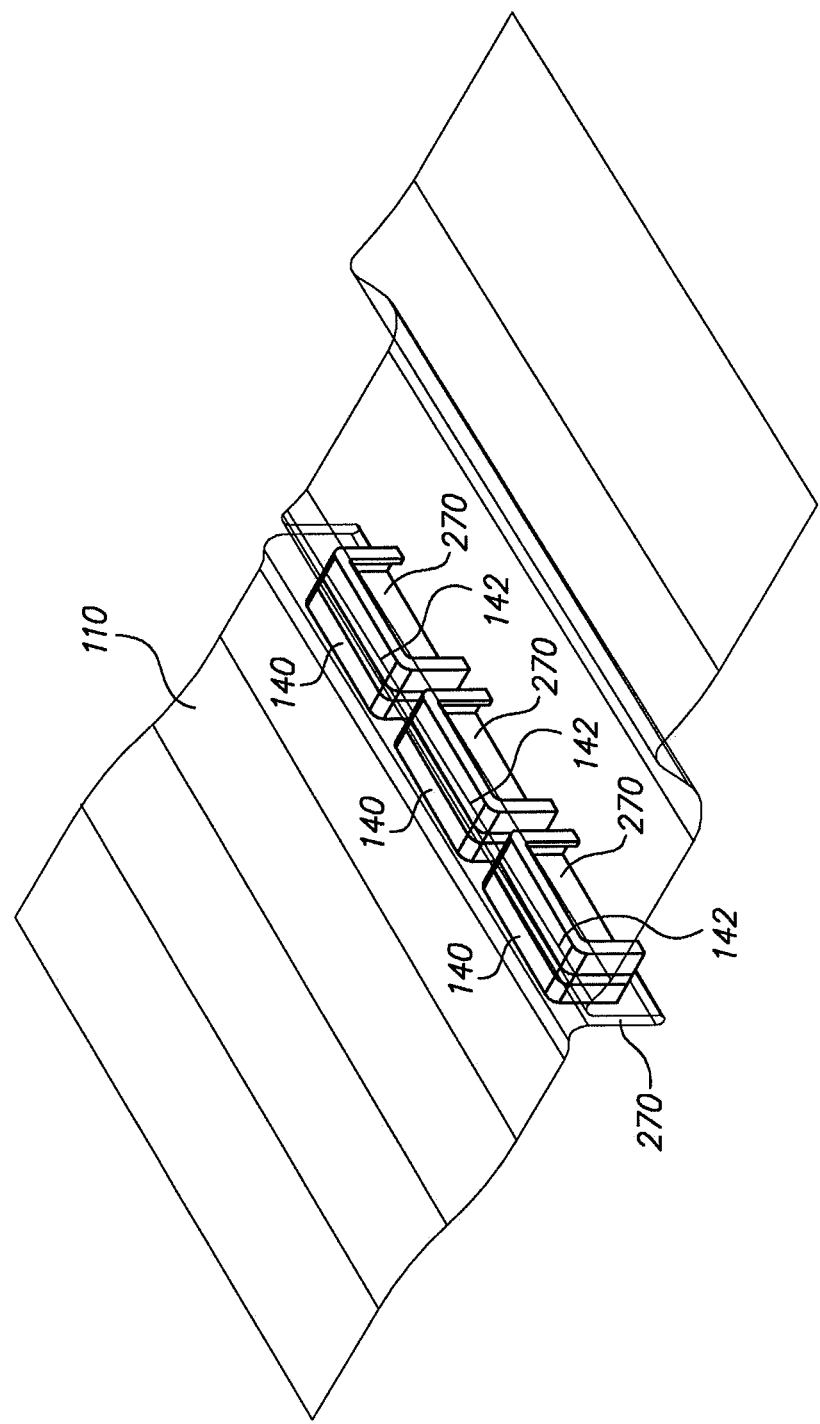
FIG. 24 is a perspective view of a drape used in the catheter feeder of FIG. 6.

Referring to FIG. 24, the drape 110 is integrated with the gripping pads 140, 142, such the drape 110 and gripping pads 140, 142 form a disposable unit. In particular, the drape 110 includes a fold 270, with one side of the fold 270 being integrated with the three gripping pads 140, and the other side of the fold 270 being integrated with the three gripping pads 142. Each of the gripping pads 140, 142 includes a pocket 272 in which a respective one of the gripping flanges 136, 138 are removably seated. Thus, prior to the medical procedure, the drape 110 may be installed onto the catheter feeder 100 by clipping the gripping flanges 136, 138 into the pockets 272 of the respective gripping pads 140, 142. After the medical procedure is completed, the drape 110 may then be removed from the catheter feeder 100 by unclipping the gripping flanges 136, 138 from the pockets 272 of the respective gripping pads 140, 142.

Having described the structure and function of the catheter feeder 100, its operation in advancing and retracting the leader catheter 38 within the guide sheath 36 will now be described. For purposes of clarity, the advancement and retraction of the leader catheter 28 within the guide sheath 36 will first be described with respect to the operation of a single jaw assembly 120.

With reference back to FIGS. 9, 15, and 16, to advance the leader catheter 38 within the guide sheath 36, the cam shaft 158 is continuously rotated in the first rotational direction 166 via operation of the motor 149 to mimic the manual finger feed method that physicians may use to advance the leader catheter 38 within the guide sheath 36.

In particular, it is initially assumed that the jaw assembly 120 has been translated the maximum predetermined distance in the second axial direction 172. At this point, the linear cam 194 on the cam shaft 158 is engaging the first bearing surface 190 on the cam follower element 156, thereby continuing transition of the jaw assembly 120 from the opened position to the closed position, the second helical cam 188 on the cam shaft 158 has just disengaged the second groove 184 on the cam follower element 156, thereby terminating linear translation of the jaw assembly 120 in the second axial direction 172, and the first helical cam 186 on the cam shaft 158 has just engaged the first groove 182 on the second jaw 124, thereby initiating linear translation of the jaw assembly 120 in the first axial direction 170 (the jaw assembly 120 has just completed the rear stroke and is initiating the front stroke) (see FIG. 25*a*).

The first helical cam 186 on the cam shaft 158 continues to engage the first groove 182 on the cam follower element 156, thereby linearly translating the jaw assembly 120 in the first axial direction 170, while the linear cam 194 on the cam shaft 158 continues to engage the first bearing surface 190 on the cam follower element 156 until the jaw assembly 120 is closed, thereby gripping the catheter body 50 (the jaw assembly 120 completes the beginning stage of the front stroke) (see FIG. 25*b*). The first helical cam 186 on the cam shaft 158 continues to engage the first groove 182 on the second jaw 124, thereby linearly translating the closed jaw assembly 120 in the first axial direction 170, and inserting the leader catheter 38 within the guide sheath 36 (the jaw assembly 120 completes the middle stage of the front stroke) (see FIG. 25*c*).

The linear cam 194 on the cam shaft 158 then disengages the first bearing surface 190 on the cam follower element 156, and engages the second bearing surface 192 on the cam follower element 156, thereby initiating transition of the jaw assembly 120 from the closed position to the opened position and releasing the catheter body 50, while the first helical cam 186 on the cam shaft 158 continues to engage the first groove 182 on the cam follower element 156 until the jaw assembly 120 translates the maximum distance in the first axial direction 170. At this point, the linear cam 194 on the cam shaft 158 is engaging the second bearing surface 192 on the cam follower element 156, thereby continuing transition of the jaw assembly 120 from the closed position to the opened position, the first helical cam 186 on the cam shaft 158 has just disengaged the first groove 182 on the cam follower element 156, thereby terminating linear translation of the jaw assembly 120 in the first axial direction 170, and the second helical cam 188 on the cam shaft 158 has just engaged the second groove 184 on the cam follower element 156, thereby initiating linear translation of the jaw assembly 120 in the second axial direction 172 (the jaw assembly 120 has just completed the front stroke and is initiating the rear stroke) (see FIG. 25*d*).

The second helical cam 188 on the cam shaft 158 continues to engage the second groove 184 on the cam follower element 156, thereby linearly translating the jaw assembly 120 in the second axial direction 172, while the linear cam 194 on the cam shaft 158 continues to engage the second bearing surface 192 on the cam follower element 156 until the jaw assembly 120 is open, thereby fully releasing the catheter body 50 (the jaw assembly 120 completes the beginning stage of the rear stroke) (see FIG. 25*e*). The second helical cam 188 on the cam shaft 158 continues to engage the second groove 150 on the cam follower element 156, thereby linearly translating the closed jaw assembly 120 in the second axial direction 172 (the jaw assembly 120 completes the middle stage of the rear stroke) (see FIG. 25*f*). The linear cam 194 on the cam shaft 158 then disengages the second bearing surface 192 on the cam follower element 156, and engages the first bearing surface 190 on the cam follower element 156, thereby initiating transition of the jaw assembly 120 from the opened position to the closed position, while the second helical cam 188 on the cam shaft 158 continues to engage the second groove 184 on the cam follower element 156 until the jaw assembly 120 translates the maximum distance in the second axial direction 172 (the jaw assembly 120 completes the end stage of the rear stroke) (see FIG. 25*g*).

Rotation of the cam shaft 158 may continue to be rotated in the first rotational direction 166 to repeat the previous steps, thereby further advancing the leader catheter 38 within the guide sheath 36. Thus, it can be appreciated that the leader catheter 38 can be incrementally advanced within the guide sheath 36 via continuous rotation of the cam shaft 158 in the first rotational direction 166.

To retract the leader catheter 38 within the guide sheath 36, the cam shaft 158 is continuously rotated in the second rotational direction 168 via operation of the motor 149 to mimic the manual finger retract method that physicians may use to retract the leader catheter 38 within the guide sheath 36. In particular, the same manipulation steps described above with respect to the advancement of the leader catheter 38 are performed, with the caveat that the front stroke occurs in the second axial direction 172, and the rear stroke occurs in the first axial direction 170.

Having described the technique for advancing and retracting the leader catheter 38 within the guide sheath 36 using a single jaw assembly 120, one technique for advancing and retracting the leader catheter 38 within the guide sheath 36 using the three jaw assemblies 120*a*, 120*b*, 120*c* will now be described. Each of the jaw assemblies 120*a*, 120*b*, 120*c* can transition between the different stages of the front and rear strokes in the same manner discussed above, but timed in a manner that provides continuous advancement/retraction of the leader catheter 38 within the guide sheath 36.

Figure 26A:
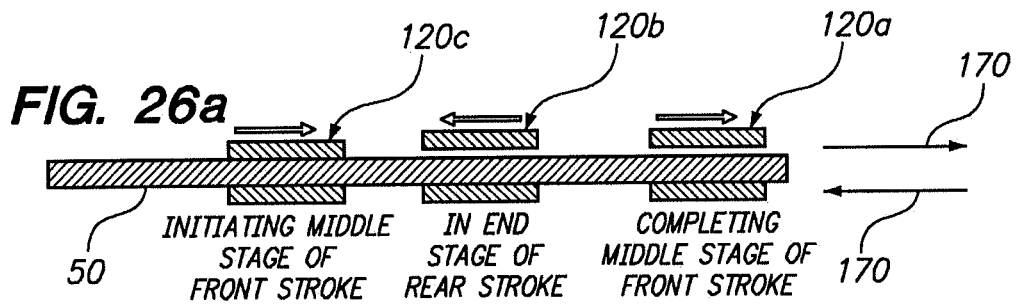
FIGS. 26a-26d are plan views illustrating an exemplary sequence used by the catheter feeder of FIG. 6 to open, close, and translate three jaw assemblies of the jaw assembly arrangement FIG. 11 to advance/retract the leader catheter within the guide sheath of the catheter assembly of FIG. 4.

It is initially assumed that jaw assembly 120*c* is closed and being translated in the first axial direction 170, thereby performing the leader catheter advancement function (the jaw assembly 120*c* is initiating the middle stage of its front stroke), the jaw assembly 120*b* is transitioning from the opened position to the closed position and being translated in the second axial direction 172, thereby readying it to take over the leader catheter advancement function from the first jaw assembly 120*a* (the jaw assembly 120*b* is in the end stage of its rear stroke), and the jaw assembly 120*a* is transitioning from the closed position to the opened position and being translated in the second axial direction 172 (the jaw assembly 120*a* is completing the middle stage of its front stroke) (see FIG. 26*a*).

Figure 26B:
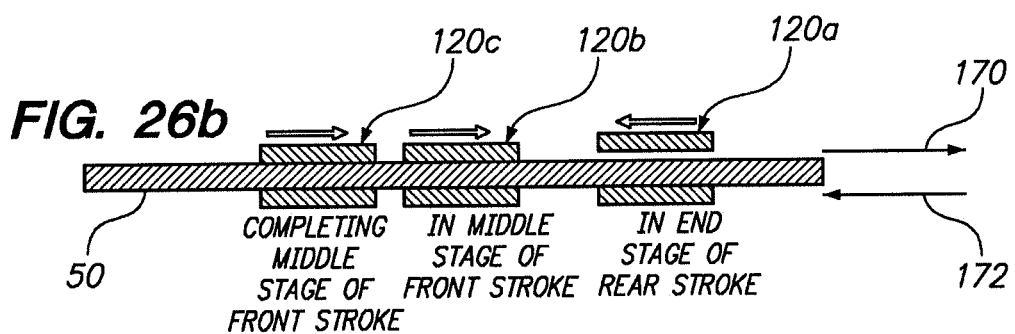

Just prior to transitioning the jaw assembly 120*c* from the closed position to the opened position during its translation in the first axial direction 170 (the jaw assembly 120*c* is completing the middle stage of its front stroke), the jaw assembly 120*b* is transitioned from the opened position to the closed position while translating in the first axial direction 170, thereby taking over the leader catheter advancement function from the jaw assembly 120*c* (the jaw assembly 120*b* completes the end stage of its rear stroke and the initial stage of its front stroke, and initiating the middle stage of its front stroke), and the jaw assembly 120*a* is transitioning from the opened position to the closed position while continuing to be translated in the second axial direction 172, thereby readying it to take over the leader catheter advancement function from the jaw assembly 120b (the jaw assembly 120a completes the end stage of its front stroke and the initial stage of its rear stroke, and is in the end stage of its rear stroke) (see FIG. 26b).

Figure 26C:
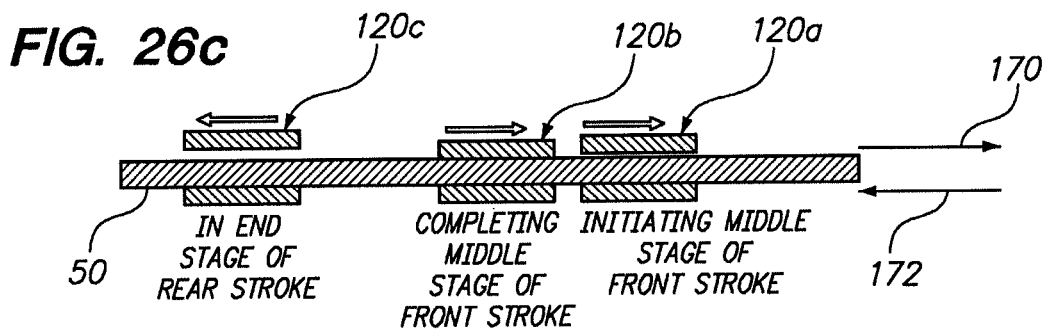

Just prior to transitioning the jaw assembly 120b from the closed position to the opened position during its translation in the first axial direction 170 (the jaw assembly 120b is completing the middle stage of its front stroke), the jaw assembly 120a is transitioned from the opened position to the closed position while translating in the first axial direction 170, thereby taking over the leader catheter advancement function from the jaw assembly 120b (the jaw assembly 120a completes the end stage of its rear stroke and the initial stage of its front stroke, and is initiating the middle stage of its front stroke), and the jaw assembly 120c is transitioning from the opened position to the closed position while continuing to be translated in the second axial direction 172, thereby readying it to take over the leader catheter advancement function from the jaw assembly 120a (the jaw assembly 120c completes the end stage of its front stroke and the initial stage of its rear stroke, and is in the end stage of its rear stroke) (see FIG. 26c).

Figure 26D:
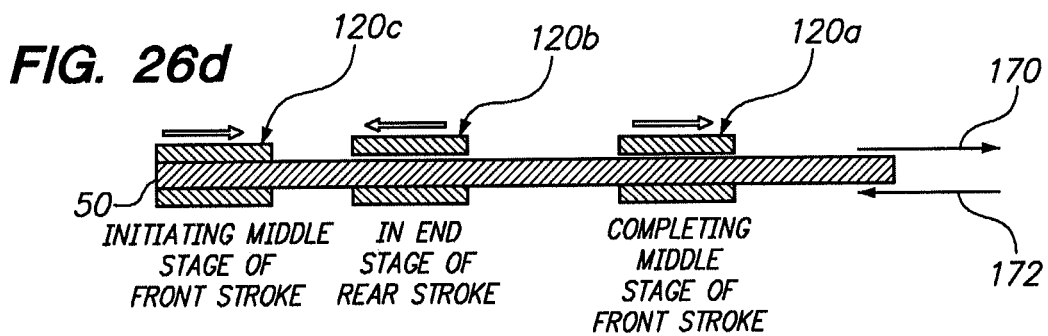
Figure 27:
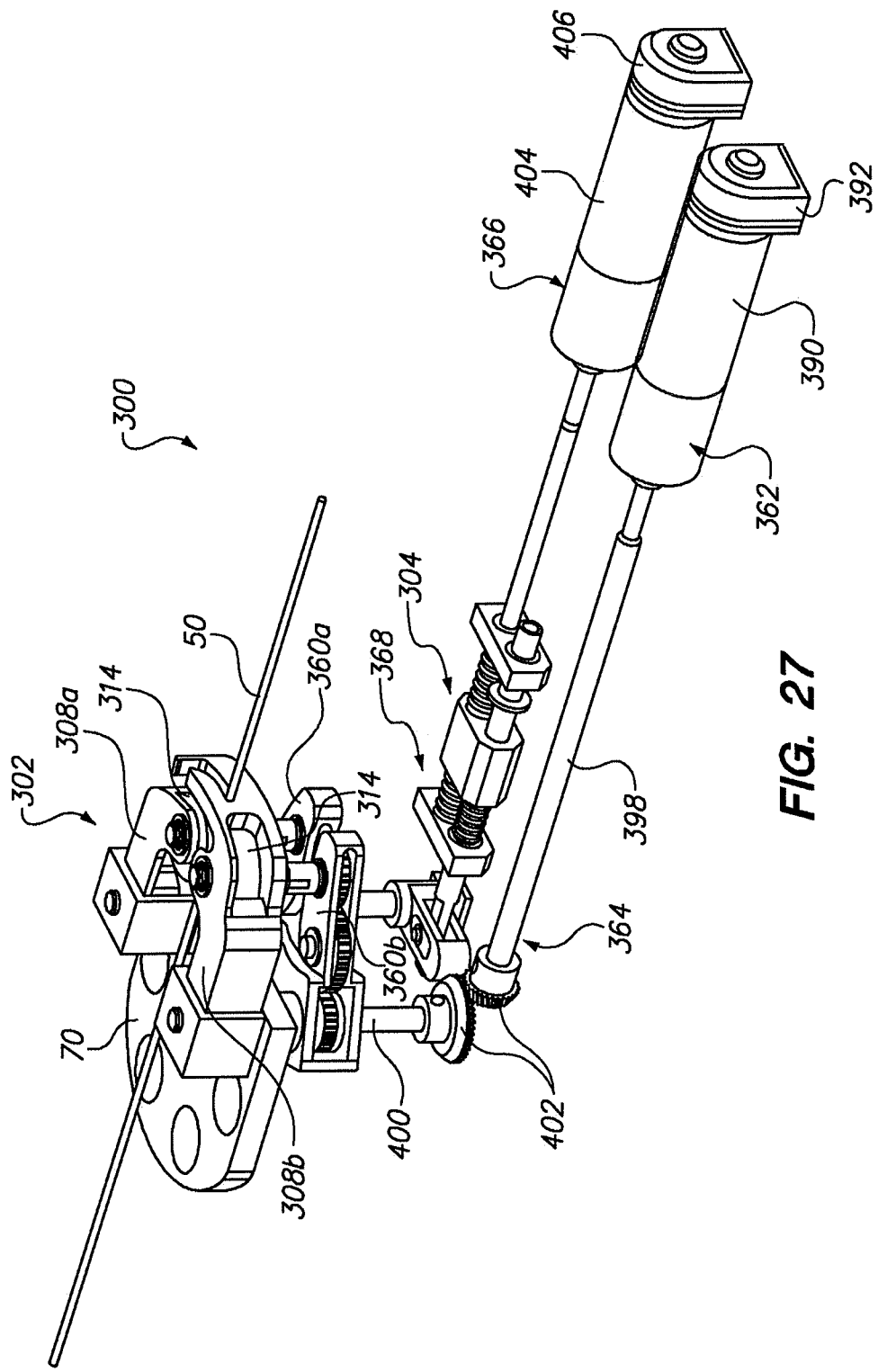
FIG. 27 a perspective view of another embodiment of a catheter feeder that can be used in the instrument driver of FIG. 5, particularly showing the catheter feeder in a closed position.
Figure 28:
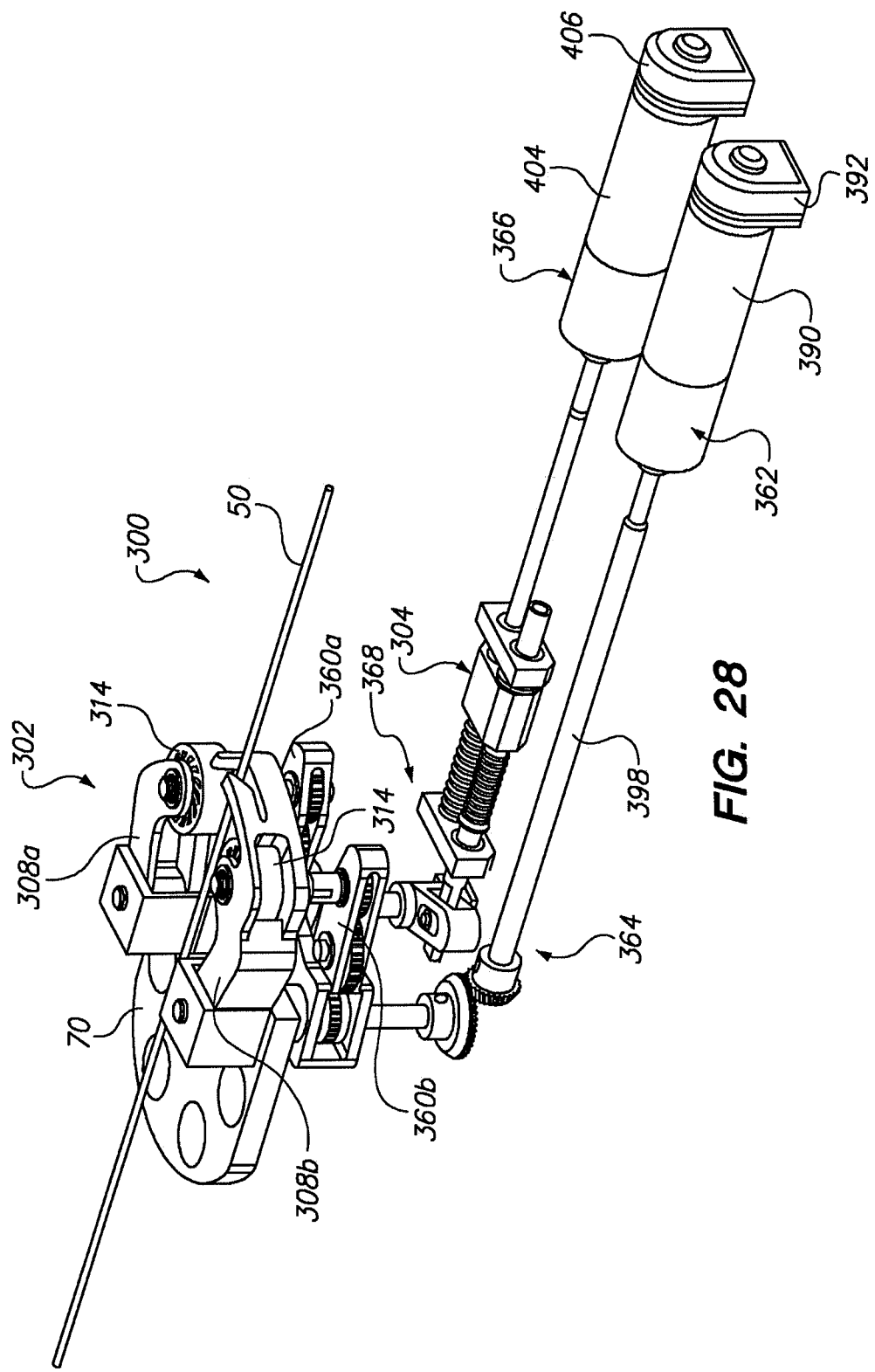
FIG. 28 a perspective view of the catheter feeder of FIG. 27, particularly showing the catheter feeder in an opened position.
Figure 29:
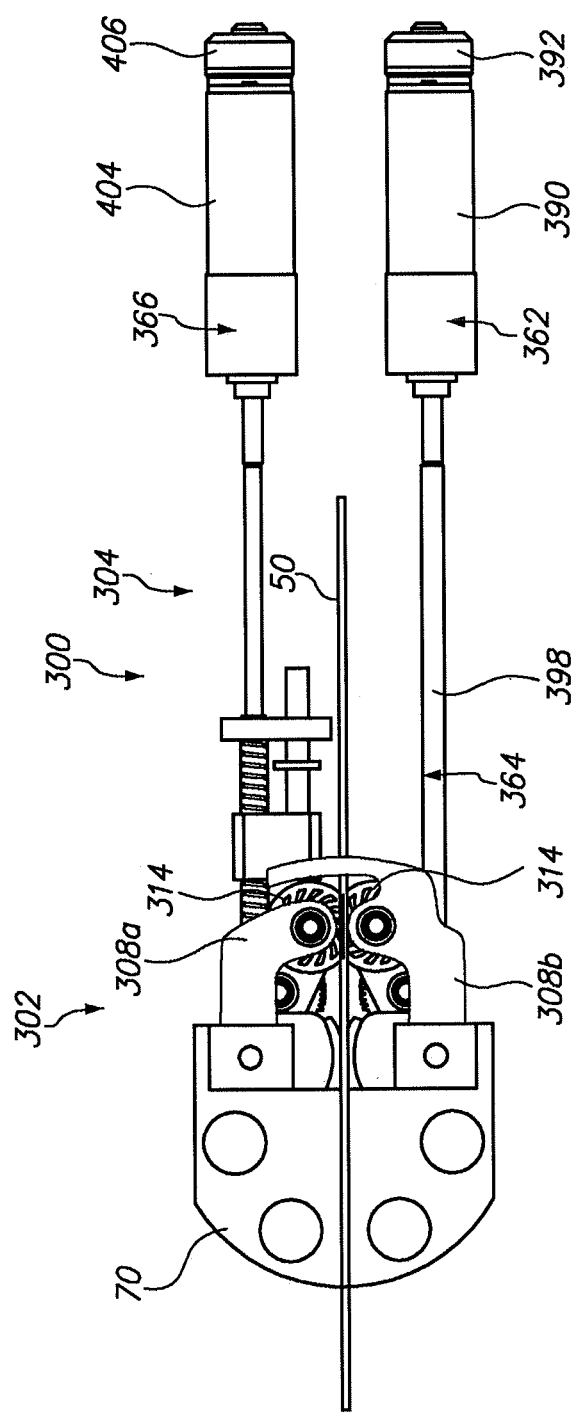
FIG. 29 a top view of the catheter feeder of FIG. 27, particularly showing the catheter feeder in the closed position.
Figure 30:
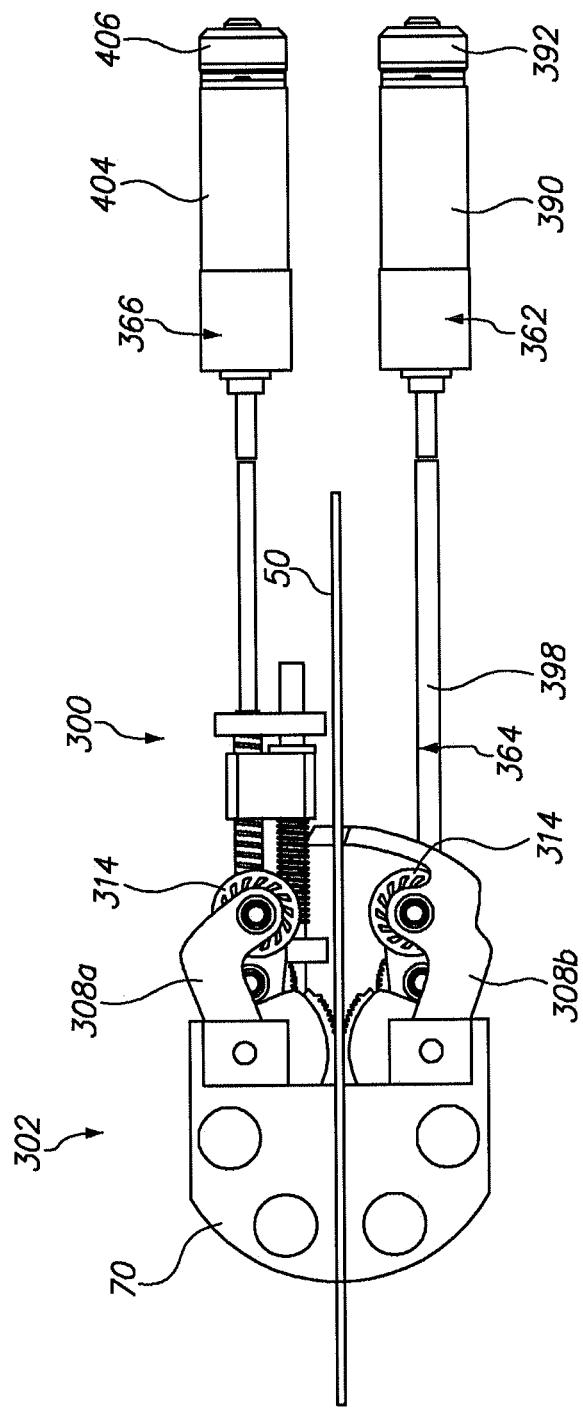
FIG. 30 a top view of the catheter feeder of FIG. 27, particularly showing the catheter feeder in the opened position.

Just prior to transitioning the jaw assembly 120a from the closed position to the opened position during its translation in the first axial direction 170 (the jaw assembly 120a is completing the middle stage of its front stroke), the jaw assembly 120c is transitioned from the opened position to the closed position while translating in the first axial direction 170, thereby taking over the leader catheter advancement function from the jaw assembly 120a (the jaw assembly 120c completes the end stage of its rear stroke and the initial stage of its front stroke, and is initiating the middle stage of its front stroke), and the second jaw assembly 120a is transitioning from the opened position to the closed position while continuing to be translated in the second axial direction 172, thereby readying it to take over the leader catheter advancement function from the jaw assembly 120c (the jaw assembly 120a completes the end stage of its front stroke and the initial stage of its rear stroke, and is in the end stage of its rear stroke) (see FIG. 26d).

Rotation of the cam shaft 158 may continue to be rotated in the first rotational direction 166 to repeat the previous steps, thereby further advancing the leader catheter 38 within the guide sheath 36. Thus, it can be appreciated that the leader catheter 38 can be continuously advanced within the guide sheath 36 via continuous rotation of the cam shaft 158 in the first rotational direction 166.

To retract the leader catheter 38 within the guide sheath 36, the cam shaft 158 is continuously rotated in the second rotational direction 168 via operation of the motor to mimic the manual finger retract method that physicians may use to retract the leader catheter 38 within the guide sheath 36. In particular, the same manipulation steps described above with respect to the advancement of the leader catheter 38 are performed, with the caveat that the front stroke occurs in the second axial direction 172, and the rear stroke occurs in the first axial direction 170.

Referring to FIG. 27-50, another embodiment of an active catheter feeder 300 will now be described. Unlike the catheter feeder 100 which utilizes opposing gripping pads that are linearly translated to actively advance/retract the leader catheter 38 within the guide sheath 36, the catheter feeder 300 utilizes opposing gripping pads that are rotated to actively advance/retract the leader catheter 38 within the guide sheath 36. The catheter feeder 300 is integrated into the housing 68 of the instrument driver 34.

To this end, and with reference to FIGS. 27-30, the catheter feeder 300 generally comprises a disposable rotatable gripper assembly 302 for performing advancing/retracting movements of the leader catheter 38 within the guide sheath 36, a driver assembly 304 configured for actuating the rotatable gripper assembly 302 to perform these movements, and a drape 306 (shown in FIGS. 39 and 40) configured for isolating the disposable components of the catheter feeder 300 from the sterile field.

The rotatable gripper assembly 302 is mounted to the outside of the housing 68 of the instrument driver 34 between the sheath drive block 74 and the catheter carriage 76, and in particular, may be mounted to the same mounting plate 70 (as the base plate) on which the proximal adapter 48 is mounted. In contrast, the driver assembly 114 is contained within the housing 68 of the instrument driver 34.

Referring further FIGS. 31, 32, 42, and 43, the rotatable gripper assembly 302 includes an upper pair of upper opposable arms 308a, 308b pivotably mounted to a base (and in this case the mounting plate 70) via respective rods 310, a pair of vertical shafts 312 rotatably mounted to the respective upper arms 308a, 308b, and a pair of rotatable gripping pads 314 respectively mounted to the vertical shafts 312.

The base 316 of each of the upper arms 308 includes a bore 318 through which the rod 310 is mounted. The rods 310 are rotatably mounted within respective apertures (not shown) within the mounting plate 70, such that the upper arms 308 are pivotably mounted to the mounting plate 70. In the illustrated embodiment, both arms 308 are capable of alternatively pivoting toward each other to grip the catheter body 50 (see FIGS. 31 and 42) and away from each other to release the catheter body 50 (see FIGS. 32 and 43). Alternatively, only one of the upper arms 308a is capable of pivoting toward or away from the other arm 308b, which in this case, the other arm 308b cannot pivot relative to the mounting plate 70.

Figure 31:
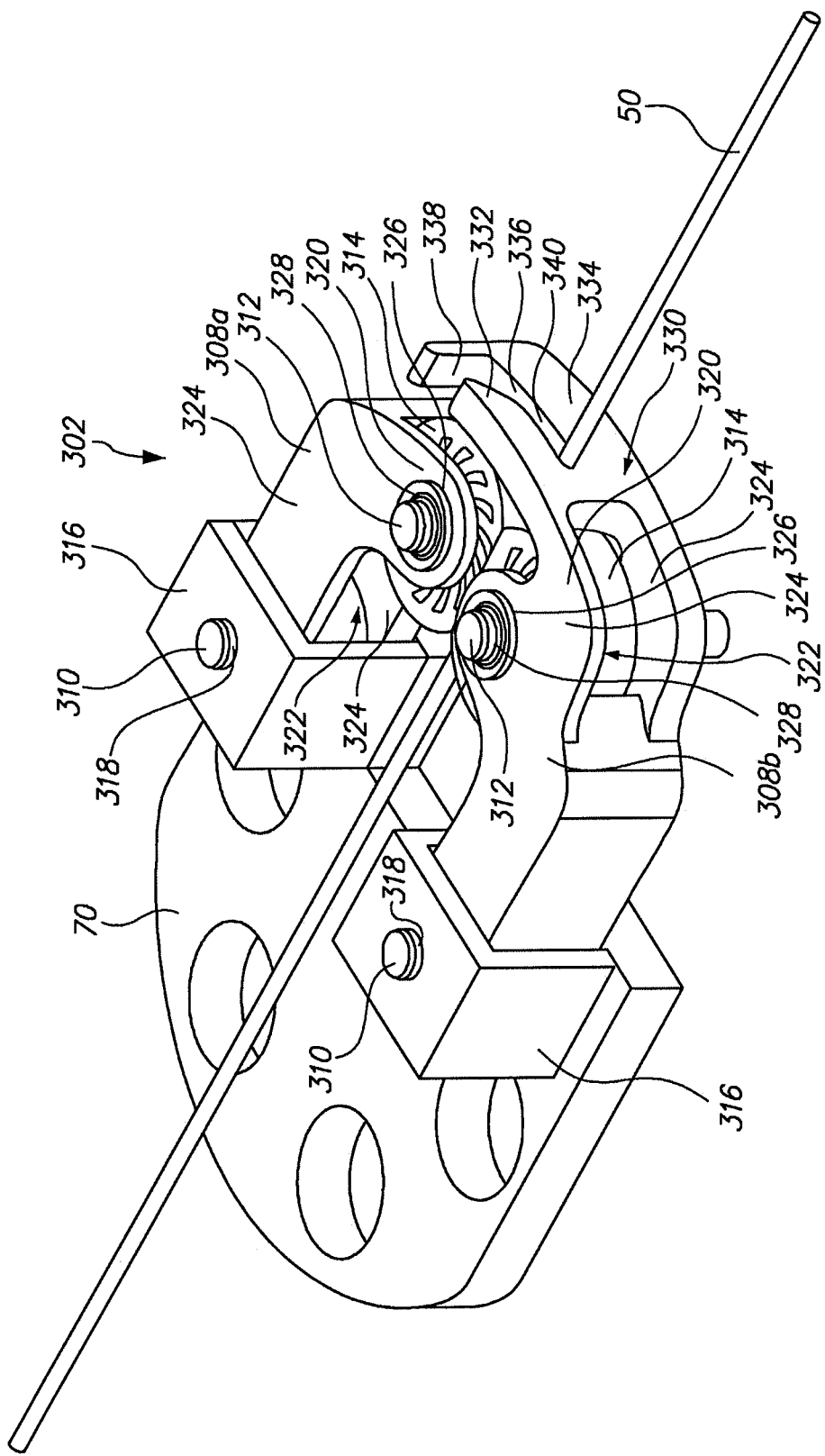
FIG. 31 is a perspective view of a rotatable gripper assembly used in the catheter feeder of FIG. 27, particularly showing the rotatable gripper assembly in a closed position.
Figure 32:
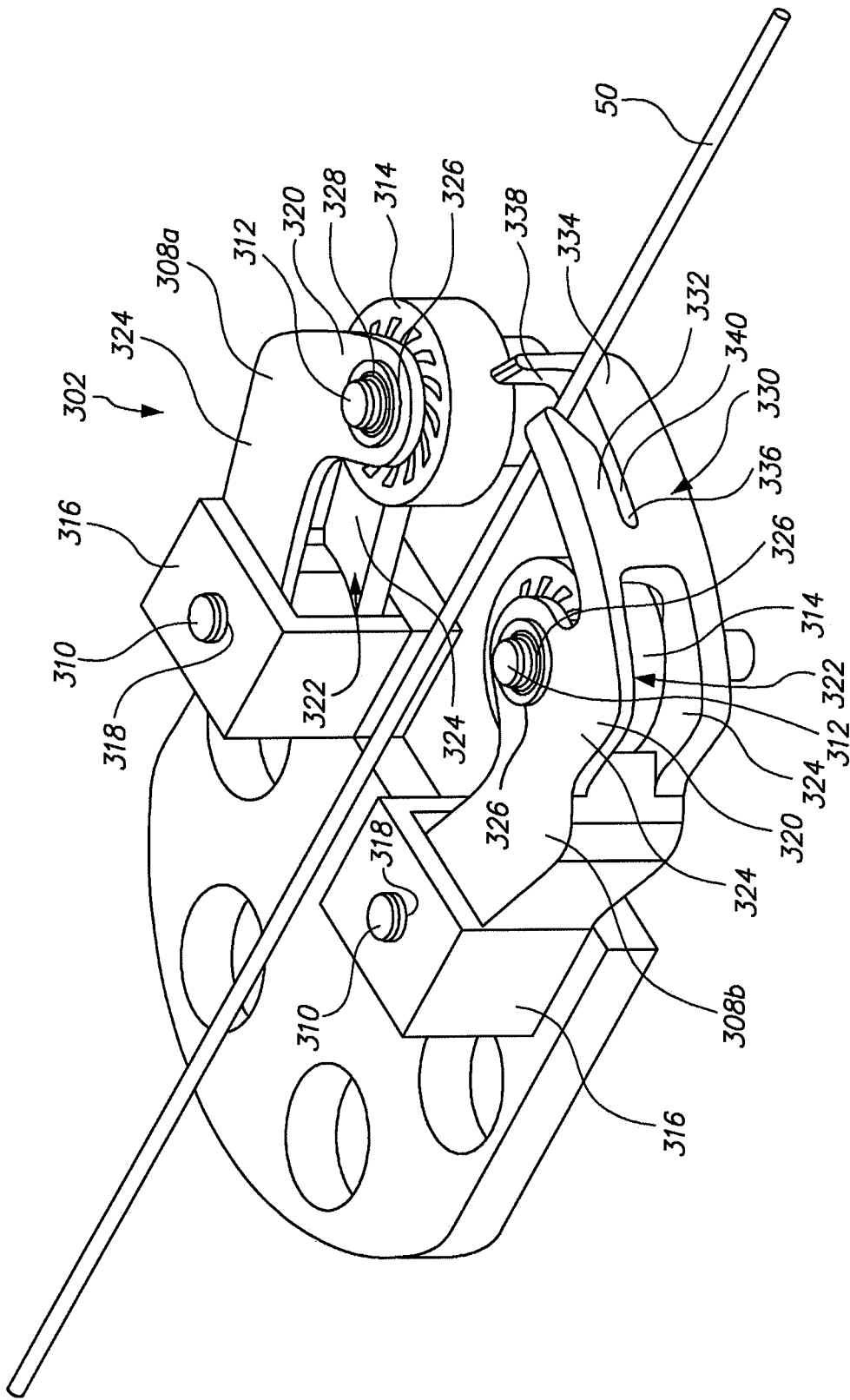
FIG. 32 is a perspective view of the rotatable gripper assembly of FIG. 31, particularly showing the rotatable gripper assembly in an opened position.
Figure 33:
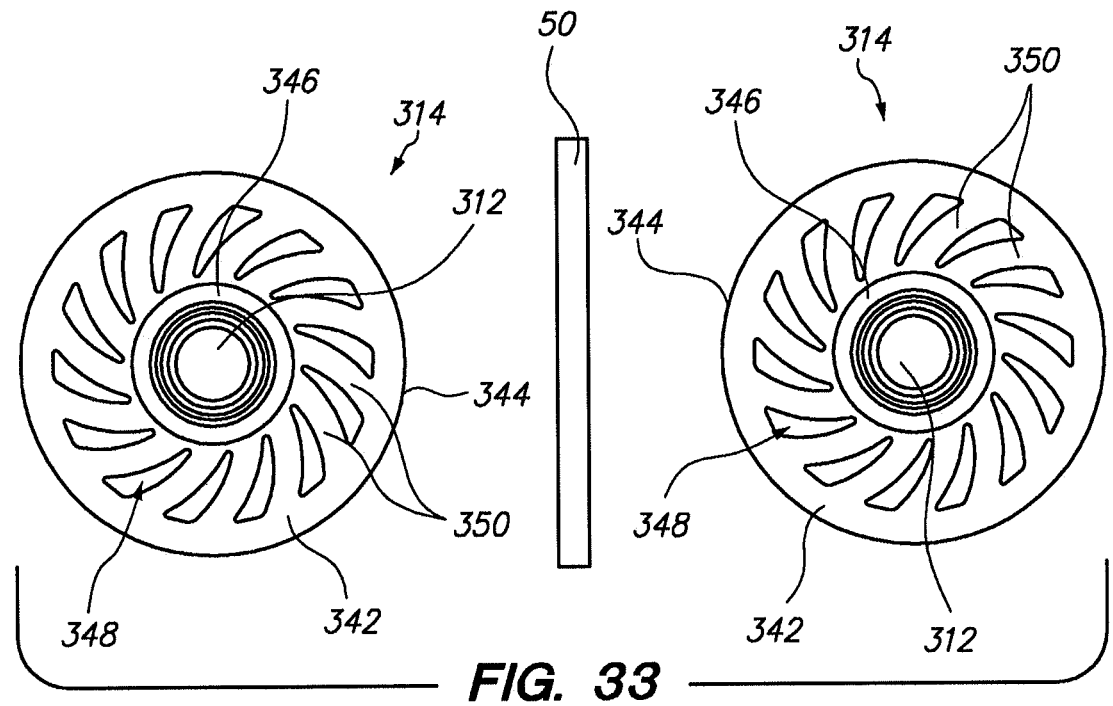
FIG. 33 is a top view of a pair of rotatable gripping pads used in the rotatable gripper assembly of FIG. 31, particularly showing the pair of rotatable gripping pads in an opened position.

The end 320 of each of the upper arms 308 curves inward and include a horizontal cavity 322 formed between a pair of horizontal flanges 324 in which the respective rotatable gripping pad 314 is disposed. The end 320 of each of the upper arms 308 further includes a pair of bearing apertures 326 formed through the respective horizontal flanges 324 and a pair of bearing rings 328 disposed within the respective bearing apertures 326 (only the apertures 326 and bearing rings 328 in the top horizontal flanges 324 are shown in FIGS. 31 and 32). Each vertical shaft 312 is rotatably mounted through the pair of bearing rings 328 disposed in the respective arm 308, so that each rotatable gripping pad 314 is rotatably mounted in the horizontal cavity 322 of the respective arm 308.

It can be appreciated that the upper arms 308, when completely pivoted away from each other, allow the catheter body 50 to be top loaded into the catheter feeder 300; that is, the catheter body 50 can simply be laterally placed (dropped in) between the rotatable gripping pads 314. It can be also be appreciated that the upper arms 308 can be pivoted toward each other, such that the catheter body 50 can be gripped between the rotatable gripping pads 314 (see FIGS. 31 and 42), and pivoted away from each other, such that the catheter body 50 can be released from between the rotatable gripping pads 314 (see FIGS. 32 and 43). Furthermore, the opposing rotation of the rotatable gripping pads 314, when the catheter body 50 is gripped therebetween, advances or retracts the leader catheter 38 within the guide sheath 36. Significantly, continuous rotation of the rotatable gripping pads 314 provides for infinite advancement/retraction range of actuation for the leader catheter 38.

Figure 42:
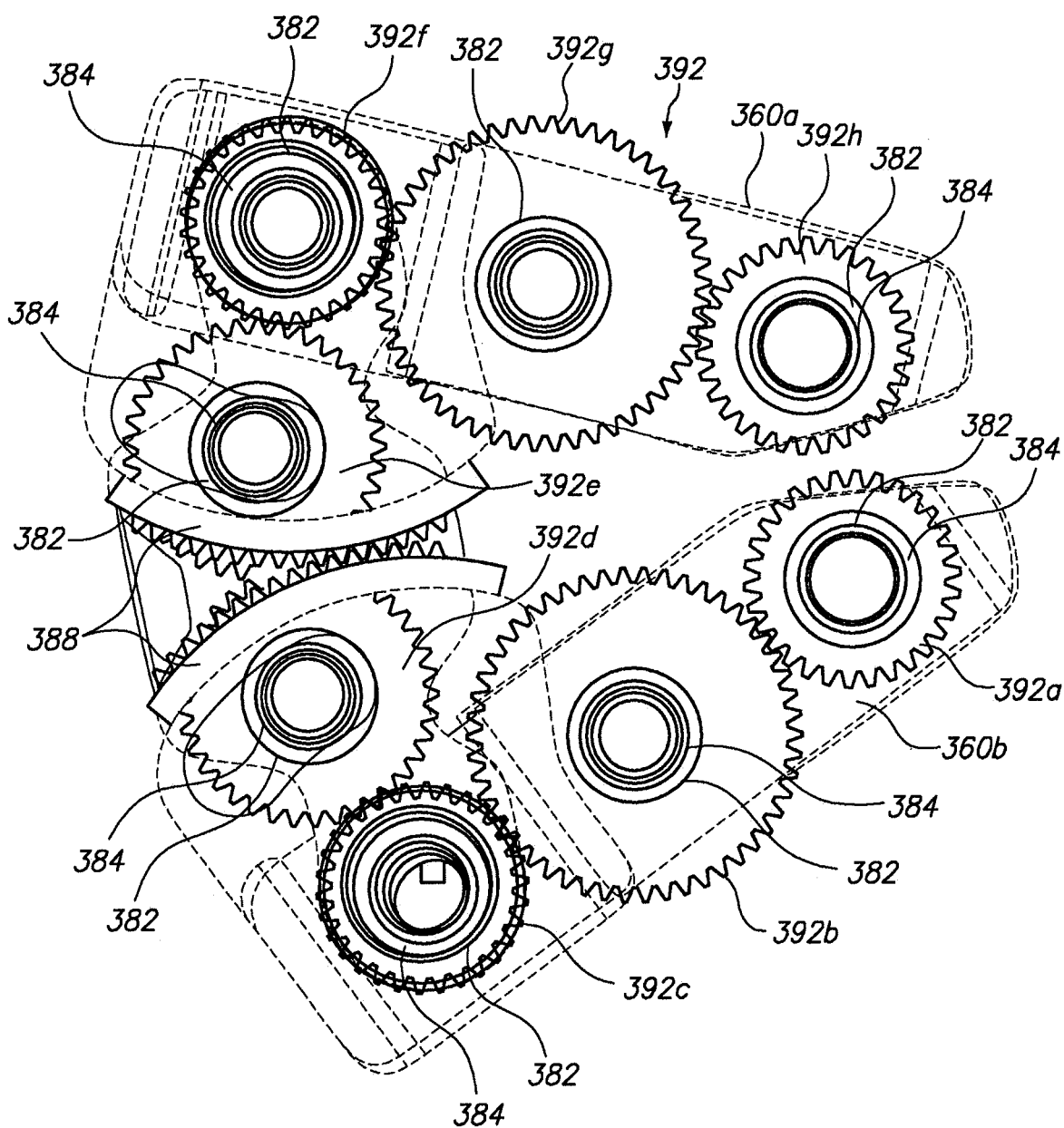
FIG. 42 is a top view of a gear assembly used in the pair of lower arms of the driver assembly used in the catheter feeder of FIGS. 27-30, particularly showing the pair of lower arms in the closed position.
Figure 43:
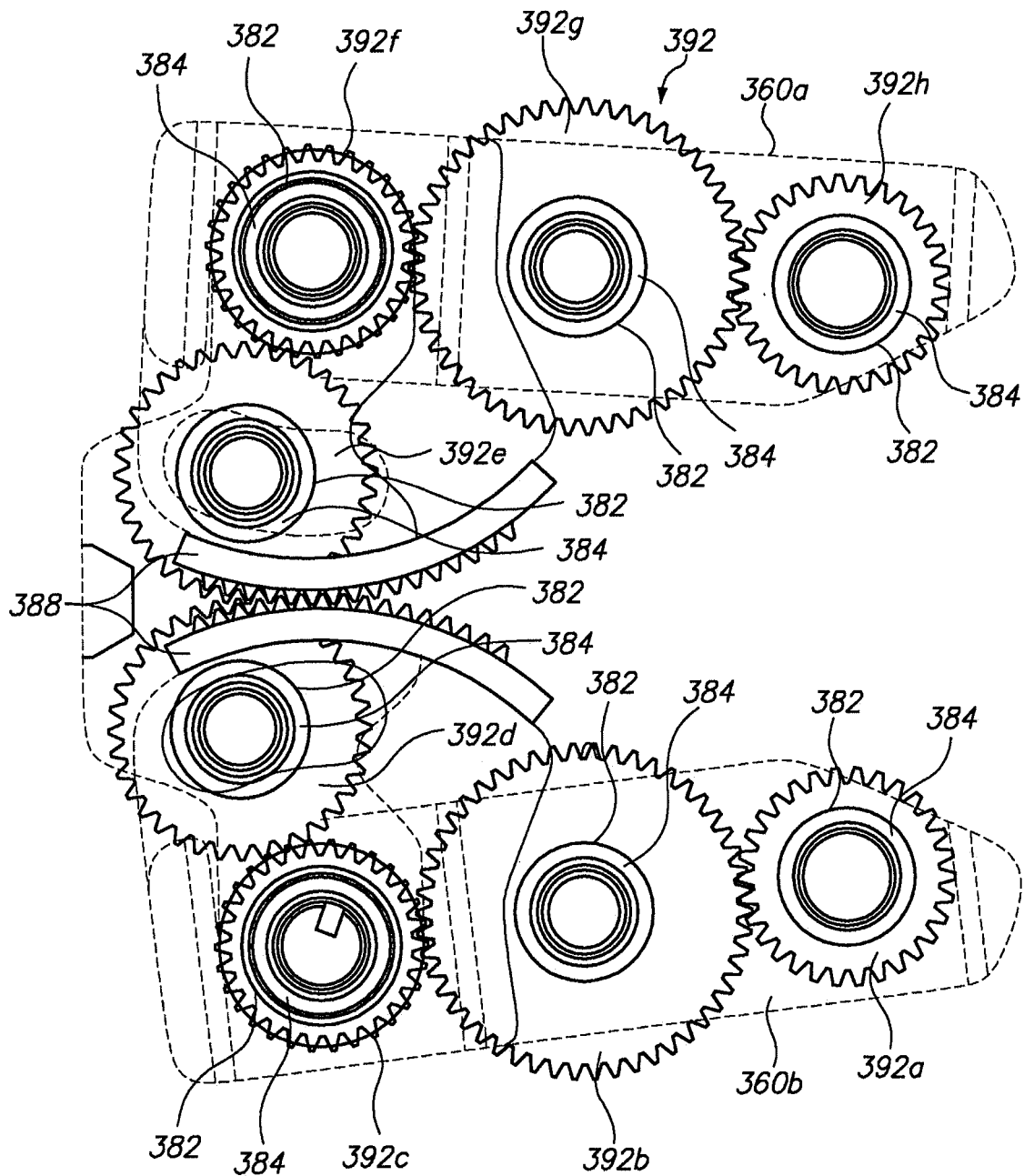
FIG. 43 is a top view of a gear assembly used in the pair of lower arms of the driver assembly used in the catheter feeder of FIGS. 27-30, particularly showing the pair of lower arms in the opened position.
Figure 44:
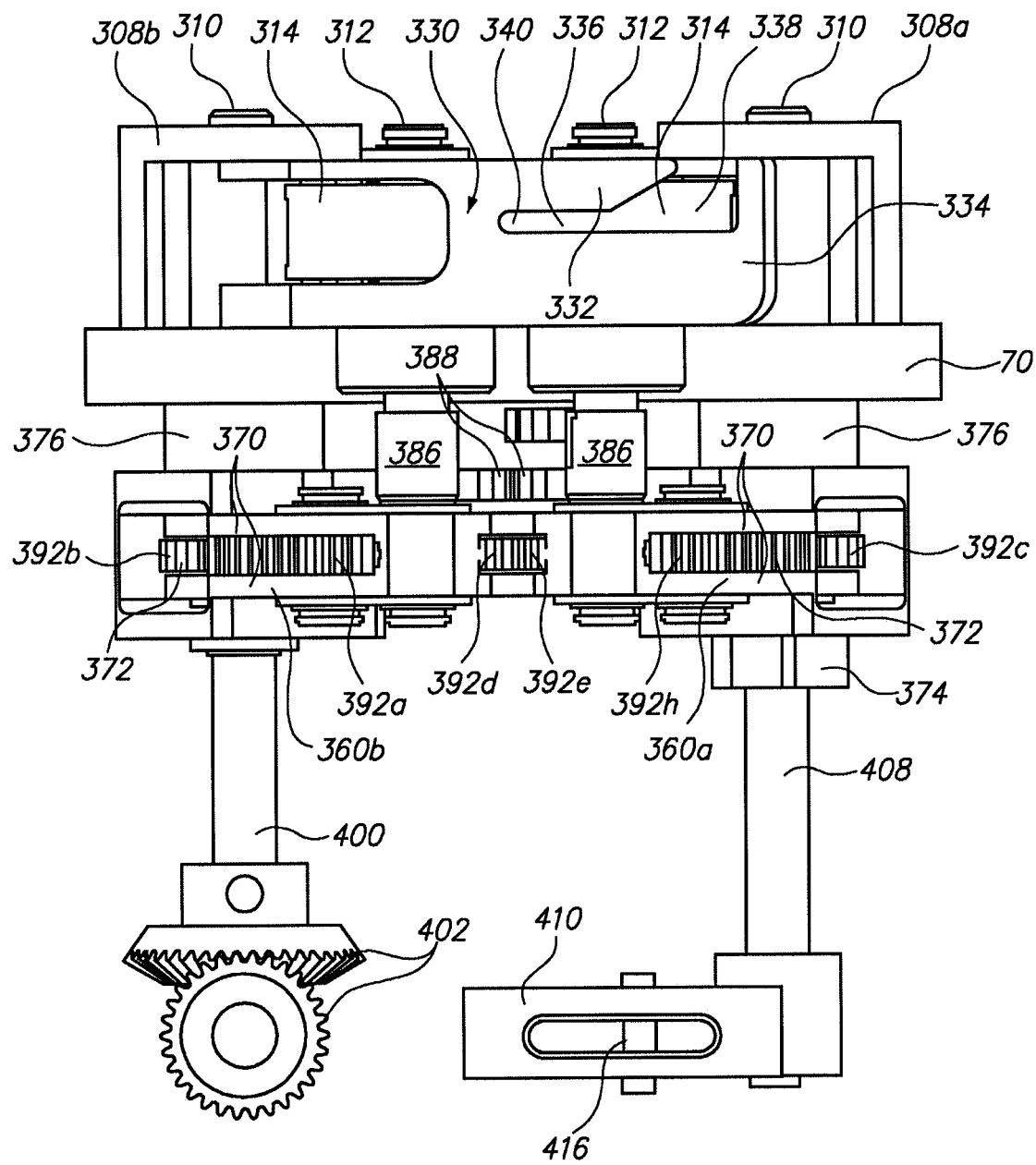
FIG. 44 is a front view of the catheter feeder of FIGS. 27-30, particularly showing the catheter feeder in the closed position.
Figure 45:
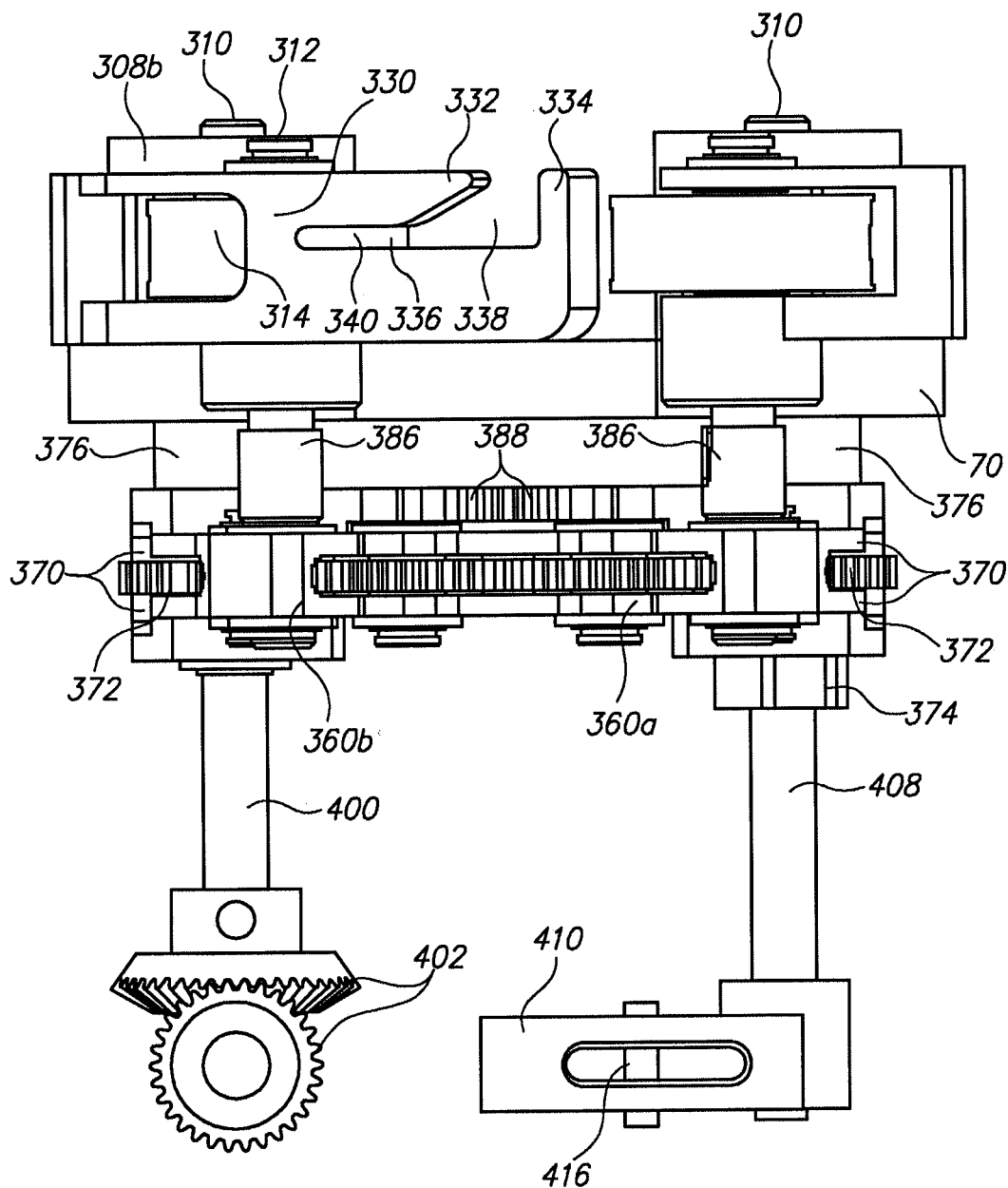
FIG. 45 is a front view of the catheter feeder of FIGS. 27-30, particularly showing the catheter feeder in the opened position.

To vertically center the catheter body 50 between the rotatable gripping pads 314, the end 320 of one of the upper arms 308 (in this case, the upper arm 308b) further includes a claw feature 330 having an upper straight flange 332, a lower L-shaped flange 334, and an L-shaped slot 336 formed between the flanges 332, 334. The catheter body 50 can be top loaded into a vertical portion 338 of the L-shaped slot 336, and then laterally slid into a horizontal portion 340 of the L-shaped slot 336 to conveniently locate the catheter body 50 between the rotatable gripping pads 314. Thus, when the upper arms 308 are completely pivoted toward each other, as shown in FIGS. 31 and 42, the slotted geometry vertically constrains the catheter body 50, while the rotatable gripping pads 314 horizontally constrain the catheter body 50.

Figure 34:
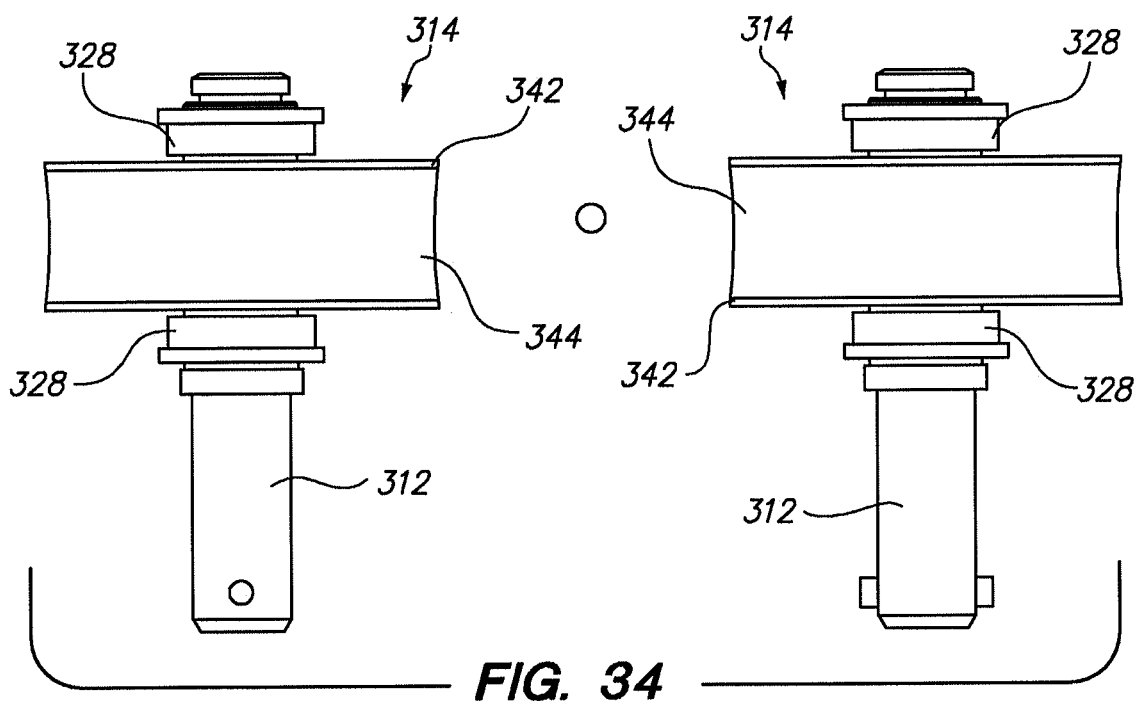
FIG. 34 is a side view of the pair of rotatable gripping pads of FIG. 33, particularly showing the pair of rotatable gripping pads in the opened position.
Figure 35:
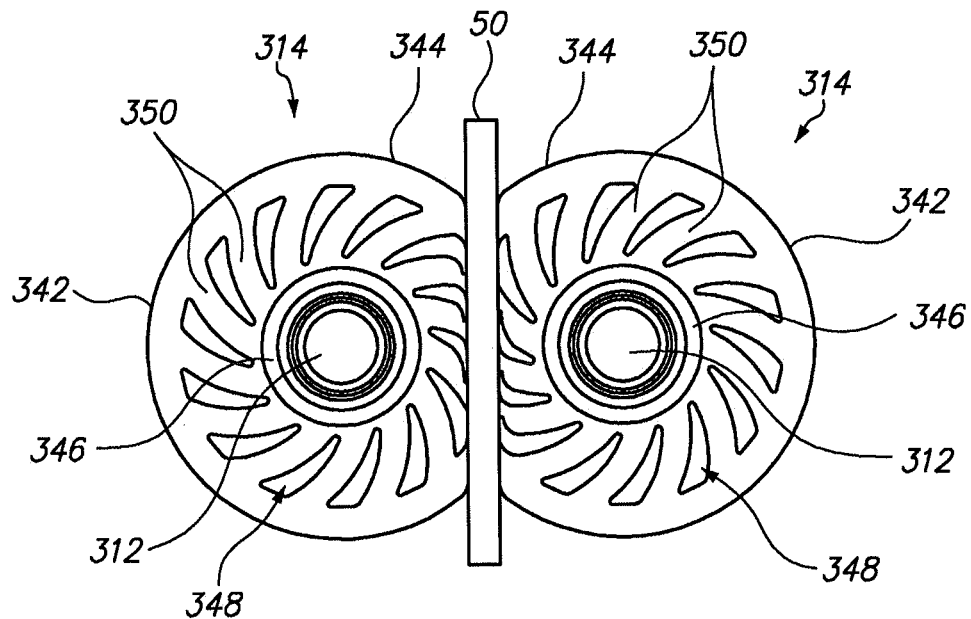
FIG. 35 is a top view of the pair of rotatable gripping pads of FIG. 33, particularly showing the pair of rotatable gripping pads in a closed position.

Significantly, the rotatable gripping pads 314 are specially designed to distribute the gripping force applied to the catheter body 50, thereby preventing pinching. As such, a relatively large gripping force can be applied to the catheter body 50 to prevent slippage, as well as to compensate for varying catheter diameters. In particular, as shown in FIGS. 33-36, each rotatable gripping pad 314 includes an outer circular rim 342 with a gripping surface 344, a center hub 346 to which the respective vertical shaft 312 is mounted, and a framework 348 disposed between the circular rim 342 and the center hub 346. The frameworks 348 of the respective rotatable gripping pads 314 are configured for partially collapsing in response to the gripping force generated when the arms 308 are pivoted toward each other, such that the portions of the rims 342 that oppose each other flatten to contact each other along an extended line of contact to distribute the gripping force. The rotatable gripping pads 314 essentially deform to a D-shape, as best shown in FIG. 35. In the illustrated embodiment, each of the frameworks 348 includes a plurality of spokes 350 extending between the center hub 346 and the circular rim 342. All of the spokes 350 are curved in the same direction, such that they collapse onto each other in response to the gripping force, and in particular, bend and stack on top of each other. In alternative embodiments, other types of frameworks, such as a honeycomb pattern, may be used; however, the simple spoke design is more easily manufacturable.

Figure 36:
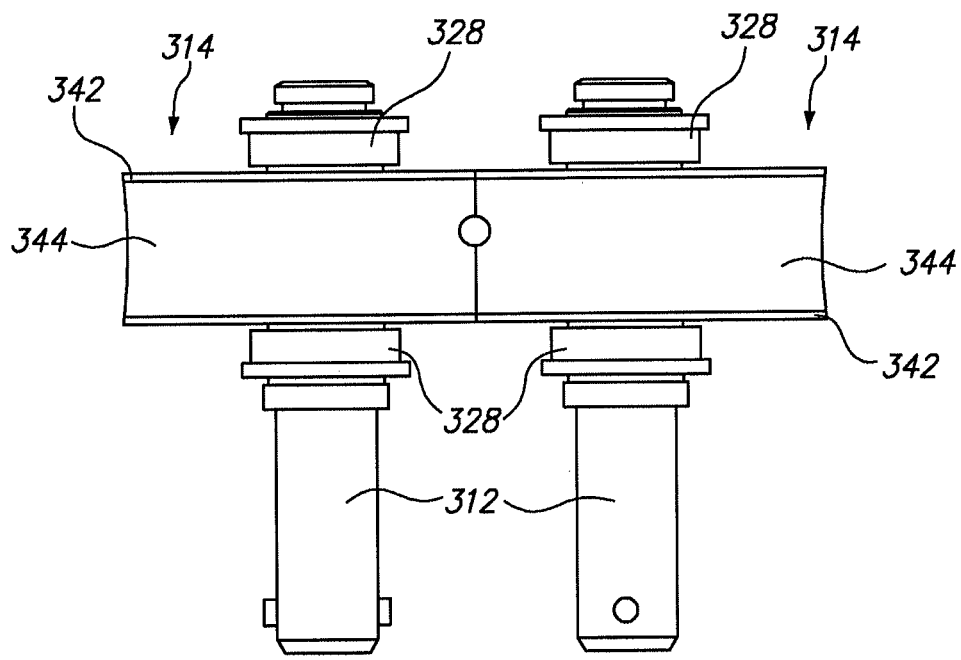
FIG. 36 is a side view of the pair of rotatable gripping pads of FIG. 33, particularly showing the pair of rotatable gripping pads in the closed position.

The thickness of the spokes 350 is preferably within a range that facilitates their collapse in response to minimal gripping force. For example, each spoke 350 may have a thickness in the range of 0.010-0.050 inches. In the illustrated embodiment, each spoke 350 has a 0.040 inch thickness. The circular rim 342 and framework 348 may be overmolded on the hub 346, and may be composed of a suitable material, such as rubber. The durometer/hardness of the material is preferably high enough to endure high friction (preferably at least 50 A), while being low enough to facilitate collapsing of the spokes 350 and circular rim 342 in the presence of the gripping force. A thermoplastic polyurethane, such as Texin® RxT70A, is ideal for high friction applications and is further gamma compliant. Each rotatable gripping pad 314 preferably has a diameter of two inches or less and a width of less than one inch. In the illustrated embodiment, each rotatable gripping pad 314 has a 1.0 inch diameter and a 0.38 inch width. Thus, it can be appreciated that in comparison to a rotatable gripping pad composed of soft rubber where a lot of gripping force is required to compress and create a small amount of contact, and thus small gripping force, between the rotatable gripping pads, the architecture of the rotatable gripping pads 314 provides a large gripping force without pinching the catheter body 50. In essence, the rotatable gripping pads 314 collapse as opposed to compress as with solid rotatable gripping pads. As best shown in FIGS. 34 and 36, the gripping surfaces 344 of the respective rims 342 may be concave in order to facilitate vertical centering of the catheter body 50 between the rotatable gripping pads 314.

Figure 37:
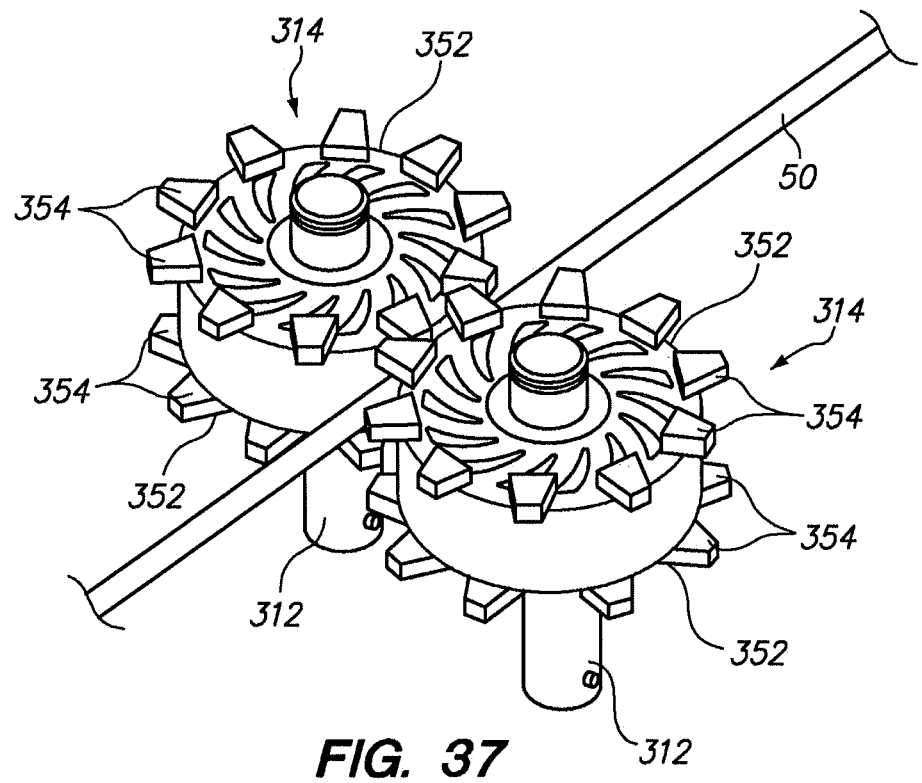
FIG. 37 is a perspective view of an optional pair of rotatable gripping pads used in the rotatable gripper assembly of FIG. 31, particularly showing the pair of rotatable gripping pads in a closed position.
Figure 38:
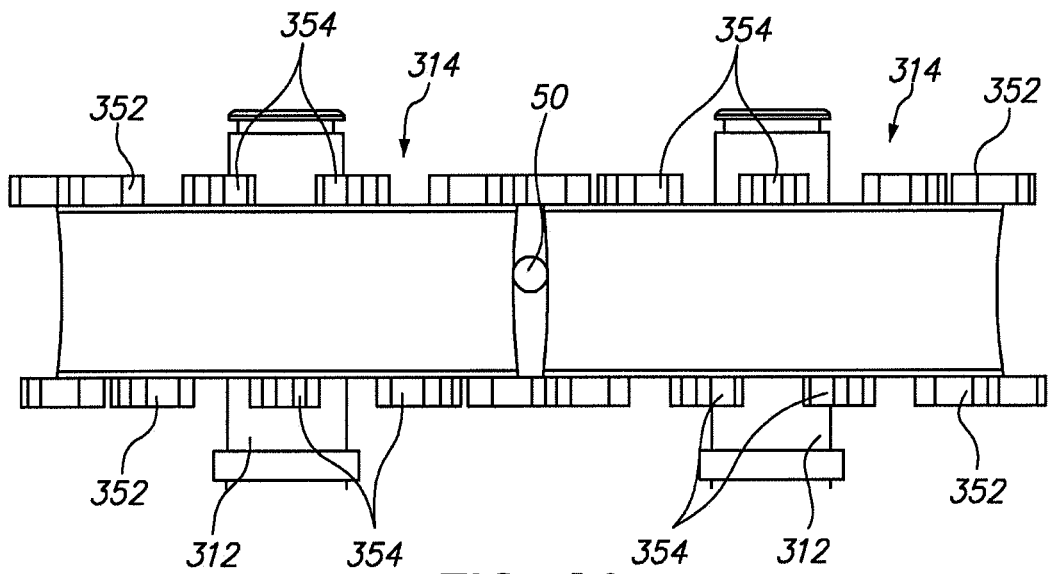
FIG. 38 is a side view of the pair of rotatable gripping pads of FIG. 37, particularly showing the pair of rotatable gripping pads in the closed position.

As shown in FIGS. 37 and 38, each of the rotatable gripping pads 314 may optionally include a pair of upper and lower sprockets 352 mounted to the opposing flat upper and lower surfaces of the respective rotatable gripping pad 314. Each sprocket 352 includes a plurality of circumferentially disposed teeth 354. As such, the upper sprockets 352 of the rotatable gripping pads 314 interlace or mesh with each other, and the lower sprockets 352 of the rotatable gripping pads 314 interlace or mesh with each other. In this manner, the catheter body 50 is prevented from slipping out from between the rotatable gripping pads 314, which might otherwise occur due as a result of inconsistent pressure across the width of the rotatable gripping pads 314 due to their collapsing nature. In the illustrated embodiment, the rotatable gripping pads 314, including the sprockets 352, are composed of a homogenous material, so that deformation of the sprockets 352 tracks with the deformation of the rims 342 and spokes 350 of the respective rotatable gripping pads 314. In an alternative embodiment, the sprockets 352 are composed of a material that is more rigid than the material of which the circular rim 342 and spokes 350 is composed. In this manner, one of the rotating rotatable gripping pads 314 may drive the other rotatable gripping pad 314 to rotate it.

Figure 39:
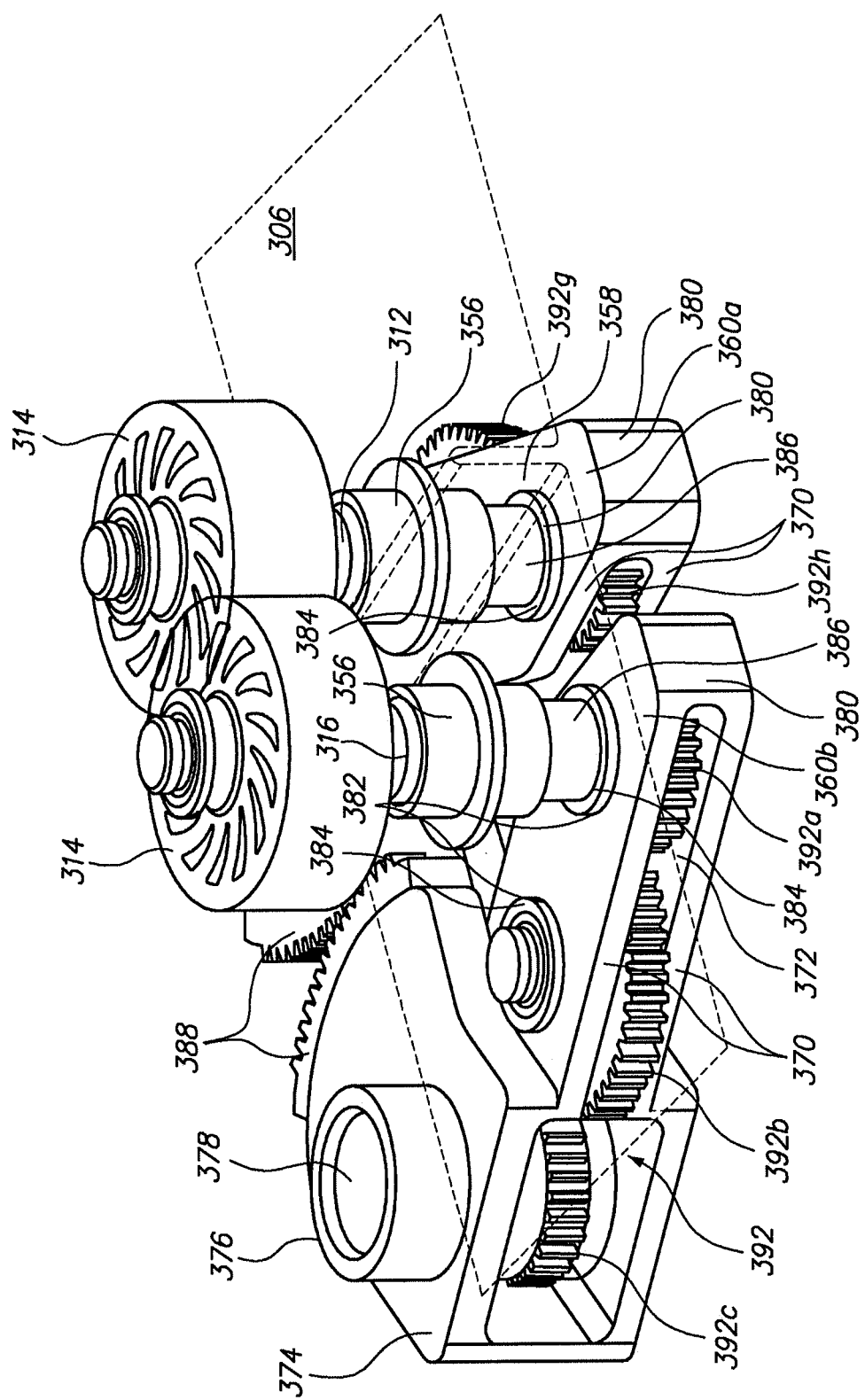
FIG. 39 is a perspective view of a pair of lower arms of a driver assembly used in the catheter feeder of FIG. 27, particularly showing the pair of lower arms in a closed position.
Figure 40:
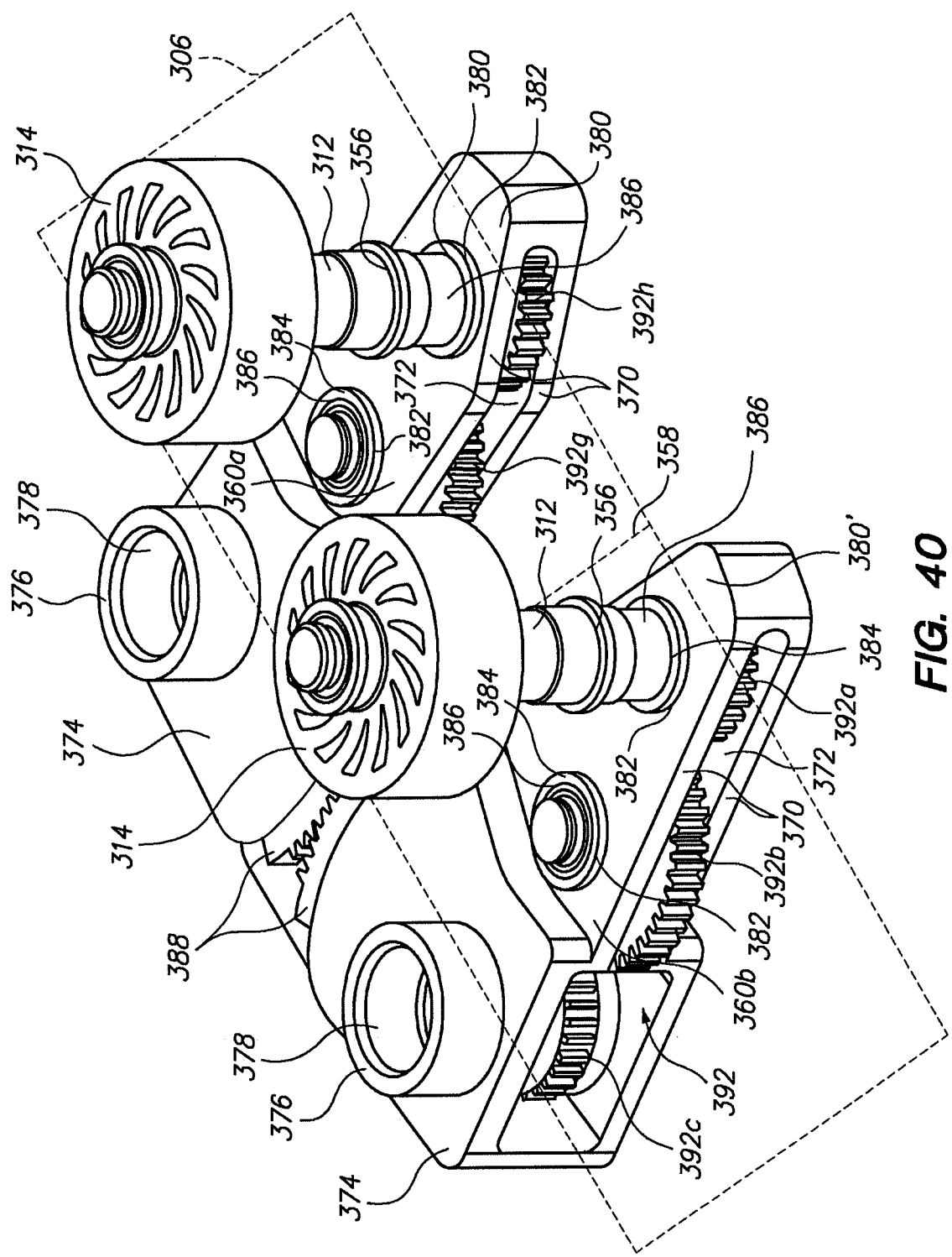
FIG. 40 is a perspective view of the pair of lower arms of FIG. 39, particularly showing the pair of lower arms in an opened position.
Figure 41:
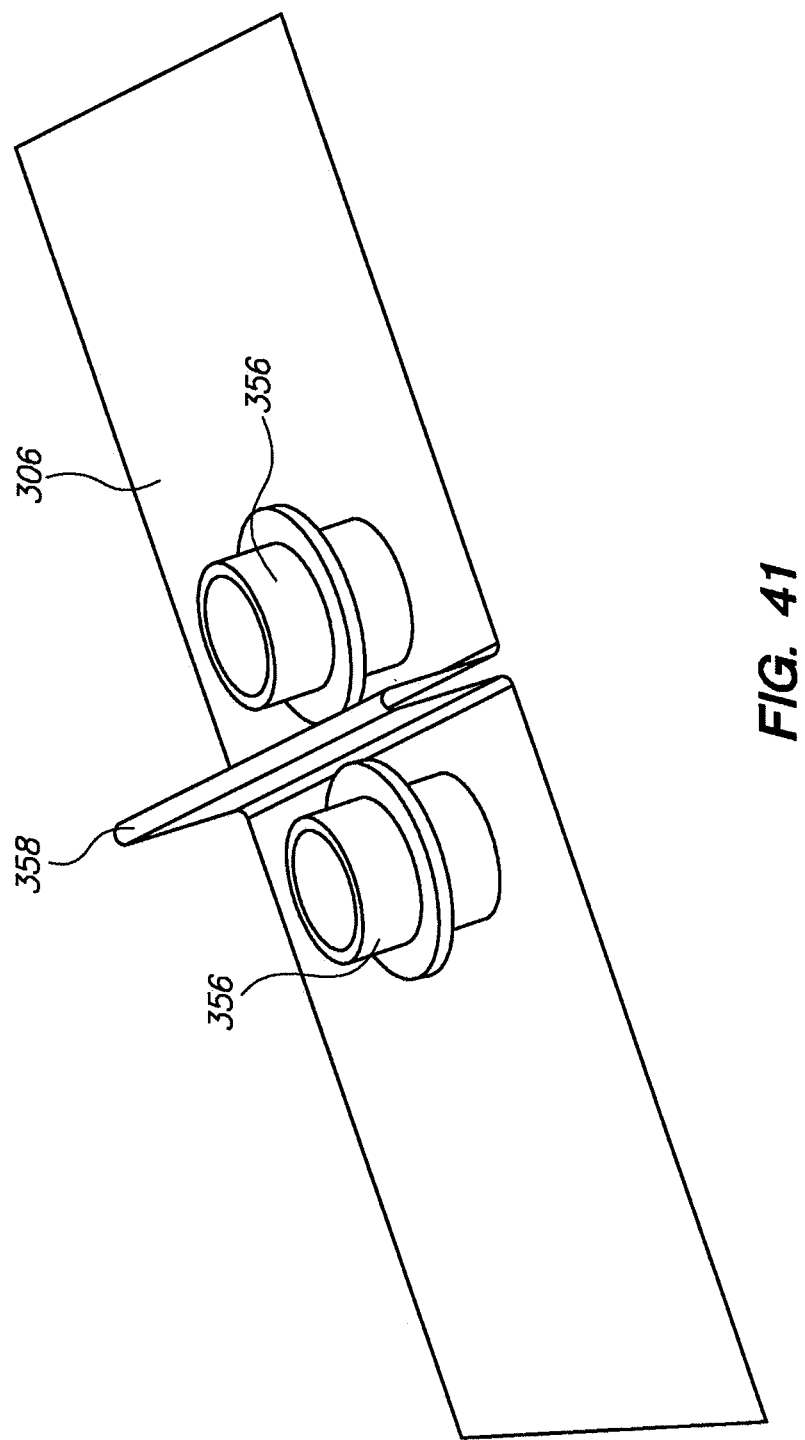
FIG. 41 is a perspective view of a drape used to mate the rotatable gripper assembly of FIG. 31 with a driver assembly used in the catheter feeder of FIGS. 27-30.
Figure 50:
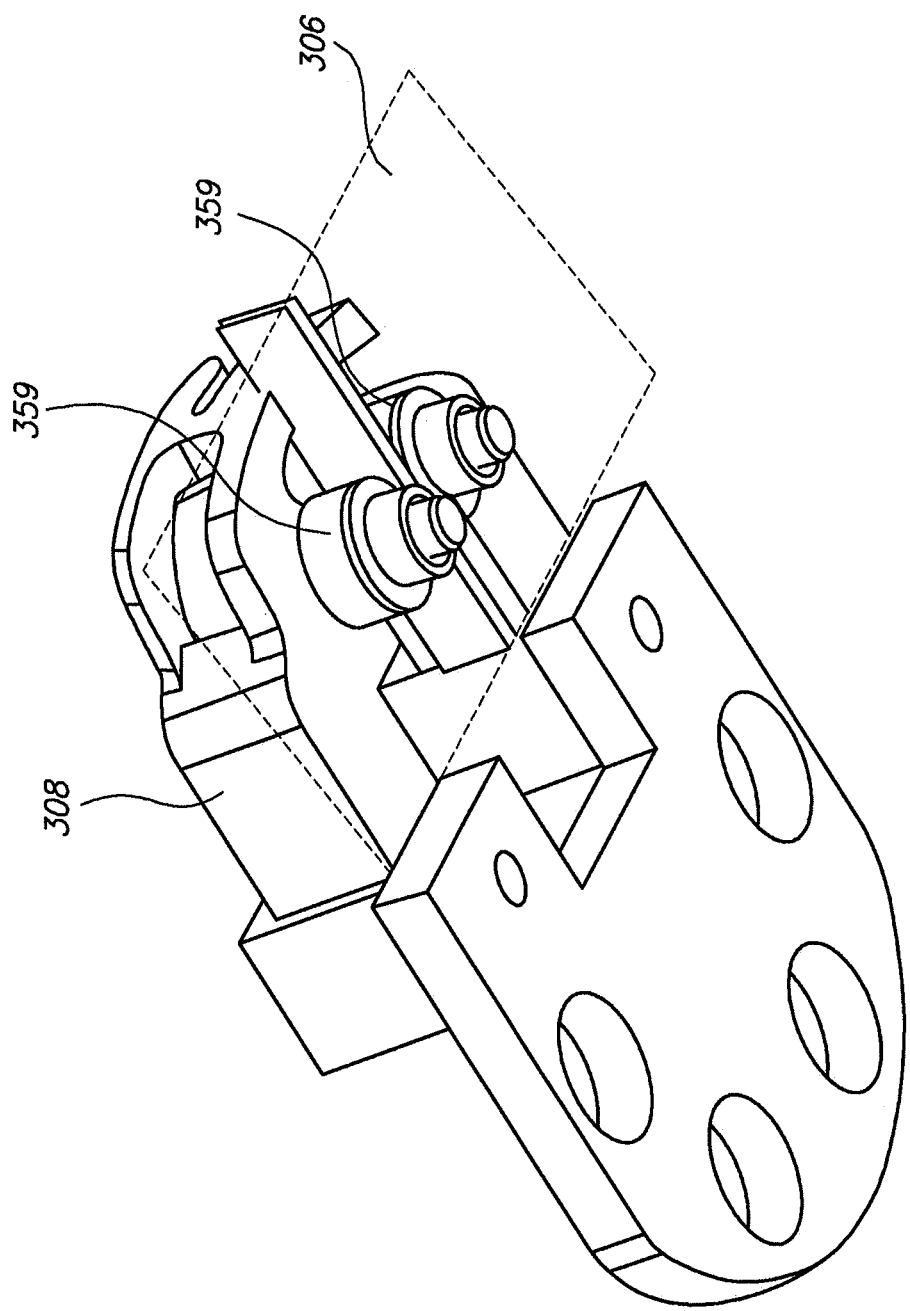
FIG. 50 is a perspective view of the mating of the rotatable gripper assembly of FIG. 31 to the drape.

Pivoting of the upper arms 308 and rotation of the rotatable gripping pads 314 are actuated via the driver assembly 304. Referring now to FIGS. 39-41, the rotatable gripper assembly 302 is configured for interfacing with the driver assembly 304 via the sterile drape 306 surrounding the housing 68. In particular, the sterile drape 306 includes a pair of plugs 356 capable of being respectively disposed over a pair of collars 386 of the driver assembly 304. The vertical shafts 312 of the rotatable gripper assembly 302 may then be respectively slipped through the plugs 356 and into the collars 386 of the driver assembly 304. The end of each of the vertical shafts 312 includes a keyed feature, such as a boss or cross pin, that engages a corresponding keyed feature in respective apertures in the collars 386. As will be described in further detail below, the driver assembly 304 rotates the collars 386 in opposing directions to correspondingly rotate the rotatable gripping pads 314 in opposite directions, as well as alternately displacing the collars 386 toward and away from each other to correspondingly pivot the upper arms 308 toward and away from each other. The sterile drape 306 folds or collapses between the plugs 356 when the arms 308 are pivoted towards each other (i.e., the plugs 356 are translated toward each other) (see FIG. 39), and unfolds or expands when the arms 308 are pivoted away from each other (i.e., the plugs 356 are translated away from each other) (see FIG. 40). To facilitate its folding/collapsing or unfolding/expansion, the sterile drape 306 includes an expansion joint 358 between the plugs 356. As best shown in FIG. 50, the upper arms 308 respectively include bosses 359 that respectively slip over the plugs 356 (not shown in FIG. 50) to create a labyrinth seal, thereby preventing fluid ingress into the housing 68.

As shown in FIGS. 27-30, the driver assembly 304 generally comprises a pair of lower opposable arms 360a, 360b configured for being actuated to pivot the respective upper arms 308a, 308b and to rotate the rotatable gripping pads 314 of the rotatable gripper assembly 302, a first motor assembly 362, a drive train 364 operably coupled between the first motor assembly 362 and the lower opposable arms 360a, 360b, a second motor assembly 366, and a gripping force adjustment mechanism 368 operably coupled between the second motor assembly 366 and the lower opposable arms 360a, 360b.

Referring back to FIGS. 39 and 40, each of the lower arms 360 includes a pair of horizontal flanges 370 and a horizontal cavity 372 formed between the horizontal flanges 370. The base 374 of each of the lower arms 360 further includes a boss 376 formed on the top horizontal flange 370 and a bearing aperture 378 formed within the boss 376. Each of the two rods 310 of the rotatable gripper assembly 370 includes a boss (not shown) that is rotatably mounted within the bearing aperture 372 of the respective lower arm 360, so that the lower arms 360 are pivotably mounted to the respective rods 310. Thus, the lower arms 360 may alternately pivot toward (see FIG. 39) and away (see FIG. 40) from each other about the vertical rods 310.

The end 380 of each of the lower arms 360 further includes a pair of bearing apertures 382 formed through the respective horizontal flanges 370 and a pair of bearing rings 384 disposed within the respective bearing apertures 382 (only the apertures 382 and bearing rings 384 in the top horizontal flanges 370 are shown in FIGS. 39 and 40). The ends 380 of the respective lower arms 360 further includes the previously described collars 386 to which the respective vertical shafts 312 of the rotatable gripper assembly 302 mate as discussed above. The collars 386 are rotatably mounted through the respective bearing rings 384 of the top horizontal flanges 370. In this manner, pivoting of the each of the lower arms 360 correspondingly pivots the respective upper arm 308 to which it is coupled via the mating arrangement of the vertical shaft 312 and collar 386. The lower arms 360 respectively pivot about the same axes as the upper arms 308, such that the upper arms 308 will pivot in unison with the lower arms 360. As will be described in further detail below, one of the lower arms 360, and in this case, the lower arm 360a, is driven to alternately pivot towards and away from the other lower arm 360b. The bases 374 of the lower arms 360 engage each other via section gears 388 that engage each other, such that the other lower arm 360b pivots in a direction opposite to the direction in which the lower arm 360a pivots. In effect, the lower arm 360a pivots the other lower arm 360b in the opposite direction via the section gears 388.

As shown in FIGS. 27-30, the first motor assembly 362 comprises a motor 390, a motor mount (not shown) in which the motor 390 is mounted, and an electrical connector 392 configured for coupling the cable 24 to the electronics within the motor 390, thereby allowing the motor 390 to be controlled via the control station 16. The drive train 364 is coupled between the motor 390 and the lower arms 360 in a manner that rotates the collars 386, and thus the rotatable gripping pads 314 of the rotatable gripper assembly 302, in opposite directions.

To this end, and with reference to FIGS. 39, 40, and 42-46, the drive train 364 comprises a gear assembly 392 disposed within the horizontal cavities 372 of the lower arms 360. The gear assembly 392 includes an even number of gears to create opposing motion in the rotatable gripping pads 314 via rotation of the collars 386 and corresponding rotation of the vertical shafts 312. In particular, the gear assembly 392 includes eight gears 392a-392h arranged in a linear cluster within the horizontal cavities 372 of the lower arms 360. Four of the gears (gears 392e-392h) are located in the lower arm 360a, and the other four gears (gears 392a-392d) are located in the lower arm 360b. Ultimately, the number of gears 392 will be dictated by the packaging of the lower arms 360 within the housing 68. Each of the gears 392a-392h are rotatably mounted within the lower arms 360 via a corresponding pair of bearing apertures 382 formed through the horizontal flanges 370 and the pair of bearing rings 384 disposed within the bearing apertures (bearing apertures and bearing rings not shown for the gears 392c and 392d).

The rotatable gripping pad gear 392a is coupled to the drive gear 392c via the gear 392b, such that rotation of the drive gear 392a rotates the gear 392b, which in turn rotates the rotatable gripping pad gear 392a. Likewise, the rotatable gripping pad gear 392h is coupled to the drive gear 392c via the gears 392d-392g, such that rotation of the drive gear 39ca rotates the gear 392d, which in turn rotates the gear 392e, which in turn rotates the gear 392f, which in turn rotates the gear 392g, which in turn rotates the rotatable gripping pad gear 392h. Because there is an even number of gears in the gear assembly 392, the rotatable gripping pad gears 392a, 392h, and thus the rotatable gripping pads 314, rotate in opposite directions when the drive gear 392c is rotated in either direction. It can be appreciated that rotation of the drive gear 392c in one direction 394 will cause the rotatable gripping pads 314 to rotate in a manner that advances the leader catheter 38 within the guide sheath 36, and rotation of the drive gear 392c in the opposite direction 396 will cause the rotatable gripping pads 314 to rotate in a manner that retracts the leader catheter 38 within the guide sheath 36. The middle gears 392b and 392g orbit about the respective gears 392c and 392f as the lower arms 360 pivot away or toward each other. In this manner, the rotatable gripping pad gears 392a, 392h will always maintain transmission during pivoting of the lower arms 360.

Referring back to FIGS. 27-30, the drive train 364 further comprises a drive shaft 398 to which the motor 390 is mechanically coupled, a vertical rod 400 to which the drive gear 392c is affixed, and a set of bevel gears 402 coupling the drive shaft 398 to the vertical rod 400. Thus, operation of the motor 390 rotates the drive shaft 398, which rotates the vertical rod 400, which in turn, rotates the drive gear 392c, thereby rotating the rotatable gripping pads 314, as described above.

The second motor assembly 366 comprises a motor 404, a motor mount (not shown) in which the motor 404 is mounted, and an electrical connector 406 configured for coupling the cable 24 to the electronics within the motor 404, thereby allowing the motor 404 to be controlled via the control station 16. The gripping force adjustment mechanism 368 is coupled between the motor 404 and the lower arms 360 in a manner that alternately pivots the upper arm 308a (via the lower arm 360a) in a first direction (i.e., toward the other upper arm 308b), such that the catheter body 50 can be gripped between the rotatable gripping pads 314, and in a second opposite direction (i.e., away from the other upper arm 308b), such that the catheter body 50 can be released from between the rotatable gripping pads 314. The gripping force adjustment mechanism 368 is also coupled between the motor 404 and the lower arms 360 in a manner that adjusts the gripping force of the upper arms 308 when gripping the catheter body 50.

To this end, and with reference to FIGS. 44-49, the gripping force adjustment mechanism 368 further comprises a linkage in the form of a vertical rod 408 affixed to the base 374 of the lower arm 360a, and a lever arm 410 affixed to the vertical rod 408, such that rotation of the lever arm 410 rotates the vertical rod 408 about its longitudinal axis, thereby placing a torque on the base 374 of the lower arm 360a, and pivoting the lower arm 360a (and thus the upper arm 308a) toward or away from the other lower arm 360b (and thus the other upper arm 308b). The gripping force adjustment mechanism 368 further comprises a horizontal rod 412 that is coupled to the lever arm 410. In particular, the lever arm 410 includes a through slot 414 in which a pin 416 can be translated via a pair of rotatable gripping pads 418 through which the pin 416 is mounted (only one of the rotatable gripping pads 418 shown). The end of the horizontal rod 412 includes an aperture (not shown) through which the pin 416 is affixed, such that translation of the horizontal rod 412 back and forth alternately pivots the lever arm 410 while the pin 416 translate within the through slot 414 via the rotatable gripping pads 418.

The gripping force adjustment mechanism 368 further comprises a lead screw 420, and a lead nut 422 having a first threaded bore 424 in which the lead screw 420 is in threaded engagement, and a second bore 426 in which the horizontal rod 412 is in bearing engagement. The gripping force adjustment mechanism 368 further comprises a compression spring 428 disposed about the horizontal rod 412 between a pair of annular flanges 430, 432, with the spring 428 being disposed about the horizontal rod 412 between the annular flanges 430, 432, and the lead nut 422 being disposed between the spring 428 and the annular flange 432. The gripping force adjustment mechanism 368 further comprises a pair of retaining devices 434 that maintain the horizontal rod 412 and the lead screw 420 in parallel arrangement with each other.

Thus, it can be appreciated that the motor 404 can alternately actuate the lever arm 410 via compression of the spring 428 to pivot the upper arm 308a (via the lower arm 360a) in a first direction (i.e., toward the other upper arm 308b), such that the catheter body 50 can be gripped between the rotatable gripping pads 314, and in a second opposite direction (i.e., away from the other upper arm 308b), such that the catheter body 50 can be released from between the rotatable gripping pads 314. The motor 404 may also actuate the lever arm 410 to vary the compression of the spring 428 to adjust the gripping force of the upper arms 308 when gripping the catheter body 50.

Figure 46:
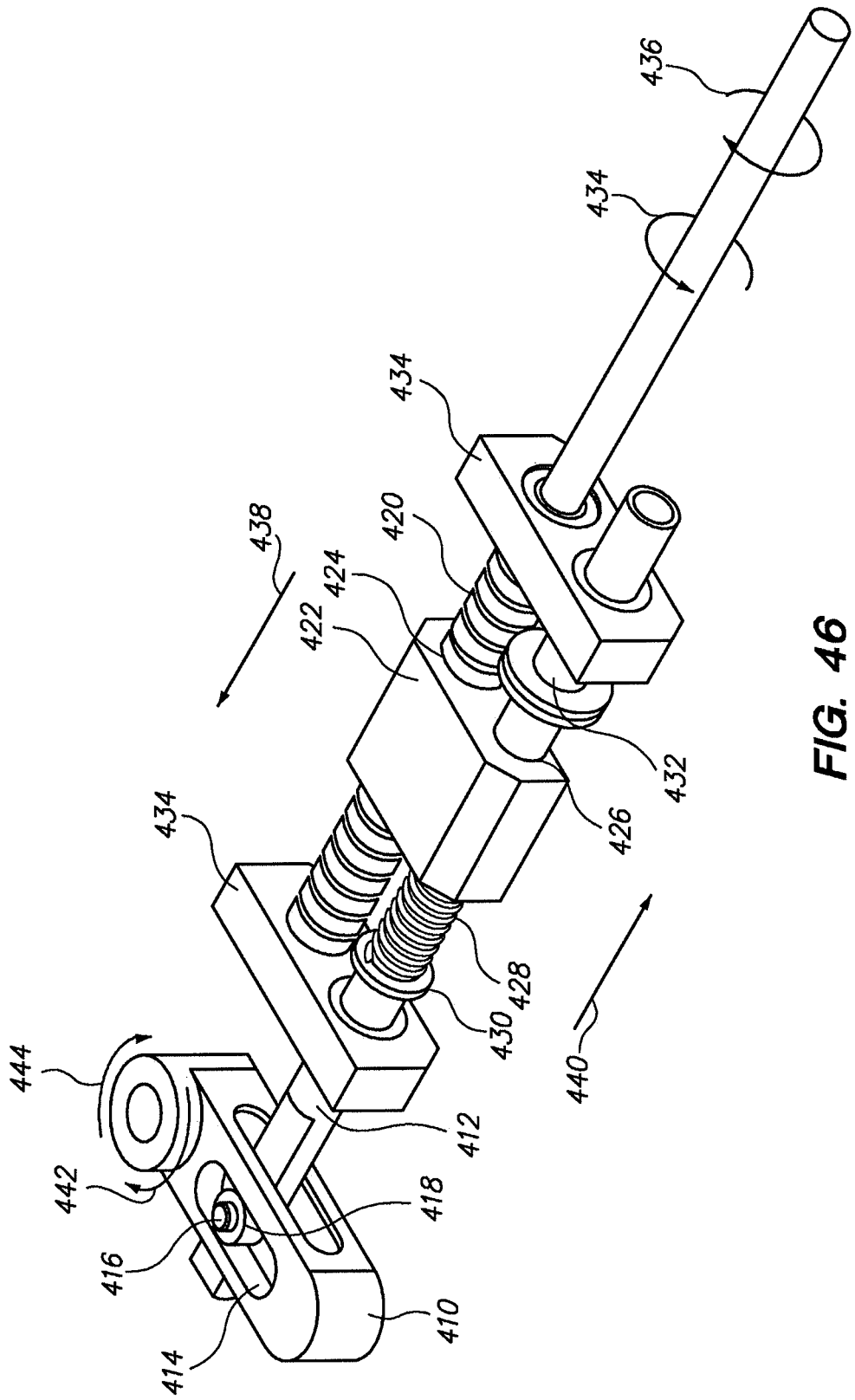
FIG. 46 is a perspective view of a gripping force adjustment mechanism of the driver assembly used in the catheter feeder of FIGS. 27-30, particularly showing the state of the gripping force adjustment mechanism when the catheter feeder is in the closed position.
Figure 47:
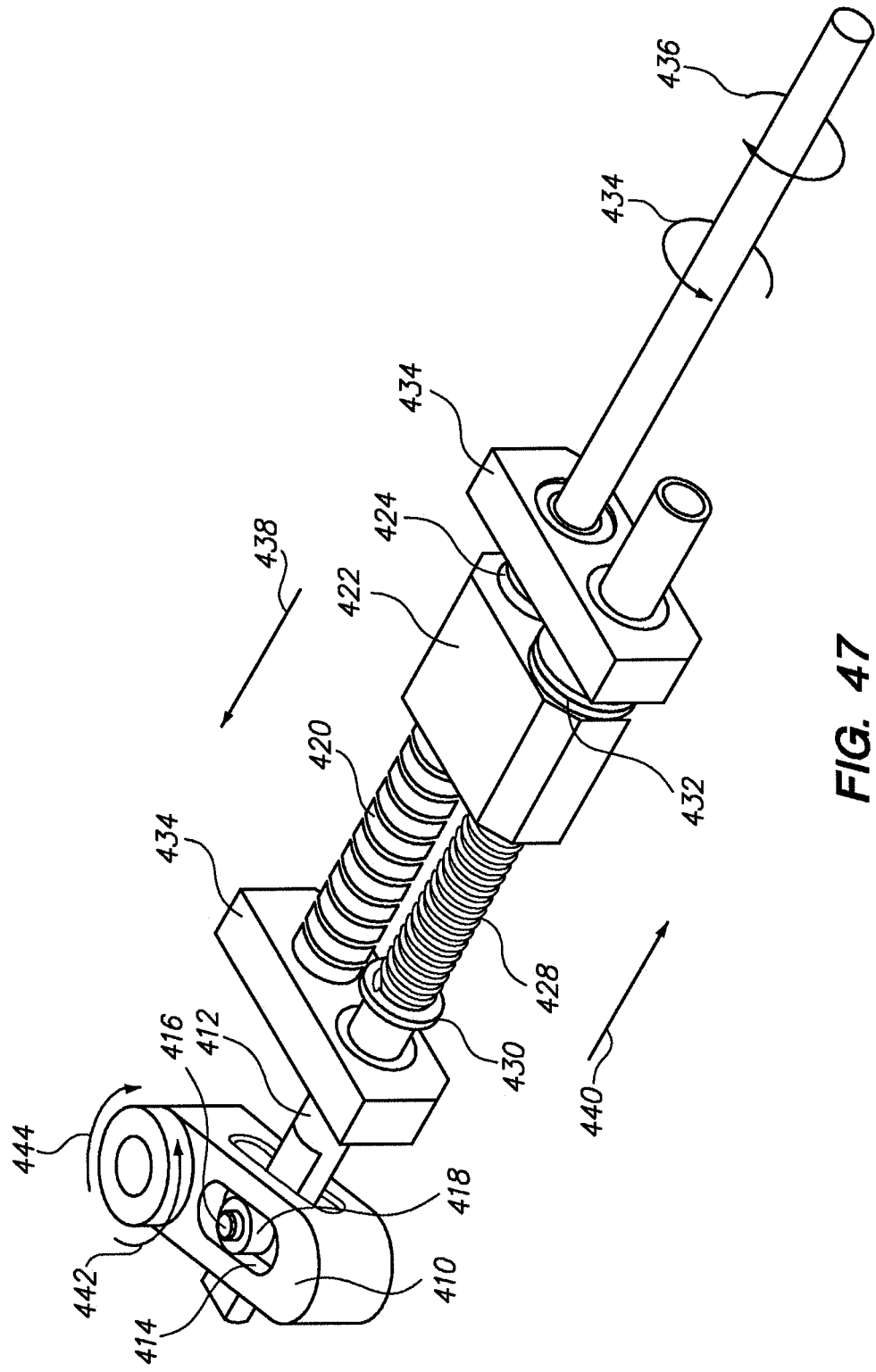
FIG. 47 is a perspective view of the gripping force adjustment mechanism of FIG. 46, particularly showing the state of the gripping force adjustment mechanism when the catheter feeder is in the opened position.
Figure 48:
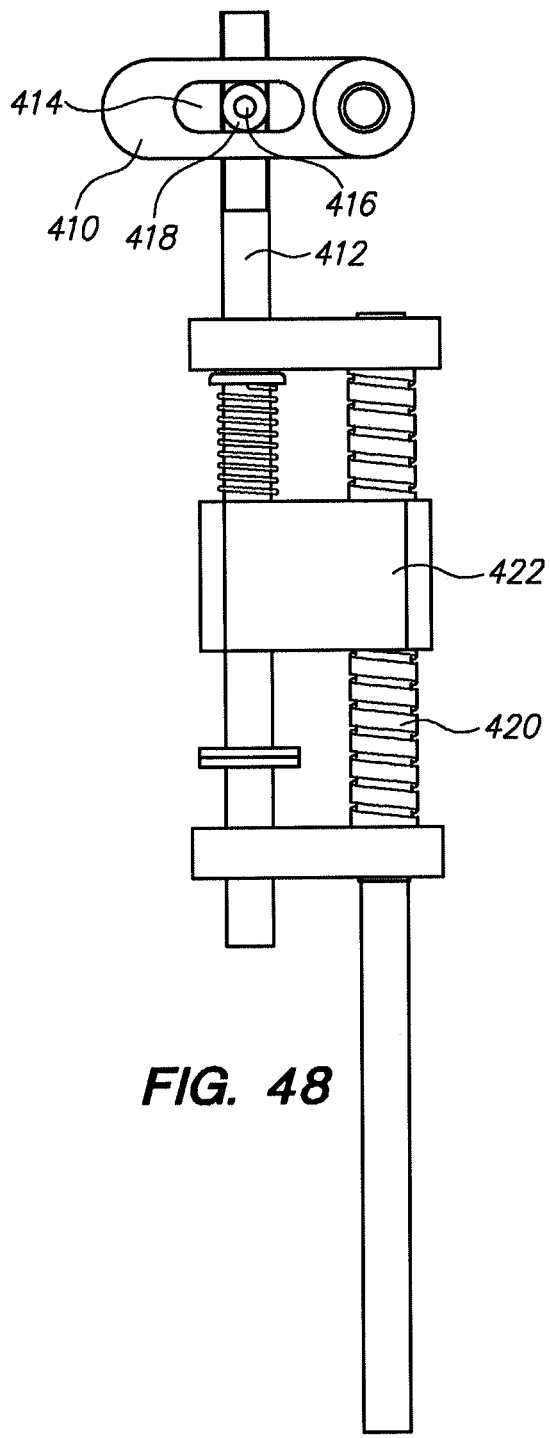
FIG. 48 is a top view of the gripping force adjustment mechanism of FIG. 46, particularly showing the state of the gripping force adjustment mechanism when the catheter feeder is in the closed position.
Figure 49:
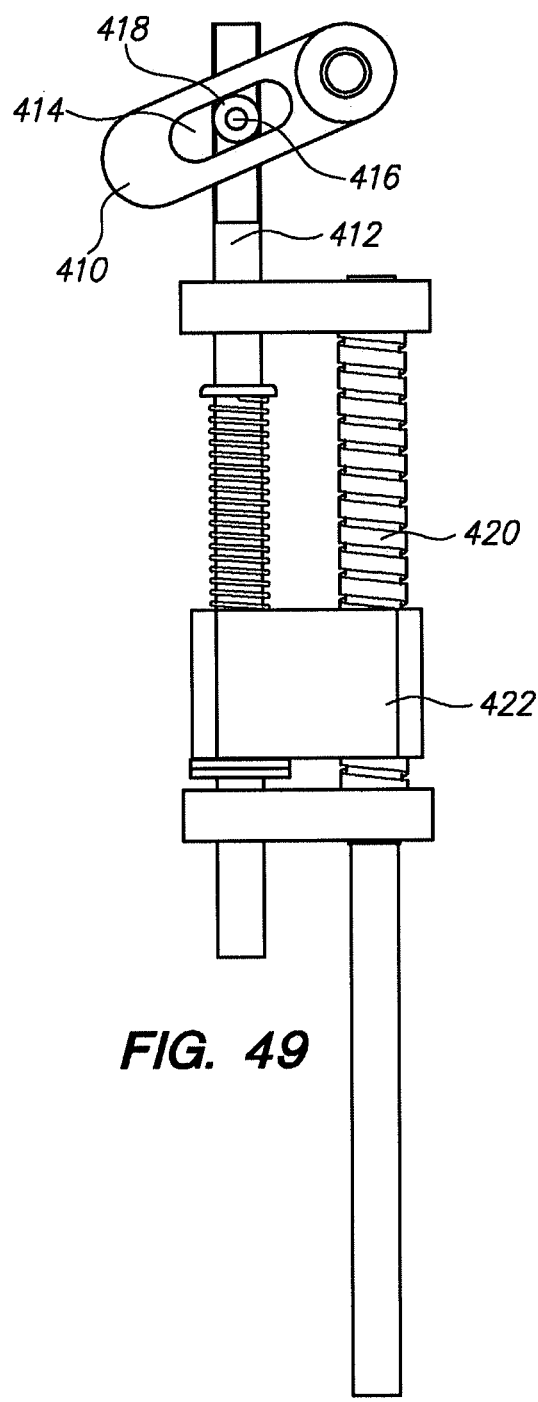
FIG. 49 is a top view of the gripping force adjustment mechanism of FIG. 46, particularly showing the state of the gripping force adjustment mechanism when the catheter feeder is in the opened position.

In particular, rotation of the lead screw 420 via operation of the motor 404 actuates the lower arms 360, and thus the upper arms 308, to pivot away or toward each other. That is, as shown in FIGS. 46 and 48, rotation of the lead screw 420 in one direction 434 linearly displaces the lead nut 422 in the direction 438, which compresses the spring 428. The compressed spring 428 bears against the annular flange 430, thereby translating the horizontal rod 412 in the same direction 438, which in turn rotates the lever arm 410 in the direction 442, and rotates the vertical rod 408 about its longitudinal axis in the same direction 442 to pivot the lower arms 360 (and thus the upper arms 308) toward each other. In contrast, as shown in FIGS. 47 and 49, rotation of the lead screw 420 in the opposite direction 436 linearly displaces the lead nut 422 in the direction 440, which bears against the annular flange 432, thereby translating the horizontal rod 412 in the same direction 440, which in turn rotates the lever arm 410 in the direction 444, and rotates the vertical rod 408 about its longitudinal axis in the same direction 444 to pivot the lower arms 360 away from each other (and thus the upper arms 308).

Assuming that the upper arms 308 are already gripping the catheter body 50, further rotation of the lead screw 420 in the one direction 432 further linearly displaces the lead nut 422 in the direction 436, which further compresses the spring 428. The increased compression force of the spring 428 naturally increases the gripping force between the upper arms 308. In contrast, rotation of the lead screw 420 in the opposite direction 434 linearly displaces the lead nut 422 back in the direction 438, which decompresses the spring 428. The decreased compression force of the spring 428 naturally decreases the gripping force between the upper arms 308. Preferably, to enhance controllability of the gripping force between the upper arms 308 when gripping the catheter body 50, the compression of the spring 428 is proportional to the gripping force.

Although the active catheter feeders 100 and 300 have been described above as being mechanisms for manipulating the advancing/retracting the leader catheter 38 within the guide sheath 36, it should be appreciated that the mechanisms described with respect to the active catheter feeders 100 and 300 can alternatively or optionally be used in the guidewire feeder 82 to advance/retract the guidewire 40 within the leader catheter 38. Furthermore, an alternative embodiments, an active sheath feeder (not shown), which may be identical to the active catheter feeders described herein, may be located at the patient site to prevent buckling of the guide sheath 36 when inserted into the patient. Such an active sheath feeder may manipulate the guide sheath 36 in the same manner as the leader catheter 38 is manipulated by any of the active catheter feeders described herein, and may operate in conjunction with the displacement of entire robotic catheter assembly 18 relative to the support-arm assembly 14, or alternatively in conjunction with the displacement of a sheath carriage (not shown).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical system, comprising:
   a telescoping catheter assembly, comprising an outer sheath and an inner catheter, the outer sheath including an elongate sheath body and a sheath adapter affixed to a proximal end of the sheath body, and the inner catheter including an elongate catheter body and a catheter adapter affixed to a proximal end of the catheter body; and
   an instrument driver comprising:
      a sheath interface configured for mating with the sheath adapter;
      a slidable carriage configured for mating with the catheter adapter;
      a feeder mechanism affixed between the sheath interface and the slidable carriage and engageable with the catheter body, the feeder mechanism comprising:
         a pair of rotatable gripping pads, and
         a pair of arms configured to pivot the pair of rotatable gripping pads towards each other to engage with the catheter body and away from each other to disengage from the catheter body; and
      at least one motor configured for translating the slidable carriage toward the sheath interface to translate the catheter adapter toward the sheath adapter via a first actuator while operating the feeder mechanism to actively advance the catheter body within the sheath body via a second actuator, the second actuator being different from the first actuator,
wherein each of the pair of arms comprises a section gear and the pair of arms are coupled to each other via the section gears such that pivoting one of the pair of arms pivots the other of the pair of arms in an opposite direction.

2. The medical system of claim 1, wherein the at least one motor is configured for translating the slidable carriage away from the sheath interface to translate the catheter adapter away from the sheath adapter while operating the feeder mechanism to actively retract the catheter body within the sheath body.

3. The medical system of claim 1, wherein the sheath adapter and the catheter adapter are releasably engageable with the sheath interface and slidable carriage, respectively.

4. The medical system of claim 1, wherein the pair of rotatable gripping pads are rotatable opposite to each other to actively advance the catheter body within the sheath body.

5. The medical system of claim 1, wherein the telescoping catheter assembly further comprises a guidewire inside the inner catheter, and the instrument driver further comprises a drive mechanism engageable with the guidewire, the drive mechanism configured to advance and retract the guidewire within the catheter body.

6. A medical system, comprising:
a telescoping catheter assembly, the telescoping catheter assembly comprising an outer sheath and an inner catheter, the outer sheath including an elongate sheath body and a sheath adapter affixed to a proximal end of the sheath body, wherein the sheath adapter comprises one or more drive shafts to tension or release pullwires disposed within the outer sheath body, and the inner catheter including an elongate catheter body and a catheter adapter affixed to a proximal end of the catheter body; and
an instrument driver comprising:
a sheath interface configured to mate with the sheath adapter;
a mateable interface configured to mate with the catheter adapter; and
a feeder mechanism affixed between the sheath interface and the mateable interface, the feeder mechanism engageable with the catheter body of the inner catheter to actively advance the inner catheter within the sheath body, the feeder mechanism comprising at least one arm configured to pivot towards the catheter body to engage with the catheter body and away from the catheter body to disengage from the catheter body,
wherein the feeder mechanism further comprises a rotatable gripping pad coupled to a drive gear via a gripping pad gear, wherein pivoting the at least one arm causes the gripping pad gear to rotate about the drive gear.

7. The medical system of claim 6, wherein the feeder mechanism is further configured to actively retract the inner catheter within the sheath body.

8. The medical system of claim 6, wherein the sheath adapter and the catheter adapter are releasably engageable with the sheath interface and mateable interface, respectively.

9. The medical system of claim 6, wherein the rotatable gripping pad comprises a first rotatable gripping pad and the feeder mechanism comprises a second rotatable gripping pad opposing the first rotatable gripping pad, the first and second rotatable gripping pads engagable with the catheter body of the inner catheter and rotatable opposite to each other to actively advance the inner catheter within the sheath body.

10. The medical system of claim 6, wherein the telescoping catheter assembly further comprises a guidewire, and the instrument driver further comprises a drive mechanism engageable with the guidewire and configured to advance and retract the guidewire within the inner catheter.

11. The medical system of claim 10, wherein the drive mechanism is configured to simultaneously advance the guidewire within the catheter body and roll the guidewire about a longitudinal axis.

12. The medical system of claim 6, wherein the feeder mechanism is affixed relative to the sheath interface.

13. The medical system of claim 6, wherein the instrument driver is a robotic instrument driver, the medical system further comprising:
a master input device configured for receiving commands from a user; and
a computer configured for controlling the robotic instrument driver in accordance with the user commands.

14. The medical system of claim 6, wherein the instrument driver further comprises at least one motor configured for translating the mateable interface toward the sheath interface to translate the catheter adapter toward the sheath adapter.

15. A medical system, comprising:
an outer sheath;
an inner catheter;
a sheath interface configured for mating with the sheath;
a carriage configured for mating with the catheter;
a feeder mechanism between the sheath interface and the carriage and engageable with the catheter, the feeder mechanism comprising an arm configured to pivot towards the catheter to engage with the catheter and away from the catheter to disengage from the catheter; and
at least one motor configured for translating the carriage toward the sheath interface while the feeder mechanism is operated to advance the catheter within the sheath, wherein the feeder mechanism further comprises a rotatable gripping pad coupled to a drive gear via a gripping pad gear, wherein pivoting the arm causes the gripping pad gear to rotate about the drive gear.

16. The medical system of claim 15, wherein the arm is a first arm, the feeder mechanism further comprises a second arm configured to pivot towards the first arm to engage with the catheter and away from the first arm to disengage from the catheter.

17. A medical system, comprising:
an outer sheath;
an inner catheter;
a sheath interface configured for mating with the sheath;
a carriage configured for mating with the catheter;
a feeder mechanism between the sheath interface and the carriage and engageable with the catheter, the feeder mechanism comprising a first arm configured to pivot towards the catheter to engage with the catheter and away from the catheter to disengage from the catheter, and a second arm configured to pivot towards the first arm to engage with the catheter and away from the first arm to disengage from the catheter; and
at least one motor configured for translating the carriage toward the sheath interface while the feeder mechanism is operated to advance the catheter within the sheath, wherein the first arm comprises a first section gear, wherein the second arm comprises a second section gear coupled to the first section gear, and wherein pivoting the first arm causes the second arm to pivot in an opposite direction via engagement of the first and second section gears.

* * * * *